US010435742B2

(12) United States Patent
Ju et al.

(10) Patent No.: US 10,435,742 B2
(45) Date of Patent: *Oct. 8, 2019

(54) MASSIVE PARALLEL METHOD FOR DECODING DNA AND RNA

(71) Applicant: The Trustees of Columbia University in the City of New York, New York, NY (US)

(72) Inventors: Jingyue Ju, Englewood Cliffs, NJ (US); Zengmin Li, Flushing, NY (US); John Robert Edwards, St. Louis, MO (US); Yasuhiro Itagaki, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/150,185

(22) Filed: Oct. 2, 2018

(65) Prior Publication Data
US 2019/0031705 A1    Jan. 31, 2019

Related U.S. Application Data

(60) Continuation of application No. 15/915,983, filed on Mar. 8, 2018, which is a continuation of application No. 14/670,748, filed on Mar. 27, 2015, which is a continuation of application No. 13/959,660, filed on Aug. 5, 2013, now Pat. No. 9,133,511, which is a continuation of application No. 13/672,437, filed on Nov. 8, 2012, now abandoned, which is a continuation of application No. 13/339,089, filed on Dec. 28, 2011, now abandoned, which is a continuation of application No. 12/804,284, filed on Jul. 19, 2010, now Pat. No. 8,088,575, which is a continuation of application No. 11/810,509, filed on Jun. 5, 2007, now Pat. No. 7,790,869, which is a continuation of application No. 10/702,203, filed on Nov. 4, 2003, now Pat. No. 7,345,159, which is a division of application No. 09/972,364, filed on Oct. 5, 2001, now Pat. No. 6,664,079, which is a continuation-in-part of application No. 09/684,670, filed on Oct. 6, 2000, now abandoned.

(60) Provisional application No. 60/300,894, filed on Jun. 26, 2001.

(51) Int. Cl.
| | |
|---|---|
| *C12Q 1/68* | (2018.01) |
| *C07H 19/14* | (2006.01) |
| *C12Q 1/6869* | (2018.01) |
| *C07H 21/00* | (2006.01) |
| *C12Q 1/686* | (2018.01) |
| *C12Q 1/6874* | (2018.01) |
| *C12Q 1/6872* | (2018.01) |
| *C07H 19/10* | (2006.01) |
| *C12Q 1/6876* | (2018.01) |
| *C40B 40/00* | (2006.01) |

(52) U.S. Cl.
CPC .......... *C12Q 1/6869* (2013.01); *C07H 19/10* (2013.01); *C07H 19/14* (2013.01); *C07H 21/00* (2013.01); *C12Q 1/68* (2013.01); *C12Q 1/686* (2013.01); *C12Q 1/6872* (2013.01); *C12Q 1/6874* (2013.01); *C12Q 1/6876* (2013.01); *C07B 2200/11* (2013.01); *C12Q 2525/117* (2013.01); *C12Q 2525/186* (2013.01); *C12Q 2535/101* (2013.01); *C12Q 2535/122* (2013.01); *C12Q 2563/107* (2013.01); *C12Q 2565/501* (2013.01); *C40B 40/00* (2013.01)

(58) Field of Classification Search
CPC ............................. C12Q 1/6869; C07H 19/14
USPC ............................................ 536/4.1; 435/6.1
See application file for complete search history.

(56) References Cited

U.S. PATENT DOCUMENTS

| | | | |
|---|---|---|---|
| 4,711,955 A | 12/1987 | Ward et al. | |
| 4,772,691 A | 9/1988 | Herman | |
| 4,804,748 A | 2/1989 | Seela | |
| 4,824,775 A | 4/1989 | Dattagupta et al. | |
| 4,863,849 A | 9/1989 | Melamede | |
| 4,888,274 A | 12/1989 | Redding et al. | |
| 5,043,272 A | 8/1991 | Hartley | |
| 5,047,519 A | 9/1991 | Hobbs, Jr. et al. | |
| 5,118,605 A | 6/1992 | Urdea | |
| 5,151,507 A | 9/1992 | Hobbs, Jr. et al. | |
| 5,174,962 A | 12/1992 | Brennan | |
| 5,175,269 A | 12/1992 | Stavrianopoulos | |

(Continued)

FOREIGN PATENT DOCUMENTS

| | | |
|---|---|---|
| CA | 2425112 | 4/2002 |
| CA | 2408143 | 11/2002 |

(Continued)

OTHER PUBLICATIONS

U.S. Appl. No. 12/804,025, filed Jul. 13, 2010, Balasubramanian et al.

(Continued)

*Primary Examiner* — Jezia Riley
(74) *Attorney, Agent, or Firm* — John P. White; Cooper & Dunham LLP

(57) ABSTRACT

This invention provides methods for attaching a nucleic acid to a solid surface and for sequencing nucleic acid by detecting the identity of each nucleotide analogue after the nucleotide analogue is incorporated into a growing strand of DNA in a polymerase reaction. The invention also provides nucleotide analogues which comprise unique labels attached to the nucleotide analogue through a cleavable linker, and a cleavable chemical group to cap the —OH group at the 3'-position of the deoxyribose.

2 Claims, 28 Drawing Sheets

Specification includes a Sequence Listing.

(56) References Cited

U.S. PATENT DOCUMENTS

| | | |
|---|---|---|
| 5,242,796 A | 9/1993 | Prober et al. |
| 5,302,509 A | 4/1994 | Cheeseman |
| 5,308,990 A | 5/1994 | Takahashi et al. |
| 5,328,824 A | 7/1994 | Ward et al. |
| 5,332,666 A | 7/1994 | Prober et al. |
| 5,383,858 A | 1/1995 | Reilly et al. |
| 5,424,186 A | 6/1995 | Fodor et al. |
| 5,436,143 A | 7/1995 | Hyman |
| 5,437,975 A | 8/1995 | McClelland et al. |
| 5,449,767 A | 9/1995 | Ward et al. |
| 5,476,928 A | 12/1995 | Ward et al. |
| 5,516,664 A | 5/1996 | Hyman |
| 5,534,424 A | 7/1996 | Uhlen et al. |
| 5,547,839 A | 8/1996 | Dower et al. |
| 5,547,859 A | 8/1996 | Goodman et al. |
| 5,556,748 A | 9/1996 | Douglas |
| 5,599,675 A | 2/1997 | Brenner |
| 5,602,000 A | 2/1997 | Hyman |
| 5,614,365 A | 3/1997 | Tabor et al. |
| 5,637,469 A | 6/1997 | Wilding et al. |
| 5,654,419 A | 8/1997 | Mathies et al. |
| 5,658,736 A | 8/1997 | Wong |
| 5,709,999 A | 1/1998 | Shattuck-Eidens et al. |
| 5,714,330 A | 2/1998 | Brenner et al. |
| 5,728,528 A | 3/1998 | Mathies et al. |
| 5,763,594 A | 6/1998 | Hiatt et al. |
| 5,770,365 A | 6/1998 | Lane et al. |
| 5,770,367 A | 6/1998 | Southern et al. |
| 5,789,167 A | 8/1998 | Konrad |
| 5,798,210 A | 8/1998 | Canard et al. |
| 5,804,386 A | 9/1998 | Ju |
| 5,808,045 A | 9/1998 | Hiatt et al. |
| 5,814,454 A | 9/1998 | Ju |
| 5,821,356 A | 10/1998 | Khan et al. |
| 5,834,203 A | 11/1998 | Katzir et al. |
| 5,844,106 A | 12/1998 | Seela et al. |
| 5,849,542 A | 12/1998 | Reeve et al. |
| 5,853,992 A | 12/1998 | Glazer et al. |
| 5,856,104 A | 1/1999 | Chee et al. |
| 5,858,671 A | 1/1999 | Jones |
| 5,869,255 A | 2/1999 | Mathies et al. |
| 5,872,244 A | 2/1999 | Hiatt et al. |
| 5,876,936 A | 3/1999 | Ju |
| 5,885,775 A | 3/1999 | Haff et al. |
| 5,885,813 A | 3/1999 | Davis et al. |
| 5,908,755 A | 6/1999 | Kumar et al. |
| 5,945,283 A | 8/1999 | Kwok et al. |
| 5,948,648 A | 9/1999 | Khan et al. |
| 5,952,180 A | 9/1999 | Ju |
| 5,959,089 A | 9/1999 | Hannessian |
| 5,962,228 A | 10/1999 | Brenner |
| 6,001,566 A | 12/1999 | Canard |
| 6,001,611 A | 12/1999 | Will |
| 6,008,379 A | 12/1999 | Benson et al. |
| 6,013,445 A | 1/2000 | Albrecht et al. |
| 6,028,190 A | 2/2000 | Mathies et al. |
| 6,046,005 A | 4/2000 | Ju et al. |
| 6,074,823 A | 6/2000 | Koster |
| 6,087,095 A | 7/2000 | Rosenthal et al. |
| 6,111,116 A | 8/2000 | Benson et al. |
| 6,136,543 A | 10/2000 | Anazawa et al. |
| 6,175,107 B1 | 1/2001 | Juvinall |
| 6,197,557 B1 | 3/2001 | Makarov et al. |
| 6,207,831 B1 | 3/2001 | Auer et al. |
| 6,210,891 B1 | 4/2001 | Nyren et al. |
| 6,214,987 B1 | 4/2001 | Hiatt et al. |
| 6,218,118 B1 | 4/2001 | Sampson et al. |
| 6,218,530 B1 | 4/2001 | Rothschild et al. |
| 6,221,592 B1 | 4/2001 | Schwartz et al. |
| 6,232,465 B1 | 5/2001 | Hiatt et al. |
| 6,242,193 B1 | 6/2001 | Anazawa et al. |
| 6,245,507 B1 | 6/2001 | Bogdanov |
| 6,248,884 B1 | 6/2001 | Lam et al. |
| 6,255,083 B1 | 7/2001 | Williams |
| 6,255,475 B1 | 7/2001 | Kwiatkowski |
| 6,274,320 B1 | 8/2001 | Rothberg et al. |
| 6,277,607 B1 | 8/2001 | Tyagi et al. |
| 6,287,821 B1 | 9/2001 | Shi et al. |
| 6,294,324 B1 | 9/2001 | Bensimon et al. |
| 6,309,829 B1 | 10/2001 | Livak et al. |
| 6,309,836 B1 | 10/2001 | Kwiatkowski |
| 6,312,893 B1 | 11/2001 | Van Ness et al. |
| 6,316,230 B1 | 11/2001 | Egholm et al. |
| 6,335,155 B1 | 1/2002 | Wells et al. |
| 6,361,940 B1 | 3/2002 | Van Ness et al. |
| 6,380,378 B1 | 4/2002 | Kitamura et al. |
| 6,432,360 B1 | 8/2002 | Church |
| 6,495,680 B1 | 12/2002 | Gong |
| 6,524,829 B1 | 2/2003 | Seeger |
| 6,555,349 B1 | 4/2003 | O'Donnell |
| 6,613,508 B1 | 9/2003 | Ness et al. |
| 6,613,513 B1 | 9/2003 | Parce et al. |
| 6,627,436 B2 | 9/2003 | Sorge et al. |
| 6,627,748 B1 | 9/2003 | Ju et al. |
| 6,632,655 B1 | 10/2003 | Mehta et al. |
| 6,639,088 B2 | 10/2003 | Kwiatkowski |
| 6,664,079 B2 | 12/2003 | Ju et al. |
| 6,664,399 B1 | 12/2003 | Sabesan |
| 6,713,255 B1 | 3/2004 | Makino et al. |
| 6,780,591 B2 | 8/2004 | Williams et al. |
| 6,787,308 B2 | 9/2004 | Balasubramanian et al. |
| 6,818,395 B1 | 11/2004 | Quake et al. |
| 6,833,246 B2 | 12/2004 | Balasubramanian |
| 6,858,393 B1 | 2/2005 | Anderson et al. |
| 6,864,052 B1 | 3/2005 | Drmanac et al. |
| 6,911,345 B2 | 6/2005 | Quake et al. |
| 6,934,636 B1 | 8/2005 | Skierczynski et al. |
| 6,982,146 B1 | 1/2006 | Schneider et al. |
| 7,037,687 B2 | 5/2006 | Williams et al. |
| 7,056,661 B2 | 6/2006 | Korlach et al. |
| 7,056,666 B2 | 6/2006 | Dower et al. |
| 7,057,026 B2 | 6/2006 | Barnes et al. |
| 7,057,031 B2 | 6/2006 | Olejnik et al. |
| 7,074,597 B2 | 7/2006 | Ju |
| 7,078,499 B2 | 7/2006 | Odedra et al. |
| 7,105,300 B2 | 9/2006 | Parce et al. |
| 7,270,951 B1 | 9/2007 | Stemple et al. |
| 7,279,563 B2 | 10/2007 | Kwiatkowski |
| 7,329,496 B2 | 2/2008 | Dower et al. |
| 7,345,159 B2 | 3/2008 | Ju et al. |
| 7,393,533 B1 | 7/2008 | Crotty et al. |
| 7,414,116 B2 | 8/2008 | Milton et al. |
| 7,427,673 B2 | 9/2008 | Balasubramanian et al. |
| 7,459,275 B2 | 12/2008 | Dower et al. |
| 7,541,444 B2 | 6/2009 | Milton et al. |
| 7,566,537 B2 | 7/2009 | Balasubramanian et al. |
| 7,622,279 B2 | 11/2009 | Ju |
| 7,635,578 B2 | 12/2009 | Ju et al. |
| 7,713,698 B2 | 5/2010 | Ju et al. |
| 7,771,973 B2 | 8/2010 | Milton et al. |
| 7,785,790 B1 | 8/2010 | Church et al. |
| 7,790,869 B2 | 9/2010 | Ju et al. |
| 7,883,869 B2 | 2/2011 | Ju et al. |
| 7,982,029 B2 | 7/2011 | Ju et al. |
| 8,088,575 B2 | 1/2012 | Ju et al. |
| 8,158,346 B2 | 4/2012 | Balasubramanian et al. |
| 8,298,792 B2 | 10/2012 | Ju et al. |
| 8,399,188 B2 | 3/2013 | Zhao et al. |
| 8,796,432 B2 | 8/2014 | Ju et al. |
| 8,889,348 B2 | 11/2014 | Ju |
| 9,115,163 B2 | 8/2015 | Ju et al. |
| 9,133,511 B2 | 9/2015 | Ju et al. |
| 9,159,610 B2 | 10/2015 | Zhang et al. |
| 9,175,342 B2 | 11/2015 | Ju et al. |
| 9,255,292 B2 | 2/2016 | Ju et al. |
| 9,297,042 B2 | 3/2016 | Ju et al. |
| 9,708,358 B2 | 7/2017 | Ju et al. |
| 9,718,852 B2 | 8/2017 | Ju et al. |
| 9,719,139 B2 | 8/2017 | Ju et al. |
| 9,725,480 B2 | 8/2017 | Ju et al. |
| 9,868,985 B2 | 1/2018 | Ju et al. |
| 2002/0012966 A1 | 1/2002 | Shi et al. |
| 2002/0168642 A1 | 11/2002 | Drukier |
| 2003/0008285 A1 | 1/2003 | Fischer |

(56) References Cited

U.S. PATENT DOCUMENTS

| | | | |
|---|---|---|---|
| 2003/0022225 A1 | 1/2003 | Monforte et al. |
| 2003/0027140 A1 | 2/2003 | Ju et al. |
| 2003/0044871 A1 | 3/2003 | Cutsforth et al. |
| 2003/0054360 A1 | 3/2003 | Gold et al. |
| 2003/0099972 A1 | 5/2003 | Olejnik et al. |
| 2003/0166282 A1 | 9/2003 | Brown et al. |
| 2003/0180769 A1 | 9/2003 | Metzker |
| 2003/0186256 A1 | 10/2003 | Fischer |
| 2003/0190680 A1 | 10/2003 | Rothschild et al. |
| 2003/0198982 A1 | 10/2003 | Seela et al. |
| 2004/0014096 A1 | 1/2004 | Anderson et al. |
| 2004/0096825 A1 | 5/2004 | Chenna et al. |
| 2005/0032081 A1 | 2/2005 | Ju et al. |
| 2005/0170367 A1 | 8/2005 | Quake et al. |
| 2005/0239134 A1 | 10/2005 | Gorenstein et al. |
| 2006/0003352 A1 | 1/2006 | Lipkin et al. |
| 2006/0057565 A1 | 3/2006 | Ju et al. |
| 2006/0105461 A1 | 5/2006 | Tom-Moy et al. |
| 2006/0160081 A1 | 7/2006 | Milton et al. |
| 2006/0160113 A1 | 7/2006 | Korlach et al. |
| 2006/0240439 A1 | 10/2006 | Smith et al. |
| 2006/0252038 A1 | 11/2006 | Ju |
| 2007/0166705 A1 | 7/2007 | Milton et al. |
| 2009/0088332 A1 | 4/2009 | Ju et al. |
| 2009/0240030 A1 | 9/2009 | Ju et al. |
| 2010/0159531 A1 | 6/2010 | Gordon et al. |
| 2010/0323350 A1 | 12/2010 | Gordon et al. |
| 2011/0014611 A1 | 1/2011 | Ju et al. |
| 2011/0124054 A1 | 5/2011 | Olejnik et al. |
| 2012/0052489 A1 | 3/2012 | Gordon et al. |
| 2012/0142006 A1 | 6/2012 | Ju et al. |
| 2013/0264207 A1 | 10/2013 | Ju et al. |
| 2014/0315191 A1 | 10/2014 | Ju et al. |
| 2015/0037788 A1 | 2/2015 | Ju |
| 2015/0080232 A1 | 3/2015 | Ju et al. |
| 2015/0111759 A1 | 4/2015 | Ju et al. |
| 2015/0119259 A1 | 4/2015 | Ju et al. |
| 2015/0197800 A1 | 7/2015 | Ju et al. |
| 2015/0368710 A1 | 12/2015 | Fuller et al. |
| 2016/0024570 A1 | 1/2016 | Ju et al. |
| 2016/0024574 A1 | 1/2016 | Ju et al. |
| 2016/0041179 A1 | 2/2016 | Ju et al. |
| 2016/0090621 A1 | 3/2016 | Ju et al. |
| 2016/0264612 A1 | 9/2016 | Ju et al. |
| 2017/0088574 A1 | 3/2017 | Ju et al. |
| 2017/0088575 A1 | 3/2017 | Ju et al. |
| 2017/0088891 A1 | 3/2017 | Ju et al. |
| 2017/0313737 A1 | 11/2017 | Ju et al. |
| 2018/0201642 A1 | 7/2018 | Ju et al. |

FOREIGN PATENT DOCUMENTS

| | | |
|---|---|---|
| DE | 4141178 | 6/1993 |
| DE | 20122767 | 8/2007 |
| DE | 112007002932.3 | 8/2015 |
| EP | 0251786 B1 | 11/1994 |
| EP | 0995804 | 4/2000 |
| EP | 1182267 | 2/2002 |
| EP | 1291354 | 3/2003 |
| EP | 0808320 | 4/2003 |
| EP | 1337541 B1 | 3/2007 |
| EP | 1218391 | 4/2007 |
| EP | 0992511 | 3/2009 |
| EP | 2209911 B1 | 10/2013 |
| GB | 2000 0013276 | 6/2000 |
| GB | 2001 0029012 | 12/2001 |
| GB | 2446083 | 3/2011 |
| GB | 2446084 | 3/2011 |
| GB | 2457402 | 9/2011 |
| WO | WO 1989/09282 | 10/1989 |
| WO | WO 89/10977 | 11/1989 |
| WO | WO 1989/11548 | 11/1989 |
| WO | WO 1990/13666 | 11/1990 |
| WO | WO 91/06678 | 5/1991 |
| WO | WO 1991/06678 | 5/1991 |
| WO | WO 1992/10587 | 6/1992 |
| WO | WO 1993/05183 | 3/1993 |
| WO | WO 93/12340 | 10/1993 |
| WO | WO 1993/21340 | 10/1993 |
| WO | WO 1994/14972 | 7/1994 |
| WO | WO 1996/07669 | 3/1996 |
| WO | WO 96/23807 | 8/1996 |
| WO | WO 1996/23807 | 8/1996 |
| WO | WO 96/27025 | 9/1996 |
| WO | WO 1996/27025 | 9/1996 |
| WO | WO 1997/08183 | 3/1997 |
| WO | WO 1997/27317 | 7/1997 |
| WO | WO 1997/35033 | 9/1997 |
| WO | WO 1998/30720 | 7/1998 |
| WO | WO 98/33939 | 8/1998 |
| WO | WO 1998/33939 | 8/1998 |
| WO | WO 1998/44151 | 10/1998 |
| WO | WO 98/53300 | 11/1998 |
| WO | WO 1999/05315 | 2/1999 |
| WO | WO 1999/49082 | 9/1999 |
| WO | WO 1999/57321 | 11/1999 |
| WO | WO 2000/02895 | 1/2000 |
| WO | WO 2000/06770 | 2/2000 |
| WO | WO 2000/09753 | 2/2000 |
| WO | WO 2000/15844 | 3/2000 |
| WO | WO 2000/18956 | 4/2000 |
| WO | WO 2000/21974 | 4/2000 |
| WO | WO 2000/50172 | 8/2000 |
| WO | WO 2000/50642 | 8/2000 |
| WO | WO 00/53812 | 9/2000 |
| WO | WO 2000/53805 | 9/2000 |
| WO | WO 2000/53812 | 9/2000 |
| WO | WO 2000/70073 | 11/2000 |
| WO | WO 2001/16375 | 3/2001 |
| WO | WO 2001/23610 | 4/2001 |
| WO | WO 2001/25247 | 4/2001 |
| WO | WO 2001/27625 | 4/2001 |
| WO | WO 2001/32930 | 5/2001 |
| WO | WO 2001/57248 | 8/2001 |
| WO | WO 2001/57249 | 8/2001 |
| WO | WO 01/92284 | 12/2001 |
| WO | WO 2001/92284 | 12/2001 |
| WO | WO 2002/02813 | 1/2002 |
| WO | WO 02/21098 | 3/2002 |
| WO | WO 2002/22883 | 3/2002 |
| WO | WO 02/29003 | 4/2002 |
| WO | WO 2002/29003 | 4/2002 |
| WO | WO 2002/72892 | 9/2002 |
| WO | WO 2002/079519 | 10/2002 |
| WO | WO 2002/88381 | 11/2002 |
| WO | WO 2002/88382 | 11/2002 |
| WO | WO 2003/02767 | 1/2003 |
| WO | WO 2003/20968 | 3/2003 |
| WO | WO 2003/48178 | 6/2003 |
| WO | WO 2003/48387 | 6/2003 |
| WO | WO 2003/85135 | 10/2003 |
| WO | WO 04/18493 | 3/2004 |
| WO | WO 04/18497 | 3/2004 |
| WO | WO 2004/018493 | 3/2004 |
| WO | WO 2004/18493 | 3/2004 |
| WO | WO 2004/18497 | 3/2004 |
| WO | WO 2004/018497 | 3/2004 |
| WO | WO 2004/055160 | 7/2004 |
| WO | WO 2005/084367 | 9/2005 |
| WO | WO 2006/73436 | 7/2006 |
| WO | WO 2007/002204 | 1/2007 |
| WO | WO 2007/62105 | 5/2007 |
| WO | WO 2008/069973 | 6/2008 |
| WO | WO 2012/083249 | 6/2012 |
| WO | WO 2012/162429 | 11/2012 |
| WO | WO 2013/154999 | 10/2013 |
| WO | WO 2013/191793 | 12/2013 |
| WO | WO 2014/144883 | 9/2014 |
| WO | WO 2014/144898 | 9/2014 |
| WO | WO 2015/123430 | 8/2015 |

(56) References Cited

FOREIGN PATENT DOCUMENTS

| WO | WO 2015/148402 | 10/2015 |
|----|----------------|---------|
| WO | WO 2015/179284 | 11/2015 |

OTHER PUBLICATIONS

U.S. Appl. No. 10/227,131, filed Aug. 23, 2002, Barnes et al.
May 4, 2013 Petition for Inter Partes Review of U.S. Pat. No. 8,158,346, issued Apr. 17, 2012.
Aug. 5, 2013 Patent Owner Preliminary Response to Petition for Inter Partes Review of U.S. Pat. No. 8,158,346, issued Apr. 17, 2012.
May 3, 2013 Declaration of Dr. Bruce Branchaud (Exhibit 1011, filed May 4, 2013 in connection with IPR2013-00266).
Excerpts from the '346 Patent File History (Exhibit 1012, filed May 4, 2013 in connection with IPR2013-00266).
Excerpts from the file history of European Patent Application No. 02781434.2 (Exhibit 1013, filed May 4, 2013 in connection with IPR2013-00266).
Oct. 28, 2013 Decision Instituting Inter Partes Review in connection with IPR2013-00266.
Dec. 30, 2013 Illumine Motion to Amend Under 37 C.F.R. §42.121 in connection with IPR2013-00266.
Floyd Romesburg Declaration, CV, and List of Documents Considered by Romesburg (Exhibits 2004, 2005, and 2028, filed Dec. 30, 2013 in connection with IPR2013-00266).
Bystrom, Branchaud et al., "ATP Analogs with Non-transferable Groups in the g Position as Inhibitors of Glycerol Kinase" Bioorganic & Medicinal Chemistry Letters, 7:2613-2616 (1997) (Exhibit 2021, filed Dec. 30, 2013 in connection with IPR2013-00266).
Pages from Handbook of Reagents for Organic Synthesis: Reagents for Silicon-Mediated Organic Synthesis (Philip L. Fuchs, ed.) (2011) (Exhibit 2022, filed Dec. 30, 2013 in connection with IPR2013-00266).
Eric Vermaas Declaration—Redacted version (Exhibit 2023, filed Dec. 30, 2013 in connection with IPR2013-00266).
Excerpts from Oct. 3, 2013 Bruce Branchaud Deposition Transcript in IPR2013-00128 (Exhibit 2024, filed Dec. 30, 2013 in connection with IPR2013-00266).
Petitioner's Feb. 28, 2014 Opposition to Patentee Motion to Amend in connection with IPR2013-00266.
Second Declaration of Dr. Bruce Branchaud in support of Intelligent Bio-Systems, Inc.'s Opposition to Illumina's Motion to Amend, from Feb. 28, 2014 (Exhibit 1021, filed Feb. 28, 2014 in connection with IPR2013-00266).
Deposition of Floyd Romesberg, Ph. D., from Jan. 14, 2014 (Exhibit 1022, filed Feb. 28, 2014 in connection with IPR2013-00266).
Deposition of Eric Vermaas from Jan. 13, 2014 (Exhibit 1029, filed Feb. 28, 2014 in connection with IPR2013-00266).
Excerpts from Protective Groups in Organic Synthesis (Theodora W. Greene & Peter G. M. Wuts eds., John Wiley & Sons, Inc. 3rd ed. 1999) (1991) (Exhibit 1035, filed Feb. 28, 2014 in connection with IPR2013-00266).
Zavgorodny et al., "1-Alkylthioalkylation of Nucleoside Hydroxyl Functions and Its Synthetic Applications: A New Versatile Method in Nucleoside Chemistry" 32 Tetrahedron Letters 7593 (1991) (Exhibit 1038, filed Feb. 28, 2014 in connection with IPR2013-00266).
Mar. 21, 2014 Patent Owner's Reply to Petitioner's Opposition to Patent Owner's Motion to Amend in connection with IPR2013-00266.
Mar. 11, 2014 Bruce Branchaud Deposition Transcript (Exhibit 2030, filed Mar. 21, 2014 in connection with IPR2013-00266).
Excerpts from Feb. 11, 2014 Bruce Branchaud Deposition Transcript in related IPR2013-00128 (Exhibit 2032, filed Mar. 21, 2014 in connection with IPR2013-00266).
English translation of Loubinoux et al., "Protection of Phenols by the Azidomethylene Group Application to the Synthesis of Unstable Phenols" Tetrahedron, 44:6055-6064 (1988) (Exhibit 2043, filed Mar. 21, 2014 in connection with IPR2013-00266).
Excerpts from Oct. 3, 2013 Bruce Branchaud Deposition Transcript in related Inter Partes Review IPR2013-00128 (Exhibit 2044, filed Mar. 21, 2014 in connection with IPR2013-00266).
Welch et al., "Syntheses of Nucleosides Designed for Combinatorial DNA Sequencing" Chem. Eur. J., 5;951-960 (1999) (Exhibit 2045, filed Mar. 21, 2014 in connection with IPR2013-00266).
Welch et al., Corrigenda to "Syntheses of Nucleosides Designed for Combinatorial DNA Sequencing" Chem. Eur. J., 11:7145 (2005) (Exhibit 2046, filed Mar. 21, 2014 in connection with IPR2013-00266).
Wu et al., "Termination of DNA synthesis by N6-alkylated, not 3'-0-alkylated, photocleavable 2'-deoxyadenosine triphosphates", Nucleic Acids Research 35:6339-6349 (2007) (Exhibit 2047, filed Mar. 21, 2014 in connection with IPR2013-00266).
Taylor et al., "Rise per base pair in helices of double-stranded rotavirus RNA determined by electron microscopy" Virus Research, 2:175-182 (1985) (Exhibit 2048, filed Mar. 21, 2014 in connection with IPR2013-00266).
Watson et al., Molecular Biology of the Gene, Fifth Edition, Chapter 6 (2004) (Exhibit 2049, filed Mar. 21, 2014 in connection with IPR2013-00266).
Shen et al., "RNA structure at high resolution" FASEB J., 9:1023-1033 (1995) (Exhibit 2050, filed Mar. 21, 2014 in connection with IPR2013-00266).
Holtzman et al., "Electron microscopy of complexes of isolated acetylcholine receptor, biotinyl-toxin, and avidin" Proc. Natl. Acad. Sci. USA, 79:310-314 (1982) (Exhibit 2051, filed Mar. 21, 2014 in connection with IPR2013-00266).
Pugliese et al., "Three-dimensional Structure of the Tetragonal Crystal Form of Egg-white Avidin in its Functional Complex with Biotin at 2.7 Angstrom Resolution" Journal of Molecular Biology, 231:698-710 (1993) (Exhibit 2052, filed Mar. 21, 2014 in connection with IPR2013-00266).
Fersht, "Fidelity of replication of phage $\phi$X174 DNA by DNA polymerase III holoenzyme: Spontaneous mutation by misincorporation" Proc. Natl. Acad. Sci. USA, 76:4946-4950 (1979) (Exhibit 2053, filed Mar. 21, 2014 in connection with IPR2013-00266).
Fersht et al., "DNA polymerase accuracy and spontaneous mutation rates: Frequencies of purine-purine, purine-pyrimidine, and pyrimidine-pyrimidine mismatches during DNA replication" Proc. Natl. Acad. Sci. USA, 78:4251-4255 (1981) (Exhibit 2054, filed Mar. 21, 2014 in connection with IPR2013-00266).
Bebenek et al., "Frameshift errors initiated by nucleotide misincorporation" Proc. Natl. Acad. Sci. USA, 87:4946-4950 (1990) (Exhibit 2055, filed Mar. 21, 2014 in connection with IPR2013-00266).
Bebenek et al., "The Effects of dNTP Pool Imbalances on Frameshift Fidelity during DNA Replication" J. Biol. Chem., 267:3589-3596 (1992) (Exhibit 2056, filed Mar. 21, 2014 in connection with IPR2013-00266).
Greene and Wuts, Protective Groups in Organic Synthesis, 3rd ed., Chapter 1 (1999) (Exhibit 2057, filed Mar. 21, in connection with IPR2013-00266).
Apr. 18, 2014 Petitioner Motion for Observations on the Cross-Examination Testimony of Dr. Romesberg, in connection with IPR2013-00266.
Apr. 18, 2014 Petitioner Motion to Exclude Evidence in connection with IPR2013-00266.
Apr. 10, 2014 transcript of Deposition of Floyd Romesberg (Exhibit 1042, filed Apr. 18, 2014 in connection with IPR2013-00266).
Apr. 18, 2014 Patentee Motion to Exclude Evidence in connection with IPR2013-00266.
May 2, 2014 Patentee Response to Petitioner Motion for Observations on Romesberg Testimony, in connection with IPR2013-00266.
Petitioner Demonstratives for May 28, 2014 Oral Hearing (Exhibit 1045, filed May 22, 2014 in connection with IPR2013-00266).
Patentee Demonstratives for May 28, 2014 Oral Hearing (Exhibit 2060, filed May 22, 2014 in connection with IPR2013-00266).
Transcript of May 28, 2014 Oral Hearing in IPR2013-00266, entered Jul. 8, 2014.
Oct. 28, 2014 Final Written Decision in connection with IPR2013-00266.

(56) References Cited

OTHER PUBLICATIONS

Oct. 3, 2012 Petition for Inter Partes Review of U.S. Pat. No. 8,088,575.
Oct. 3, 2012 Motion to Waive Page Limit and Proposed Petition in connection with Petition for Inter Partes Review of U.S. Pat. No. 8,088,575.
Jan. 7, 2013 Preliminary Response under 37 C.F.R. 42.107 in connection with IPR2013-00011.
Mar. 12, 2013 Decision on Petition for Inter Partes Review in connection with IPR2013-00011.
Mar. 26, 2013 Request for Reconsideration in connection with IPR2013-00011.
Mar. 26, 2013 Request for Rehearing under 37 C.F.R. 42.71 of Decision to Institute Inter Partes Review in connection with IPR2013-00011.
Apr. 26, 2013 Opposition to Request for Reconsideration (Rehearing) Under 37 C.F.R. 42.71.(C) in connection with IPR2013-00011.
May 10, 2013 Decision on Request for Rehearing in connection with IPR2013-00011.
Jun. 25, 2013 Motion to Amend Under 37 C.F.R. 42.121 in connection with IPR2013-00011.
Aug. 30, 2013 Substitute Patent Owner Response Under 37 C.F.R. 42.120 in connection with IPR2013-00011.
Sep. 27, 2013 Petitioner Opposition to Motion to Amend in connection with IPR2013-00011.
Sep. 27, 2013 Petitioner Reply to Response to Petition in connection with IPR2013-00011.
Nov. 18, 2013 Substitute Patent Owner Reply on Motion to Amend in connection with IPR2013-00011.
Oct. 2, 2012 Declaration of George Weinstock Under Rule 37 C.F.R. §1.132 (Exhibit 1021, filed Oct. 3, 2012 in connection with IPR2013-00011).
Excerpts of File History of U.S. Pat. No. 8,088,575 (Exhibit 1022, filed Oct. 3, 2012 in connection with IPR2013-00011).
Sep. 27, 2013 Declaration of Kevin Burgess (Exhibit 1053, filed Sep. 27, 2013 in connection with IPR2013-00011).
Jun. 25, 2013 Substitute Declaration of Dr. George L. Trainor [redacted] (Exhibit 2033, filed Aug. 30, 2013 in connection with IPR2013-00011).
Nov. 12, 2013 Petitioner Motion to Exclude Evidence in connection with IPR2012-00007.
Nov. 12, 2013 Patent Owner Motion for Observations on the Cross-Examination Testimony of Kevin Burgess, Ph.D. in connection with IPR2012-00007.
Nov. 12, 2013 Patent Owner Motion to Exclude Evidence in connection with IPR2012-00007.
Nov. 26, 2013 Petitioner's Response to Motion for Observations in connection with IPR2013-00011.
Nov. 26, 2013 Patent Owner's Opposition to Petitioner's Motion to Exclude in connection with IPR2013-00011.
Nov. 26, 2013 Petitioner's Opposition to Motion to Exclude in connection with IPR2013-00011.
Dec. 3, 2013 Petitioner Reply to Patent Owner's Opposition to Motion to Exclude in connection with IPR2013-00011.
Dec. 3, 2013 Patent Owner Reply on Motion to Exclude in connection with IPR2013-00011.
Mar. 6, 2014 Final Written Decision in connection with IPR2013-00011.
Arbo et al. (1993) "Solid Phase Synthesis of Protected Peptides Using New Cobalt (III) Amine Linkers," Int. J. Peptide Protein Res. 42:138-154.
Axelrod, V.D. et al. (1978) "Specific termination of RNA polymerase synthesis as a method of RNA and DNA sequencing," Nucleic Acids Res. 5(10):3549-3563.
Badman, E. R. et al. (2000) "A Parallel Miniature Cylindrical Ion Trap Array," Anal. Chem (2000) 72:3291-3297.
Badman, E. R. et al. (2000) "Cylindrical Ion Trap Array with Mass Selection by Variation in Trap Dimensions," Anal. Chem. 72:5079-5086.

Bai et al. (2003) "Photocleavage of a 2-nitrobenzyl Linker Bridging a Fluorophore to the 5' end of DNA," PNAS, vol. 100, No. 2, pp. 409-413.
Bai, X., Kim, S., Li, Z., Turro, N.J. and Ju, J. (2004) "Design and Synthesis of a Photocleavable Biotinylated Nucleotide for DNA Analysis by Mass Spectrometry," Nucleic Acids Research, 32(2):534-541.
Benson, S.C., Mathies, R.A., and Glazer, A.N. (1993) "Heterodimeric DNA-binding dyes designed for energy transfer: stability and applications of the DNA complexes," Nucleic Acids Res. 21:5720-5726.
Benson, S.C., Singh, P., and Glazer, A.N. (1993) "Heterodimeric DNA-binding dyes designed for energy transfer: synthesis and spectroscopic properties," Nucleic Acids Res. 21:5727-5735.
Bergmann et al. (1995) "Allyl as Internucleotide Protecting Group in DNA Synthesis to be Cleaved Off by Ammonia," Tetrahedron, 51:6971-6976.
Bergseid M., Baytan A.R., Wiley J.P., Ankener W.M., Stolowitz, Hughs K.A., and Chestnut J.D. (2000) "Small-molecule base chemical affinity system for the purification of proteins," BioTechniques 29:1126-1133.
Bi, L., Kim D.H., and Ju, J. (2006) "Design and Synthesis of a Chemically Cleavable Fluorescent Nucleotide, 3'-O-Allyl-dGTP-allyl-Bodipy-FL-510, as a Reversible Terminator for DNA Sequencing by Synthesis" J. Am. Chem. Soc., 128:2542-2543.
Braslavsky I.; Hebert, B.; Kartalov, E.; et al. (2003) "Sequence information can be obtained from single DNA molecules." Proc. Natl. Acad. Sci. 100(7):3960-3964.
Brunckova, J. et al. (1994) "Intramolecular Hydrogen Atom Abstrction in Carbohydrates and Nucleosides: Inversion of an α- to β-Mannopyranoside and Generation of Thymidine C-4' Radicals." Tetrahedron Letters, vol. 35, pp. 6619-6622.
Buck, G.A. et al. (1999) "Design Strategies and Performance of Custom DNA Sequencing Primers," BioTechniques 27(3):528-536.
Burgess, K. et al. (1997) "Photolytic Mass Laddering for Fast Characterization of Oligomers on Single Resin Beads," J. Org. Chem. 62:5662-5663.
Buschmann et al. (1999) "The Complex Formation of alpha,omega-Dicarboxylic Acids and alpha,omega-Diols with Cucurbituril and alpha-Cyclodextrin," Acta Chim. Slov. 46(3):405-411.
Buschmann et al. (2003) "Spectroscopic Study and Evaluation of Red-Absorbing Fluorescent Dyes," Bioconjugate Chem., 14:195-204.
Canard B. et al. (1994) "DNA polymerase fluorescent substrates with reversible 3'-tags," Gene, 148:1-6.
Canard, B. et al. (1995) "Catalytic editing properties of DNA polymerases," Proc. Natl. Acad. Sci. USA 92:10859-10863.
Caetano-Anolies (1994) "DNA Amplification Fingerprinting Using Arbitrary Mini-hairpin Oligonucleotide Primers." Nature Biotechnology, 12:619-623.
Caruthers, M.H. (1985) "Gene synthesis machines: DNA chemistry and its uses," Science 230:281-285.
Chee, M. et al. (1996) "Accessing genetic information with high density DNA arrays," Science 274:610-614.
Chen X. and Kwok, P.-Y. (1997) "Template-directed dye-terminator incorporation (TDI) assay: a homogeneous DNA diagnostic method based on fluorescence resonance energy transfer," Nucleic Acids Res. 25:347-353.
Chiu, N.H., Tang, K., Yip, P., Braun, A., Koster, H., and Cantor, C.R. (2000) "Mass spectrometry of single-stranded restriction fragments captured by an udigested complementary sequence," Nucleic Acids Res. 28:E31.
Collins, F. S.; Morgan, M.; Patrinos, A. (2003) "The Human Genome Project: Lessons from Large-Scale Biology." Science, 300, pp. 286-290.
Crespo-Hernandez et al., (2000) "Part 1. Photochemical and Photophysical Studies of Guanine Derivatives: Intermediates Contributing to its Photodestruction Mechanism in Aqueous Solution and the Participation of the electron Adduct," .Photochemistry and Photobiology, 71(5):534-543.
Drmanac, S.; Kita, D.; Labat, I.; et al. (1998) "Accurate sequencing by hybridization for DNA diagnostics and individual genomics." Nat. Biotech., 16:54-58.

(56) References Cited

OTHER PUBLICATIONS

Edwards, J. et al. (2001) "DNA sequencing using biotinylated dideoxynucleotides and mass spectrometry," Nucleic Acids Res. 29(21):1041-1046.

Elango, N. et al. (1983) "Amino Acid Sequence of Human Respiratory Syncytial Virus Nucleocapsid Protein," Nucleic Acids Research 11(17):5941-5951.

Fallahpour, R.A. (2000) "Photochemical and Thermal reactions of Azido-Oligopyridines: Diazepinones, a New Class of Metal-Complex Ligands," Helvetica Chimica Acta. 83:384-393.

Fei, Z. et al. (1998) "MALDI-TOF mass spectrometric typing of single nucleotide polymorphisms with mass-tagged ddNTPs," Nucleic Acids Research 26(11):2827-2828.

Finzi, L. et al. (1995) "Measurement of Lactose Repressor-Mediated Loop Formation and Breakdown in Single DNA Molecules." Science, 267:378-380.

Fu, D.J., Tang, K., Braun, A., Reuter, D., Darnhofer-Demar, B., Little, D.P., O'Donnell, M.J., Cantor, C.R., and Koster, H. (1998) "Sequencing exons 5 to 8 of the p53 gene by MALDI-TOF mass spectrometry," Nat. Biotechnol. 16:381-384.

Gibson, K.J. et al. (1987) "Synthesis and Application of Derivatizable Oligonucleotides," Nucleic Acids Research, 15(16): 6455-6467.

Godovikova, T.S. et al. (1999) "5-[3-(E)-(4-Azido-2,3,5,6,-tetrafluorobenzamido)propenyl-1]-2'deoxyuridine-5'-triphosphate Substitutes for Thymidine-5'triphosphate in the Polymerase Chain Reaction," Bioconjugate Chem., 10:529-537.

Green, T.W. et al. and Wuts, P.G.M. "Protective Groups in Organic Synthesis" 3rd ed. New York: John Wiley & Sons, Inc., 1999. 96-99, 190-191, 260-261, 542-543, and 750-751.

Griffin, T.J. et al. (1999) "Direct Genetic Analysis by Matrix-Assisted Laser Desorption/Ionization Mass Spectrometry," Proc. Nat. Acad. Sci. USA 96:6301-6306.

Guibé (1997) "Allylic Protecting Groups and Their Use in a Complex Environment Part I: Allylic Protection of Alcohols," Tetrahedron, 53:13509-13556.

Guibé (1998) "Allylic Protecting Groups and Their Use in a Complex Environment Part II: Allylic Protecting Groups and their Removal through Catalytic Palladium π-Allyl Methodology," Tetrahedron, 54:2967-3042.

Hacia J.G., Edgemon K., Sun B., Stern D., Fodor S.A., and Collins F.S. (1998) "Two Color Hybridization Analysis Using High Density Oligonucleotide Arrays and Energy Transfer Dyes," Nucleic Acids Res. 26:3865-6.

Haff L.A., et al. (1997) "Multiplex Genotyping of PCR Products with Mass Tag-Labeled Primers," Nucleic Acids Res. 25(18):3749-3750.

Hafliger, D. et al. (1997) "Seminested RT-PCR Systems for Small Round Structured Viruses and Detection of Enteric Viruses in Seafood," International Journal of Food Microbiology 37:27-36.

Hanshaw et al. (2004) "An Indicator Displacement System for Fluorescent Detection of Phosphate Oxyanions Under Physiological Conditions," Tetrahedron Letters, vol. 45, pp. 8721-8724.

Hayawaka et al. (1993) "O-Allyl Protection of Guanine and Thymine Residues in Oligodeoxyribonucleotides," J. Org. Chem., 58:5551-5555.

Henner, W.D. et al. (1983) "Enzyme Action at 3' Termini of Ionizing Radiation-Induced DNA Strand Breaks," J. Biol. Chem. 258(24):15198-15205.

Hovinen et al. (1994) "Synthesis of 3'-O-(ω-Aminoalkoxymethyl) thymidine 5'-Triphosphates, Terminators of DNA Synthesis that Enable 3'-Labelling," J. Chem. Soc. Perkin Trans., 1:211-217.

Hu et al. (1999) "Optical Mapping of DNA Polymerase I Action and Products," BBRC, 254:466-473.

Huang, B.G. et al. "Synthesis and in vitro Antitumor Activity of Some Amino-deoxy 3-hexofuranosylpyrrolo[2,3-d]pyrimidines." Carbohydrate Research, 1998, 308(3-4):319-328.

Huber et al. (1999) "Monitoring Solid Phase Synthesis by Infrared Spectroscopic Techniques." Analytica Chimica Acta, 393:213.

Hultman et al. (1989) "Direct Solid Phase Sequencing of Genomic and Plasmid DNA Using Magnetic Beads as Solid Support," Nucleic Acids Research 17(3):4937-4946.

Hyman, E.D., (1988) "A new method of sequencing DNA," Analytical Biochemistry 174:423-436.

Ikeda, K. et al. (1995) "A Non-Radioactive DNA Sequencing Method Using Biotinylated Dideoxynucleoside Triphosphates and Delta TTH DNA Polymerase," DNA Research 2(31):225-227.

Ireland, R.E. and Varney, M.D. (1986) "Approach to the total synthesis of chlorothricolide: synthesis of (±)-19.20-dihydro-24-O-methylchlorothricolide, methyl ester, ethyl carbonate," J. Org. Chem. 51:635-648.

Jiang-Baucom, P. et al. (1997) "DNA Typing of Human Leukocyte Antigen Sequence Polymorphisms by Peptide Nucleic Acid Probes and MALDI-TOF Mass Spectrometry," Anal. Chem. 69:4894-4896.

Ju, J., Ruan C., Fuller, C.W., Glazer, A.N., and Mathies R.A. (1995) "Fluorescence energy transfer dye-labeled primers for DNA sequencing and analysis," Proc. Natl. Acad. Sci. USA 92: 4347-4351.

Ju, J., et al. (1996) "Cassette Labeling for Facile Construction of Energy Transfer Fluorescent Primers," Nuc. Acids Res. 24(6):1144-1148.

Ju, J., Glazer, A.N., and Mathies, R.A. (1996) "Energy Transfer Primers: A new Fluorescence Labeling Paradigm for DNA Sequencing and Analysis," Nature Medicine 2:246-249.

Ju, J. et al. (2006) "Four-color DNA Sequencing by Synthesis Using Cleavable Fluorescent Nucleotide Reversible Terminators," Proc. Natl. Acad. Sci. USA, 103(52):19635-40. Epub Dec. 14, 2006.

Jurinke, C., Van De Boom, D., Collazo, V., Luchow, A., Jacob, A., and Koster H. (1997) "Recovery of nucleic acids from immobilized biotin-streptavidin complexes using ammonium hydroxide and application in MALDI-TOF mass spectrometry," Anal. Chem. 69:904-910.

Kamal, A., Laxman, E., and Rao, N.V. (1999) "A mild and rapid regeneration of alcohols from their allylic ethers by chlorotrimethylsilane/sodium iodide," Tetrahedron Lett 40:371-372.

Kan, C.W.; Doherty, E. A. S.; Barron, A. E. (2003) "A novel thermogelling matrix for microchannel DNA sequencing based on poly-N-alkoxyalkylacrylamide copolymers," Electrophoresis, 24, pp. 4161-4169.

Kasianowicz, J.J., Brandin, B., Branton, D. and Deamer, D.W. (1996) "Characterization of Individual Polynucleotide Molecules Using a Membrane Channel," Proc. Natl. Acad. Sci. USA 93:13770-13773.

Kim Sobin et al. (2002) "Solid Phase Capturable Dideoxynucleotides for Multiplex Genotyping Using Mass Spectrometry," Nucleic Acids Research 30(16):e85.1-e85.6.

Kim, S. et al. (2003) "Multiplex Genotyping of the Human Beta2-adrenergic Receptor Gene Using Solid-phase Capturable Dideoxynucleotides and Mass Spectrometry," Analytical Biochemistry 316:251-258.

Kimzey A.L. et al. (1998) "Specific Regions of Contact Between Human T-cell Leukemia Virus Type I Tax Protein and DNA Identified by Photocross-linking," Journal of Biological Chemistry, 273(22): 13768-13775.

Kitamura et al. (2002) "(P(C6H5)3)CpRu+Catalyzed Deprotection of Allyl Carboxylic Esters," J. Org. Chem., 67:4975-4977.

Kloosterman et al. (1985) "The relative stability of allyl ether, allyloxycarbonyl ester and prop-2 enylidene acetal, protective groups toward Iridium, Rhodium and Palladium catalysts," Tetrahedron Letters, 26:5045-5048.

Kokoris, M. et al. (2000) "High-throughput SNP Genotyping With the Masscode System," Molecular Diagnosis 5(4):329-340.

Kolb et al. (2001) "Click Chemistry: Diverse Chemical Function From a Few Good Reactions," Angew. Chem. Int. Ed. 40:2004-2021.

Kraevskii, A.A. et al. (1987) "Substrate Inhibitors of DNA Biosynthesis," Molecular Biology 21:25-29.

*Illumina, Inc. v. The Trustees of Columbia University in the City of New York*, Case Nos. IPR2018-00291, IPR2018-00318, IPR2018-00322, IPR2018-00385, Videotaped Deposition of Floyd Romesberg, Ph.D. (Sep. 19, 2018), vol. I.

(56) References Cited

OTHER PUBLICATIONS

Video Deposition Transcript of Floyd Romesberg, Ph.D. dated Jan. 14, 2019 in Case No. IPR2013-00128 (Exhibit 2080 marked in Videotaped Deposition of Floyd Romesberg, Ph.D. (Sep. 19, 2018), vol. I).
Video Deposition Transcript of Floyd Romesberg, Ph.D. dated Apr. 10, 2014 in Case No. IPR2013-00266 (Exhibit 2082 marked in Videotaped Deposition of Floyd Romesberg, Ph.D. (Sep. 19, 2018), vol. I).
Substitute Declaration of Floyd Romesberg, Ph.D. in Support of Patent Owner's Motion to Amend in Case IPR2013-00128 (Exhibit 2083 marked in Videotaped Deposition of Floyd Romesberg, Ph.D. (Sep. 19, 2018), vol. I).
Second Declaration of Floyd Romesberg, Ph.D. in Case IPR2013-00266 (Exhibit 2081 marked in Videotaped Deposition of Floyd Romesberg, Ph.D.
Jannasch, H. W. (1992) "Deep Sea Hydrothermal Vents: Underwater Oases," The NEB Transcript 4(1):11-13 (Exhibit 2084 marked in Videotaped Deposition of Floyd Romesberg, Ph.D. (Sep. 19, 2018) , vol. I).
Levine, L. et al. (1963) "The Relationship of Structure to the Effectiveness of Denaturing Agents for Deoxyribonucleic Acid," Biochem. 2(1):168-175 (Exhibit 2085 marked in Videotaped Deposition of Floyd Romesberg, Ph.D. (Sep. 19, 2018), Volume I).
Kit, S. (1963) "Deoxyribonucleic Acids," Annu. Rev. Biochem. 32:43-82 (Exhibit 2086 marked in Videotaped Deposition of Floyd Romesberg, Ph.D. (Sep. 19, 2018), vol. I).
Lindahl, T. & Nyberg, B. (1972) "Rate of Depurination of Native Deoxyribonucleic Acid," Biochem. 11(19):3610-3618 (Exhibit 2087 marked in Videotaped Deposition of Floyd Romesberg, Ph.D. (Sep. 19, 2018) vol. I).
Handwritten notes (Exhibit 2090 marked in Videotaped Deposition of Floyd Romesberg, Ph.D. (Sep. 19, 2018), vol. I.
*Illumina, Inc.* v. *The Trustees of Columbia University in the City of New York*, Case Nos. IPR2018-00291, IPR2018-00318, IPR2018-00322, IPR2018-00385, Videotaped Deposition of Floyd Romesberg, Ph.D. (Sep. 20, 2018), vol. II.
Hamed, O. et al. (2001) "Palladium(II)-Catalyzed Oxidation of Aldehydes and Ketones. 1. Carbonylation of Ketones with Carbon Monoxide Catalyzed by Palladium(II) Chloride in Methanol," J. Org. Chem. 66(1):180-185 (Exhibit 2089 marked in Videotaped Deposition of Floyd Romesberg, Ph.D. (Sep. 20, 2018), vol. II).
Pillai, C. K. S. & Nandi, U. S. (1977) "Interaction of Palladium (II) With DNA," Biochimica et Biophysica Acta 474:11-16 (Exhibit 2094 marked in Videotaped Deposition of Floyd Romesberg, Ph.D. (Sep. 20, 2018), vol. II).
Complaint for Patent Infringement on behalf of The Trustees of Columbia University in the City of New York and QIAGEN Waltham, Inc., filed Jul. 18, 2017 in connection with *Trustees of Columbia University in the City of New York and QIAGEN Waltham, Inc.* v. *Illumina, Inc.*, C.A. No. 17-973 (GMS) (D. Del. Filed Jul. 18, 2017).
Amended Complaint for Patent Infringement on behalf of The Trustees of Columbia University in the City of New York and QIAGEN Waltham, Inc., filed Aug. 1, 2017 in connection with *Trustees of Columbia University in the City of New York and QIAGEN Waltham, Inc.* v. *Illumina, Inc.*, C.A. No. 17-973 (GMS) (D. Del. Filed Jul. 18, 2017).
FastTrack Whole-Genome Sequencing Service Provider, https://www.illumina.com/services/sequencing-services.html (Exhibit 4 of Amended Complaint for Patent Infringement on behalf of The Trustees of Columbia University in the City of New York and QIAGEN Waltham, Inc., filed Aug. 1, 2017 in connection with *Trustees of Columbia University in the City of New York and QIAGEN Waltham, Inc.* v. *Illumina, Inc.*, C.A. No. 17-973 (GMS) (D. Del. Filed Jul. 18, 2017)).
Second Amended Complaint for Patent Infringement on behalf of The Trustees of Columbia University in the City of New York and QIAGEN Waltham, Inc., filed Aug. 8, 2017 in connection with *Trustees of Columbia University in the City of New York and QIAGEN Waltham, Inc.* v. *Illumina, Inc.*, C.A. No. 17-973 (GMS) (D. Del. Filed Jul. 18, 2017).
Illumina, Inc.'s Answer to The Trustees of Columbia University in the City of New York and QIAGEN Waltham, Inc.'s Second Amended Complaint, filed Oct. 2, 2017 in connection with *Trustees of Columbia University in the City of New York and QIAGEN Waltham, Inc.* v. *Illumina, Inc.*, C.A. No. 17-973 (GMS) (D. Del. Filed Jul. 18, 2017).
Third Amended Complaint for Patent Infringement on behalf of The Trustees of Columbia University in the City of New York and Qiagen Sciences, LLC, filed Feb. 16, 2018 in connection with *Trustees of Columbia University in the City of New York and QIAGEN Waltham, Inc.* v. *Illumina, Inc.*, C.A. No. 17-973 (GMS) (D. Del. Filed Jul. 18, 2017).
Illumina, Inc.'s Answer to The Trustees of Columbia University in the City of New York and Qiagen Sciences, LLC's Third Amended Complaint, filed Mar. 2, 2018 in connection with *Trustees of Columbia University in the city of New York and QIAGEN Waltham, Inc.* v. *Illumina, Inc.*, C.A. No. 17-973 (GMS) (D. Del. Filed Jul. 18, 2017).
U.S. Appl. No. 09/684,670, filed Oct. 6, 2000, Ju et al.
Aug. 19, 2013 Petition 1 of 2 for Inter Partes Review of U.S. Pat. No. 7,566,537, issued Jul. 28, 2009.
Aug. 30, 2013 Revised Petition 1 of 2 for Inter Partes Review of U.S. Pat. No. 7,566,537, issued Jul. 28, 2009.
Aug. 16, 2013 Declaration of Dr. Bruce Branchaud (Exhibit 1011, filed Aug. 19, 2013 in connection with IPR2013-00517).
Excerpts from the Mar. 20, 2013 Deposition Transcript of Dr. Xiaohai Liu (Exhibit 1012, filed Aug. 19, 2013 in connection with IPR2013-00517).
Feb. 13, 2014 Decision of Institution of Inter Partes Review IPR2013-00517.
May 5, 2014 Patent Owner Response in connection with IPR2013-00517.
IBS's Answer, Affirmative Defenses & Counterclaims to Illumina, Inc. and Illumina Cambridge Ltd.'s Second Amended Counterclaims to Amended Complaint, Columbia v. Illumina, No. 12-CV-00376 (D. Del) (Exhibit 2005, filed May 5, 2014 in connection with IPR2013-00517).
Excerpts from prosecution history of U.S. Pat. No. 7,566,537, issued Jul. 28, 2009, Barnes et al. (Exhibit 2010, filed May 5, 2014 in connection with IPR2013-00517).
May 5, 2014 Declaration of Floyd Romesberg, Ph.D. (Exhibit 2011, filed May 5, 2014 in connection with IPR2013-00517).
Ranganathan et al., "Facile Conversion of Adenosine into New 2'-Substituted-2'-Deoxy-Arabinofuranosyladenine Derivatives: Stereospecific Syntheses of 2'-Azido-2'-Deoxy-, 2'-Amino-2'-Deoxy-, and 2'-Mercapto-2'-Deoxy-β-D-Arabinofuranosyladenines" Tetrahedron Letters 45:4341-44 (1978) (Exhibit 2013, filed May 5, 2014 in connection with IPR2013-00517).
Mungall et al., "Use of the Azido Group in the Synthesis of 5' Terminal Aminodeoxythymidine Oligonucleotides" J. Org. Chem., 40:1659-1662 (1975) (Exhibit 2014, filed May 5, 2014 in connection with IPR2013-00517).
Pilard et al., "A Stereospecific Synthesis of (±), α-Conhydrine and (+) β-Conhydrine)" Tet. Lett., 25:1555-1556 (1984) (Exhibit 2016, filed May 5, 2014 in connection with IRP2013-00517).
"Synthesis of a Novel Stable $GM_3$-Lactone Analogue as Hapten for a Possible Immunization against Cancer" Tietze et al., Angew. Chem. Int. Ed., 36:1615, 1616 (1997) (Exhibit 2017, filed May 5, 2014 in connection with IPR2013-00517).
Kit, "Deoxyribonucleic Acids" Annual Rev. Biochem, 32:43 (1963) (Exhibit 2018, filed May 5, 2014 in connection with IPR2013-00517).
Canard et al., "Catalytic editing properties of DNA polymerases" PNAS USA 92:10859 (1995) (Exhibit 2019, filed May 5, 2014 in connection with IPR2013-00517).
The Merck Index, p. 9815 (entry for Triphenylphosphine) ($13^{th}$ Edition, 2001) (Exhibit 2020, filed May 5, 2014 in connection with IPR2013-00517).

(56) References Cited

OTHER PUBLICATIONS

Lee et al., "Unwinding of double-stranded DNA helix by dehydration" PNAS 78:2838-42 (1981) (Exhibit 2021, filed May 5, 2014 in connection with IPR2013-00517).
Christensen et al., "Specific Chemical Synthesis of Ribonucleoside O-Benzyl Ethers" J. Am. Chem. Soc., 37:3398 (1972) (Exhibit 2022, filed May 5, 2014 in connection with IPR2013-00517).
Watkins et al., "Synthesis of Oligodeoxyribonucleotides Using N-Benzyloxycarbonyl-Blocked Nucleosides", J. Am. Chem. Soc. 104:5702-08 (1982) (Exhibit 2023, filed May 5, 2014 in connection with IPR2013-00517).
Yoshimoto et al., "Tris(2,4,6-trimethoxyphenyl)phosphine (TTMPP): A Novel Catalyst for Selective Deacetylation" Chemistry Letters 30:934-35 (2001) (Exhibit 2025, filed May 5, 2014 in connection with IPR2013-00517).
Chapter 3 of Protective Groups in Organic Synthesis (Theodora W. Greene & Peter G. M. Wuts eds., John Wiley & Sons, Inc. 3rd ed. 1999) (1991) (Exhibit 2026, filed May 5, 2014 in connection with IPR2013-00517).
Bentley et al., "Accurate whole human genome sequencing using reversible terminator chemistry" Nature 456:53-59 (2008) (Exhibit 2027, filed May 5, 2014 in connection with IPR2013-00517).
Shendure et al., "Advanced Sequencing Technologies: Methods and Goals" Nature Reviews Genetics, 5:335-44 (2004) (Exhibit 2029, filed May 5, 2014 in connection with IPR2013-00517).
Transcript of Apr. 8, 2014 Deposition of Bruce Branchaud, Ph.D. (Exhibit 2039, filed May 5, 2014 in connection with IPR2013-00517).
Excerpts of Transcript of Mar. 20, 2013 Deposition of Dr. Xiaohai Liu in Columbia v. Illumina, 12-cv-376 (D. Del) (Exhibit 2044, filed May 5, 2014 in connection with IPR2013-00517).
Ruparel et al., "Design and synthesis of a 3-O-allyl photocleavable fluorescent nucleotide as a reversible terminator for DNA sequencing by synthesis" PNAS 102:5932-5937 (2005) (Exhibit 2047, filed May 5, 2014 in connection with IPR2013-00517).
Mardis, "A decade's perspective on DNA sequencing technology" Nature 470:198-203 (2011) (Exhibit 2050, filed May 5, 2014 in connection with IPR2013-00517).
Meng et al., "Design and Synthesis of a Photocleavable Fluorescent Nucleotide 3'-O-Allyl-dGTP-PC-Bodipy-FL-510 as a Reversible Terminator for DNA Sequencing by Synthesis" J. Org. Chem 71:3248-52 (2006) (Exhibit 2051, filed May 5, 2014 in connection with IPR2013-00517).
Bi et al., "Design and Synthesis of a Chemically Cleavable Fluorescent Nucleotide, 3'-O-Allyl-dGTP-allyl-Bodipy-FL-510, as a Reversible Terminator for DNA Sequencing by Synthesis" J Am Chem Soc, 128:2542-43 (2006) (Exhibit 2052, filed May 5, 2014 in connection with IPR2013-00517).
Meng, "Tandem Aldol-Allylation Reactions Promoted by Strained Silacycles and Design and Synthesis of Modified Fluorescent Nucleotides for DNA Sequencing by Synthesis", Student Thesis (2006) (Exhibit 2053, filed May 5, 2014 in connection with IPR2013-00517).
Wu et al., "3'-O-modified nucleotides as reversible terminators for pyrosequencing" PNAS, 104:16462-67 (2007) (Exhibit 2054, filed May 5, 2014 in connection with IPR2013-00517).
Kim, "Four-Color DNA Sequencing by Synthesis on a Chip Using Cleavable Fluorescent Nucleotide Reversible Terminators", Student Thesis (2008) (Exhibit 2055, filed May 5, 2014 in connection with IPR2013-00517).
Wu, "Molecular Engineering of Novel Nucleotide Analogues for DNA Sequencing by Synthesis", Student Thesis (2008) (Exhibit 2056, filed May 5, 2014 in connection with IPR2013-00517).
Zhang, "Development of New DNA Sequencing Approaches and Investigation of Vision-related Proteins Using Synthetic Chemistry", Student Thesis (2008) (Exhibit 2057, filed May 5, 2014 in connection with IPR2013-00517).
Guo et al., "Four-color DNA sequencing with 3'-O-modified nucleotide reversible terminators and chemically cleavable fluorescent dideoxynucleotides", PNAS 105:9145 (Exhibit 2058, filed May 5, 2014 in connection with IPR2013-00517).
Guo, "Molecular Engineering of Novel Nucleotide Analogues for DNA Sequencing and Analysis", Student Thesis (2009) (Exhibit 2059, filed May 5, 2014 in connection with IPR2013-00517).
Yu, "Novel Strategies to Increase Read Length and Accuracy for DNA Sequencing by Synthesis", Student Thesis (2010) (Exhibit 2060, filed May 5, 2014 in connection with IPR2013-00517).
Qui, "Novel Molecular Engineering Approaches for Genotyping and DNA Sequencing", Student Thesis (2010) (Exhibit 2062, filed May 5, 2014 in connection with IPR2013-00517).
Kraevskii et al., "Substrate Inhibitors of DNA Biosynthesis", Molecular Biology 21:25-29 (1987) (Exhibit 2073, filed May 5, 2014 in connection with IPR2013-00517).
Dantas et al., "Stannous chloride mediates single strand breaks in plasmid DNA through reactive oxygen species formation", Toxicology Ltrs. 110:129-36 (1999) (Exhibit 2074, filed May 5, 2014 in connection with IPR2013-00517).
Burgess et al., "An Approach to Photolabile, Fluorescent Protecting Groups", J. Org. Chem 62:5165-68 (1997) (Exhibit 2077, filed May 5, 2014 in connection with IPR2013-00517).
Petitioner Reply to Patent Owner Response, filed Jul. 28, 2014 in connection with IPR2013-00517.
Ireland et al., Approach to the Total Synthesis of Chlorothricolide: Synthesis of (+)-19,20-Dihydro-24-O-methylchlorothricolide, Methyl Ester, Ethyl Carbonate, 51 J. Org. Chem. 635 (1986) (Exhibit 1019, filed Jul. 28, 2014 in connection with IPR2013-00517).
Gordon et al., Abstract, The Relationship of Structure to Effectiveness of Denaturing Agents for DNA, Biophysical Society 6th Annual Meeting (Washington, 1962) (Exhibit 1020, filed Jul. 28, 2014 in connection with IPR2013-00517).
Page 295 from Mar. 20, 2003 deposition of Dr. Xiaohai Liu, *The Trustees of Columbia University and Intelligent Bio-Systems, Inc. v. Illumina*, 12-376 (GMS) (D. Del.) (Exhibit 1022, filed Jul. 28, 2014 in connection with IPR2013-00517).
Transcript, Jul. 8, 2014 Deposition of Floyd Romesberg, Ph.D. (Exhibit 1025, filed Jul. 28, 2014 in connection with IPR2013-00517).
Transcript, Jul. 15, 2014 Deposition of Kevin Burgess, Ph.D. (Exhibit 1026, filed Jul. 28, 2014 in connection with IPR2013-00517).
Patent prosecution excerpt from file history of U.S. Pat. No. 7,566,537 (U.S. Appl. No. 11/301,578) (Exhibit 1030, filed Jul. 28, 2014 in connection with IPR2013-00517).
Second Declaration of Dr. Bruce Branchaud in Support of Intelligent Bio-Systems, Inc.'s Reply to Illumina's Patent Owner Response (Exhibit 1031, filed Jul. 28, 2014 in connection with IPR2013-00517).
Gololobov and Kasukhin, Recent advances in the Staudinger reaction, Tetrahedron 48:1353-1406 (1992) (Exhibit 1032, filed Jul. 28, 2014 in connection with IPR2013-00517).
Saxon and Bertozzi, Cell Surface Engineering by a Modified Staudinger Reaction, Science 287:2007-2010 (2000) (Exhibit 1034, filed Jul. 28, 2014 in connection with IPR2013-00517).
Faucher and Grand-Maitre, tris(2-Carboxyethyl)phosphine (TCEP) for the Reduction of Sulfoxides, Sulfonylchlorides, N-Oxides, and Azides, Synthetic Communications 33:3503-3511 (2003) (Exhibit 1036, filed Jul. 28, 2014 in connection with IPR2013-00517).
Knouzi et al., Reductions of Azides by Triphenylphosphine in the presence of water: a General and chemoselective method of access to primary amines, Bull. Soc. Chin.. Fr., 1-12 (1985), and translation (Exhibits 1037 and 1038, filed Jul. 28, 2014 in connection with IPR2013-00517).
Mag and Engels, Synthesis and selective cleavage of oligodeoxyribonucleotides containing non-chiral internucleotide phosphoramidate linkages, Nucleic Acids Research 15:5973-5988 (1989) (Exhibit 1041, filed Jul. 28, 2014 in connection with IPR2013-00517).
Chang and Bollum, Molecular biology of terminal transferase, CRC Critical Reviews in Biochemistry 21:27-52 (1986) (Exhibit 1043, filed Jul. 28, 2014 in connection with IPR2013-00517).
Chen, DNA polymerases drive DNA sequencing-by-synthesis technologies: both past and present, Frontiers in Microbiology, vol. 5,

(56) References Cited

OTHER PUBLICATIONS

Article 305, 1-11 (2014) (Exhibit 1044, filed Jul. 28, 2014 in connection with IPR2013-00517).
Declaration of Dr. Michael Metzker in Suppoert of Intelligent Bio-Systems, Inc's Reply to Illumina's Patent Owner Response (Exhibit 1046, filed Jul. 28, 2014 in connection with IPR2013-00517).
Lebreton et al., Structure-Immunosuppressive Activity Relationships of New Analogues of 15-Deoxyspergualin. 2. Structural Modifications of the Spermidine Moiety, Journal of Medicinal Chemistry 42:4749-4763 (1999) (Exhibit 1047, filed Jul. 28, 2014 in connection with IPR2013-00517).
Levine et al., The Relationship of Structure to the Effectiveness of Denaturing Agents for Deoxyribonucleic Acid, Biochemistry 2:168-175 (1963) (Exhibit 1048, filed Jul. 28, 2014 in connection with IPR2013-00517).
Efimov et al., An azidomethyl protective group in the synthesis of oligoribonucleotides by the phosphotriester method, 35:250-253 (2009) (Exhibit 1049, filed Jul. 28, 2014 in connection with IPR2013-00517).
Kirby, A new method for the isolation of deoxyribonucleic acids: Evidence of the nature of bonds between deoxyribonucleic acids and proteins, Biochemical Journal 66:495-504 (1957) (Exhibit 1050, filed Jul. 28, 2014 in connection with IPR2013-00517).
Bentley et al., Accurate whole human genome sequencing using reversible terminator chemistry. Nature 456:53 (2008)—Supplementary Information (Exhibit 1051, filed Jul. 28, 2014 in connection with IPR2013-00517).
Petitioner Motion to Exclude Evidence, filed Sep. 2, 2014 in connection with IPR2013-00517.
Patent Owner Motion to Exclude Evidence, filed Sep. 2, 2014 in connection with IPR2013-00517.
Patent Owner Motion for Observations on the Cross-Examination Testimony of Bruce Branchaud, Ph.D. and Michael Metzker, Ph.D., filed Sep. 2, 2014 in connection with IPR2013-00517.
Metzker, "Sequencing Technologies—The Next Generation" Nature Reviews Genetics, 11:31-46 (2010) (Exhibit 2139, filed Sep. 2, 2014 in connection with IPR2013-00517).
Tsai et al., "Versatile and Efficient Synthesis of a New Class of Aza-Based Phosphinic Amide Ligands via Unusual P—C Cleavage" Helvetica Chimica Acta, 89:3007-3017 (2006) (Exhibit 2140, filed Sep. 2, 2014 in connection with IPR2013-00517).
Treinin, General and Theoretical Aspects, Chapter 1 (pp. 1-55) in The Chemistry of the Azido Group (Saul Patai, Ed.) (1971) (Exhibit 2141, filed Sep. 2, 2014 in connection with IPR2013-00517).
Hanlon, "The Importance of London Dispersion Forces in the Maintenance of the Deoxyribonucleic Acid Helix" Biochemical and Biophysical Research Communications, 23:861-867 (1966) (Exhibit 2142, filed Sep. 2, 2014 in connection with IPR2013-00517).
"Phenol," in The Merck Index, pp. 1299-1300 (13th Ed., 2001) (Exhibit 2144, filed Sep. 2, 2014 in connection with IPR2013-00517).
Metzker, "Emerging technologies in DNA sequencing" Genome Research, 15:1767-1776, (2005) (Exhibit 2146, filed Sep. 2, 2014 in connection with IPR2013-00517).
Gardner et al., "Rapid incorporation kinetics and improved fidelity of a novel class of 3'-OH unblocked reversible terminators" Nucleic Acids Research, 40:7404-7415 (2012) (Exhibit 2147, filed Sep. 2, 2014 in connection with IPR2013-00517).
Lander et al., "Initial sequencing and analysis of the human genome" Nature, 409:860-921 (2001) (Exhibit 2148, filed Sep. 2, 2014 in connection with 1PR2013-00517).
Aldrich, Fine Chemicals catalogue, p. 1337 (1986) (Exhibit 2150, filed Sep. 2, 2014 in connection with IPR2013-00517).
Sebastian et al., "Dendrimers with N,N-Disubstituted Hydrazines as End Groups, Useful Precursors for the Synthesis of Water-Soluble Dendrimers Capped with Carbohydrate, Carboxylic or Boronic Acid Derivatives" Tetrahedron, 56:6269-6277 (2000) (Exhibit 2151, filed Sep. 2, 2014 in connection with IPR2013-00517).
Reardon et al., "Reduction of 3'-Azido-3'-deoxythymidine (AZT) and AZT Nucleotides by Thiols" The Journal of Biological Chemistry, 269:15999-16008 (1994) (Exhibit 2152, filed Sep. 2, 2014 in connection with IPR2013-00517).
Transcript, Aug. 12, 2014 Deposition of Michael L. Metzker, Ph.D. (Exhibit 2154, filed Sep. 2, 2014 in connection with IPR2013-00517).
Transcript, Aug. 26, 2014 Deposition of Bruce P. Branchaud, Ph.D. (Exhibit 2155, filed.Sep. 2, 2014 in connection with IPR2013-00517).
Petitioner Opposition to Patentee Motion to Exclude Evidence, filed Sep. 15, 2014 in connection with IPR2013-00517.
Patentee Opposition to Petitioner Motion to Exclude Evidence, filed Sep. 15, 2014 in connection with IPR2013-00517.
Patentee's Reply to Petitioner's Opposition to Patentee Motion to Exclude Evidence, filed Sep. 22, 2014 in connection with IPR2013-00517.
Petitioner's Reply to Patentee's Opposition to Motion to Amend, filed Sep. 22, 2014 in connection with IPR2013-00517.
Patentee Demonstratives for Oral Hearing, filed Oct. 3, 2014 in connection with IPR2013-00517.
Petitioner Demonstratives for Oral Hearing, filed Oct. 3, 2014 in connection with IPR2013-00517.
Transcript of Oct. 10, 2014 Oral Hearing, entered Feb. 2, 2015 in connection with IPR2013-00517.
Feb. 11, 2015 Final Written Decision in connection with IPR2013-00517.
Notice of Allowance dated Jun. 23, 2017 by the United States Patent Office in connection with U.S. Appl. No. 15/167,917, Ju et al.
Preliminary Amendment filed on Jul. 12, 2017 in connection with U.S. Appl. No. 15/647,657, Jingyue Ju et al.
Jul. 12, 2017 Office Action issued in connection with U.S. Appl. No. 14/670,748.
Response to Jul. 12, 2017 Office Action filed Aug. 4, 2017 in connection with U.S. Appl. No. 14/670,748.
Oct. 2, 2017 Office Action issued in connection with U.S. Appl. No. 14/670,748.
Response to Oct. 2, 2017 Office Action, including EXhibits 1-2 and Exhibits A-E, filed Mar. 2, 2018 in connection with U.S. Appl. No. 14/670,748.
May 9, 2018 Office Action issued in connection with U.S. Appl. No. 14/670,748.
Response to May 9, 2018 Office Action filed Aug. 9, 2018 in connection with U.S. Appl. No. 14/670,748.
Aug. 9, 2018 Applicant-Initiated Interview Summary issued in connection with U.S. Appl. No. 14/670,748.
Amendment in Response to the Jul. 3, 2017 Summons to Attend Oral Proceedings Pursuant to Rule 115(1) EPC, filed on Mar. 12, 2018 with the European Patent Office in connection with a European counterpart of the subject application, European Patent Application No. EP15195765.1.
Result of Consultation, issued on Mar. 20, 2018 in connection with a European counterpart of the subject application, European Patent Application No. EP15195765.1.
Amendment in Response to the Jul. 3, 2017 Summons to Attend Oral Proceedings Pursuant to Rule 115(1) EPC, filed on Apr. 5, 2018 in connection with a European counterpart of the subject application, European Patent Application No. EP15195765.1.
Petitioner's Reply filed by Illumina, Inc. ("Illumina") on Jan. 22, 2019, in connection with IPR No. IPR2018-00291.
Illumina Updated Exhibit List filed by Illumina on Jan. 22, 2019, in connection with IPR No. IPR2018-00291.
Petitioner's Reply filed by Illumina on Jan. 22, 2019, in connection with IPR No. IPR2018-00318.
Illumina Updated Exhibit List filed by Illumina on Jan. 22, 2019, in connection with IPR No. IPR2018-00318.
Petitioner's Reply filed by Illumina on Jan. 22, 2019, in connection with IPR No. IPR2018-00322.
Illumina Updated Exhibit List filed by Illumina on Jan. 22, 2019, in connection with IPR No. IPR2018-00322.
Petitioner's Reply filed by Illumina on Jan. 22, 2019, in connection with IPR No. IPR2018-00385.

(56) References Cited

OTHER PUBLICATIONS

Illumina Updated Exhibit List filed by Illumina on Jan. 22, 2019, in connection with IPR No. IPR2018-00385.
Petitioner's Reply filed by Illumina on Jan. 22, 2019, in connection with IPR No. IPR2018-00797.
Illumina Updated Exhibit List filed by Illumina on Jan. 22, 2019, in connection with IPR No. IPR2018-00797.
Ruparel et al., "Design and synthesis of a 3'-O-allyl photocleavable fluorescent nucleotide as a reversible terminator for DNA sequencing by synthesis," Proc. Natl. Acad. Sci. USA, 102:5932-5937 (2005) (Exhibit 1093 filed by Illumina in connection with IPRs Nos. IPR2018-00291, IPR2018-00318, IPR2018-00322, IPR2018-00385, and IPR2018-00797).
Genet et al., "Practical Palladium-Mediated Deprotective Method of Allyloxycarbonyl in Aqueous Media," Tetrahedron, 50:497-503 (1994) (Exhibit 1094 filed by Illumina in connection with IPRs Nos. IPR2018-00291, IPR2018-00318, IPR2018-00322, IPR2018-00385, and IPR2018-00797).
IPR2017-02174, Paper 20, Decision Denying Institution of Inter Partes Review (Apr. 20, 2018) (Exhibit 1095 filed by Illumina in connection with IPRs Nos. IPR2018-00291, IPR2018-00318, IPR2018-00322, IPR2018-00385, and IPR2018-00797).
IPR2017-02172, Paper 20, Decision Denying Institution of Inter Partes Review (Apr. 20, 2018) (Exhibit 1096 filed by Illumina in connection with IPRs Nos. IPR2018-00291, IPR2018-00318, IPR2018-00322, IPR2018-00385, and IPR2018-00797).
Nucleic Acids Research publication information for Metzker et al., "Termination of DNA synthesis by novel 3'-modified-deoxyribonucleoside 5'-triphosphates," 22:4259-67. (1994) (Exhibit 1097 filed by Illumina in connection with IPRs Nos. IPR2018-00291, IPR2018-00318, IPR2018-00322, IPR2018-00385, and IPR2018-00797).
IPR2012-00007, Deposition Transcript of Dr. George L. Trainor (Sep. 4-5, 2013) (Exhibit 1098 filed by Illumina in connection with IPRs Nos. IPR2018-00291, IPR2018-00318, IPR2018-00322, IPR2018-00385, and IPR2018-00797).
IUPAC, Nomenclature of Organic Chemistry, Eds. Rigaudy et al., International Union of Pure and Applied Chemistry, Organic Chemistry Division, Commission on Nomenclature of Organic Chemistry, Pergamon Press, 1979 (Exhibit 1099 filed by Illumina in connection with IPRs Nos. IPR2018-00291, IPR2018-00318, IPR2018-00322, IPR2018-00385, and IPR2018-00797).
Jensen and Thor, "Organizations for Standardization of Quantities and Units," Metrologia, 31:503-509 (1994/1995). (Exhibit 1100 filed by Illumina in connections with IPRs Nos. IPR2018-00291, IPR2018-00318, IPR2018-00322, IPR2018-00385, and IPR2018-00797).
Greene and Wuts, "Protective Groups in Organic Synthesis," third edition, John Wiley & Sons (1999) (Exhibit 1101 filed by Illumina in connection with IPRs Nos. IPR2018-00291, IPR2018-00318, IPR2018-00322, IPR2018-00385, and IPR2018-00797).
CRC Handbook of Chemistry and Physics, eds. Weast et al., 72nd edition, CRC Press (1991) (Exhibit 1102 filed by Illumina in connection with IPRs Nos. IPR2018-00291, IPR2018-00318, IPR2018-00322, IPR2018-00385, and IPR2018-00797).
McGraw-Hill Dictionary of Chemistry, ed. Parker, McGraw-Hill Book Co. (1984) (Exhibit 1103 filed by Illumina in connection with IPRs Nos. IPR2018-00291, IPR2018-00318, IPR2018-00322, IPR2018-00385, and IPR2018-00797).
Solomons, "Organic Chemistry", Fourth Edition, John Wiley & Sons (1988) (Exhibit 1104 filed by Illumina in connection with IPRs Nos. IPR2018-00291, IPR2018-00318, IPR2018-00322, IPR2018-00385, and IPR2018-00797).
Morrison et al., "Organic Chemistry," Third Edition, Allyn and Bacon, Inc. (1973) (Exhibit 1105 filed by Illumina in connection with IPRs Nos. IPR2018-00291, IPR2018-00318, IPR2018-00322, IPR2018-00385, and IPR2018-00797).

Cyclist® Exo-Pfu DNA Sequencing Kit, Instruction Manual, Stratagene (1998) (Exhibit 1108 filed by Illumina in connection with IPRs Nos. IPR2018-00291, IPR2018-00318, IPR2018-00322, IPR22018-00385, and IPR2018-00797).
Hedden et al., "DNA Sequence Determination Using Exonuclease-Deficient Pfu DNA Polymerase in a Cycle Sequencing Format," 207th ACS National Meeting, Abstract 121, American Chemical Society, San Diego, CA, Mar. 13-17, 1994 (Exhibit 1109 filed by Illumina in connection with IPRs Nos. IPR2018-00291, IPR2018-00318, IPR2018-00322, IPR2018-00385, and IPR2018-00797).
Transcript for the Deposition of Steven M. Menchen, Jan. 14, 2019, in IPR2018-00291, -00318, -00322, -00385, and -00797 (Exhibit 1112 filed by Illumina in connection with IPRs Nos. IPR2018-00291, IPR2018-00318, IPR2018-00322, IPR2018-00385, and IPR2018-00797).
Transcript for the Deposition of Steven M. Menchen, Jan. 15, 2019, in IPR2018-00291, -00318, -00322, -00385, and -00797 (Exhibit 1113 filed by Illumina in connection with IPRs Nos. IPR2018-00291, IPR2018-00318, IPR2018-00322, IPR2018-00385, and IPR2018-00797).
Jannasch, "Deep Sea Hydrothermal Vents: Underwater Oases," The NEB Transcript 4(1):11-13 (1992) (partial version) (Exhibit 2130 marked in Deposition of Steven M. Menchen, Jan. 15, 2019).
Metzker et al., "Elimination of Residual Natural Nucleotides from 3'-O-Modified-dNTP Syntheses by Enzymatic Mop-Up," BioTechniques, 25:814-817 (1998) (Exhibit 2131 marked in Deposition of Steven M. Menchen, Jan. 15, 2019).
Jannasch, "Deep Sea Hydrothermal Vents: Underwater Oases," The NEB Transcript 4(1):11-13 (1992) (full version) (Exhibit 2132 marked in Deposition of Steven M. Menchen, Jan. 15, 2019).
Lemaire-Audoire et al., "Selective Deprotective Method using Palladium-Water Soluble Catalysts," Tetrahedron Letters, 35:8783-8786 (1994) (Exhibit 1114 filed by Illumina in connection with IPRs Nos. IPR2018-00291, IPR2018-00318, IPR2018-00322, IPR2018-00385, and IPR2018-00797).
Lemaire-Audoire et al., "Chemoselective removal of allylic protecting groups using water-soluble Pd(OAc)$_2$/TPPTS catalyst," Journal of Molecular Catalysis A: Chemical, 116:247-258 (1997) (Exhibit 1115 filed by Illumina in connection with IPRs Nos. IPR2018-00291, IPR2018-00318, IPR2018-00322, IPR2018-00385, and IPR2018-00797).
Qinglin Meng thesis from Dr. Ju's laboratory at Columbia University (2006) (Exhibit 1116 filed by Illumina in connection with IPRs Nos. IPR2018-00291, IPR2018-00318, IPR2018-00322, IPR2018-00385, and IPR2018-00797).
Kutateladze et al., "3'-Hydroxymethyl 2'-deoxynucleoside 5'-triphosphates are inhibitors highly specific for reverse transcriptase," FEBS, 207:205-212 (1986) (Exhibit 1118 filed by Illumina in connection with IPRs Nos. IPR2018-00291, IPR2018-00318, IPR2018-00322, IPR2018-00385, and IPR2018-00797).
Second Declaration of Floyd Romesberg, Ph.D. in Support of Petition for Inter Partes Review in IPR2018-00291, -00318, -00322, -00385, and -00797 (Exhibit 1119 filed by Illumina in connection with IPRs Nos. IPR2018-00291, IPR2018-00318, IPR2018-00322, IPR2018-00385, and IPR2018-00797).
Service, "The Race for the $1000 Genome," Science, 311:1544-46 (2006) (Exhibit 1120 filed by Illumina in connection with IPRs Nos. IPR2018-00291, IPR2018-00318, IPR2018-00322, IPR2018-00385, and IPR2018-00797).
Gardner and Jack, "Determinants of nucleotide sugar recognition in an archaeon DNA polymerase," Nucleic Acids Research, 27:2545-53 (1999) (Exhibit 1122 filed by Illumina in connection with IPRs Nos. IPR2018-00291, IPR2018-00318, IPR2018-00322, IPR2018-00385, and IPR2018-00797).
Kraevskii et al., "Substrate Inhibitors of DNA Biosynthesis," Molecular Biology, 21:25-29 (1987) (Exhibit 1126 filed by Illumina in connection with IPRs Nos. IPR2018-00291, IPR2018-00318, IPR2018-00322, and IPR2018-00385).
IPR2012-00007, Paper 82, Petitioner Illumina's Opposition to Patent Owner Columbia's Motion to Amend (Sep. 27, 2013) (Exhibit 1127 filed by Illumina in connection with IPRs Nos. IPR2018-00291, IPR2018-00318, IPR2018-00322, and IPR2018-00385).

(56) References Cited

OTHER PUBLICATIONS

IPR2012-00007, Paper 83, Petitioner Illumina's Reply to Patent Owner Columbia's Response to Petition (Sep. 27, 2013) (Exhibit 1128 filed by Illumina in connection with IPRs Nos. IPR2018-00291, IPR2018-00318, IPR2018-00322, and IPR2018-00385).
Ju et al., "Four-color DNA sequencing by synthesis using cleavable fluorescent nucleotide reversible terminators," PNAS USA, 103:19635-40 (2006) (Exhibit 1129 filed by Illumina in connection with IPRs Nos. IPR2018-00291, IPR2018-00318, IPR2018-00322, and IPR2018-00385).
Southworth et al., "Cloning of thermostable DNA polymerases from hyperthermophilic marine Archaea with emphasis on *Thermococcus* sp. 9°N-7 and mutations affecting 3'-5' exonuclease activity," PNAS USA, 93:5281-85 (1996) (Exhibit 1133 filed by Illumina in connection with IPRs Nos. IPR2018-00291, IPR2018-00318, IPR2018-00322, and IPR2018-00385).
Takahashi et al., "Palladium-catalyzed Exchange of Allylic Groups of Ethers and Esters with Active Hydrogen Compounds," Bulletin of the Chemical Society of Japan, 45:230-36 (1972). (Exhibit 1134 filed by Illumina in connection with IPRs Nos. IPR2018-00291, IPR2018-00318, IPR2018-00322, and IPR2018-00385).
Yamamoto et al., "Interaction of Palladium(0) Complexes with Allylic Acetates, Allyl Ethers, Allyl Phenyl Chalcogenides, Allylic Alcohols, and Allylamines. Oxidative Addition, Condensation, Disproportionation, and $\pi$-Complex Formation," Organometallics, 5:1559-67 (1986) (Exhibit 1135 filed by Illumina in connection with IPRs Nos. IPR2018-00291, IPR2018-00318, IPR2018-00322, and IPR2018-00385).
Fields, "Methods for Removing the Fmoc Group," Methods in Molecular Biology, vol. 35, Peptide Synthesis Protocols, Chapter 2, Humana Press (1994) (Exhibit 1136 filed by Illumina in connection with IPRs Nos. IPR2018-00291, IPR2018-00318, IPR2018-00322, and IPR2018-00385).
IPR2012-00007, Paper 79, Substitute Columbia Motion to Amend under 37 C.F.R. §42.121 (Filing Authorized to Replace Paper No. 66) (Aug. 30, 2013) (Exhibit 1137 filed by Illumina in connection with IPRs Nos. IPR2018-00291, IPR2018-00318, IPR2018-00322, and IPR2018-00385).
List of documents reviewed by Dr. Romesberg in IPR2018-00291, -00318, -00322, -00385, and -00797 (Exhibit 1138 filed by Illumina in connection with IPRs Nos. IPR2018-00291, IPR2018-00318, IPR2018-00322, IPR2018-00385, and IPR2018-00797).
Patent Owner's Sur-reply filed by The Trustees of Columbia University in the City of New York ("Columbia") on Feb. 5, 2019, in connection with IPRs Nos. IPR2018-00291, IPR2018-00318, IPR2018-00322, and IPR2018-00385.
Patent Owner's Sur-reply filed by Columbia on Feb. 5, 2019, in connection with IPR No. IPR2018-00797.
Columbia's Exhibit List No. 5 Under 37 C.F.R. § 42.63(e) filed by Columbia on Feb. 5, 2019, in connection with IPR No. IPR2018-00291.
Columbia's Exhibit List No. 5 Under 37 C.F.R. § 42.63(e) filed by Columbia on Feb. 5, 2019, in connection with IPR No. IPR2018-00318.
Columbia's Exhibit List No. 5 Under 37 C.F.R. § 42.63(e) filed by Columbia on Feb. 5, 2019, in connection with IPR No. IPR2018-00322.
Columbia's Exhibit List No. 5 Under 37 C.F.R. § 42.63(e) filed by Columbia on Feb. 5, 2019, in connection with IPR No. IPR2018-00385.
Columbia's Exhibit List No. 5 Under 37 C.F.R. § 42.63(e) filed by Columbia on Feb. 5, 2019, in connection with IPR No. IPR2018-00797.
Metzker, et al., "Elimination of Residual Natural Nucleotides from 3'-O-Modified-dNTP Syntheses by Enzymatic Mop-Up," BioTechniques, 25:814-817 (1998) (Marked at Dr. Menchen's Deposition) (Exhibit 2131 filed by Columbia in connection with IPRs Nos. IPR2018-00291, IPR2018-00318, IPR2018-00322, IPR2018-00385, and IPR2018-00797).

Jannasch, "Deep sea hydrothermal vents: underwater oases," The NEB Transcript (1992) (Marked at Dr. Menchen's Deposition) (Exhibit 2132 filed by Columbia in connection with IPRs Nos. IPR2018-00291, IPR2018-00318, IPR2018-00322, IPR2018-00385, and IPR2018-00797).
Transcript for the Deposition of Dr. Floyd Romesberg, Feb. 1, 2019, in IPR2018-00291, -00318, -00322, -00385, and -00797 (Exhibit 2140 filed by Columbia in connection with IPRs Nos. IPR2018-00291, IPR2018-00318, IPR2018-00322, IPR2018-00385, and IPR2018-00797).
Nov. 21, 2018 Office Action issued in connection with U.S. Appl. No. 14/670,748.
Mar. 6, 2014 IPR2012-00007, Paper 140, Final Written Decision (Exhibit 1005 filed by Illumina, Inc. with the Petition for Inter Partes Review, in connection with Case Nos. IPR2018-00291, IPR2018-00318, IPR2018-00322, IPR2018-00385, and IPR2018-00797).
Mar. 6, 2014 IPR2012-00006, Paper 128, Final Written Decision (Exhibit 1006 filed by Illumina, Inc. with the Petition for Inter Partes Review, in connection with Case Nos. IPR2018-00291, IPR2018-00318, IPR2018-00322, IPR2018-00385, and IPR2018-00797).
Mar. 6, 2014 PR2013-00011, Paper 130, Final Written Decision (Exhibit 1007 filed by Illumina, Inc. with the Petition for Inter Partes Review, in connection with Case Nos. IPR2018-00291, IPR2018-00318, IPR2018-00322, IPR2018-00385, and IPR2018-00797).
Jul. 17, 2015 Federal Circuit Opinion Affirming IPR2012-00006, IPR2012-00007 and IPR2013-00011 (Exhibit 1008 filed by Illumina, Inc. with the Petition for Inter Partes Review, in connection with Case Nos. IPR2018-00291, IPR2018-00318, IPR2018-00322, IPR2018-00385, and IPR2018-00797).
Excerpts from Prosecution History of U.S. Pat. No. 9,718,852 ("Ju") (Exhibit 1009 filed by Illumina, Inc. with the Petition for Inter Partes Review, in connection with Case No. IPR2018-00291).
Alberts, et al., "Molecular Biology of the Cell", Third Edition, Garland Publishing Inc., New York (1994) (Exhibit 1011 filed by Illumina, Inc. with the Petition for Inter Partes Review, in connection with Case Nos. IPR2018-00291, IPR2018-00318, IPR2018-00322, IPR2018-00385, and IPR2018-00797).
Declaration of Floyd Romesberg, Ph.D. (Exhibit 1012 filed by Illumina, Inc. with the Petition for Inter Pastes Review, in connection with Case No. IPR2018-00291).
Prober, et al., "A System for Rapid DNA Sequencing with Flourescent Chain-Terminating Dideoxynucleotides", Science, 238:336-341 (1987) ("Prober") (Exhibit 1014 filed by Illumina, Inc. with the Petition for Inter Partes REview, in connection with Case Nos. IPR2018-00291, IPR2018-00318, IPR2018-00322, and IPR2018-00385, and IPR2018-00797).
Metzker, et al., "Termination of DNA synthesis by novel 3'-modified-deoxyribonucleoside 5'-triphosphates", Nucleic Acids Research, 22:4259-67 (1994) ("Metzker") (Exhibit 1016 filed by Illumina, Inc. with the Petition for Inter Partes Review, in connection with Case Nos. IPR2018-00291, IPR2018-00318, IPR2018-00322, IPR2018-00385, and IPR2018-00797).
Wu and Metzker, et al., "Termination of DNA synthesis by N6-alkylated, not 3'-O-alkylated, photocleavable 2'-deoxyadenosine triphosphates", Nucleic Acids Research, 35:6339-6349 (2007) ("Wu and Metzker") (Exhibit 1017 filed by Illumina, Inc. with the Petition for INter Partes Review, in connection with Case Nos. IPR2018-00291, IPR2018-00318, IPR2018-00322, IPR2018-00385, and IPR2018-00797).
Sanger et. al., "DNA sequencing with chain-terminating inhibitors", Proc. Natl. Acad. Sci. USA, 74:5463-5467 (1977) ("Sanger") (Exhibit 1018 filed by Illumina, Inc. with the Petition for Inter Partes Review, in connection with Case Nos. IPR2018-00291, IPR2018-00318, IPR2018-00322, IPR2018-00385, and IPR2018-00797).
Pelletier, et al., "Structures of Ternary Complexes of Rat DNA Polymerase β, a DNA Template-Primer, and ddCTP", Science, 264:1891-1903 (1994) ("Pelletier") (Exhibit 1021 filed by Illumina, Inc. with the Petition for Inter Partes Review, in connection with Case Nos. IPR2018-00291, IPR2018-00318, IPR2018-00322, IPR2018-00385, and IPR2018-00797).

(56) References Cited

OTHER PUBLICATIONS

Declaration of Jingyue Ju from Prosecution History of U.S. Pat. No. 9,718,852 ("Ju") (Exhibit 1022 filed by Illumina, Inc. with the Petition for Inter Partes Review, in connection with Case No. IPR2018-00291).
Welch, et al., "Syntheses of Nucleosides Designed for Combinatorial DNA Sequencing", Chem. Eur. J., 5:951-960 (1999) ("Welch") (Exhibit 1023 filed by Illumina, Inc. with the Petition for Inter Partes Review, in connection with Case Nos. IPR2018-00291, IPR2018-00318, IPR2018-00322, IPR2018-00385, and IPR2018-00797).
Welch, et al., "Corrgenda—Syntheses of Nucleosides Designed for Combinatorial DNA Sequencing", Chem. Eur. J., 11:7136-7145 (2005) ("Welch Corrigenda") (Exhibit 1024 filed by Illumina, Inc. with the Petition for Inter Partes Review, in connection with Case Nos. IPR2018-00291, IPR2018-00318, IPR2018-00322, IPR2018-00385, and IPR2018-00797).
Seela, et al., "7-Deazapurine containing DNA", Nucleic Acids Research, 20:55-61 (1991) ("Seela 1991") (Exhibit 1025 filed by Illumina, Inc. with the Petition for Inter Partes Review, in connection with Case Nos. IPR2018-00291, IPR2018-00385, and IPR2018-00797).
Rosenblum, et al., "New dye-labeled terminators for improved DNA sequencing patterns", Nucleic Acid Research, 25:4500-4504 (1997) ("Rosenblum") (Exhibit 1027 filed by Illumina, Inc. with the Petition for Inter Partes Review, in connection with Case Nos. IPR2018-00291, IPR2018-00318, IPR2018-00322, IPR2018-00385, and IPR2018-00797).
Excerpts from Sep. 4, 2013 Deposition Transcript of Dr. George L. Trainor in IPR2012-00007 (Exhibit 1028 filed by Illumina, Inc. with the Petition for Inter Partes Review, in connection with Case Nos. IPR2018-00291, IPR2018-00318, IPR2018-00322, IPR2018-00385, and IPR2018-00797).
Ramzaeva, et al., "88. 7-Substituted 7-Deasa-2'-deoxyguanosines: Regioselective Halogenation of Pyrrolo[2,3-d] pyrimidine Nucleosides", Helvetica Chimica Acta, 78:1083-1090 (1995) ("Ramzaeva 1995") (Exhibit 1030 filed by Illumina, Inc. with the Petition for Inter Partes Review, in connection with Case Nos. IPR2018-00291, IPR2018-00385, and IPR2018-00797).
Seela, et al., "Oligonucleotide Duplex Stability Controlled by the 7-Substituents of 7-Deazaguanine Bases", Bioorganic & Mechanical Chemistry Letters, 5:3049-3052 (1995) ("Seela 1995") (Exhibit 1031 filed by Illumina, Inc. with the Petition for Inter Partes Review, in connection with Case Nos. IPR2018-00291, IPR2018-00318, IPR2018-00322, IPR2018-00385, and IPR2018-00797).
Seela, et al., "Duplex Stability of Oligonucleotides Containing 7-Substituted 7-Deaza- and 8-Aza-7-Deazapurine Nucleosides", Nucleosides, Nucleosides & Nucleotides, 16:963-966 (1997) ("Seela 1997") (Exhibit 1032 filed by Illumina, Inc. with the Petition for Inter Partes Review, in connection with Case Nos. IPR2018-00291, IPR2018-00385, and IPR2018-00797).
Ramzaeva, et al., "123. 7-Deazaguanine DNA: Oligonucleotides with Hydrophobic or Cationic Side Chains", Helvetica Chimica Acta, 80:1809-1822 (1997) ("Ramzaeva 1997") (Exhibit 1033 filed by Illumina, Inc. with the Petition for Inter Partes Review, in connection with Case Nos. IPR2018-00291, IPR2018-00385, and IPR2018-00797).
Jun. 25, 2013 Declaration of Dr. George L. Trainor from IPR2012-00006 (Exhibit 1034 filed by Illumina, Inc. with the Petition for Inter Partes Review, in connection with Case Nos. IPR2018-00291, IPR2018-00318, IPR2018-00322, IPR2018-00385, and IPR2018-00797).
Boss, et al., "Cleavage of Allyl Ethers with Pd/C", Angew. Chem. Int. Ed. Engl., 15:558-559 (1976) ("Boss") (Exhibit 1035 filed by Illumina, Inc. with the Petition for Inter Partes Review, in connection with Case Nos. IPR2018-00291, IPR2018-00318, IPR2018-00322, IPR2018-00385, and IPR2018-00797).
Qian, et al., "Unexptected Ensymatic Fucosylation of the Hindered Tertiary Alcohol of 3-C-Methyl-N-Acetyllactosamine Produces a Novel Analogue of the LeX-Trisaccharide", Journal of the American Chemical Society, 120:2184-2185 (1998) ("Qian") (Exhibit 1036 filed by Illumina, Inc. with the Petition for Inter Partes Review, in connection with Case Nos. IPR2018-00291, IPR2018-00318, IPR2018-00322, IPR2018-00385, and IPR2018-00797).
Kamal, et al., "A Miled and Rapid Regeneration of Alcohols from their Allylic Ethers by Chlorotrimethylsilane/Sodium Iodide", Tetrahedron Letters, 40:371-372 (1999) ("Kamal") (Exhibit 1037 filed by Illumina, Inc. with the Petition for Inter Partes Review, in connection with Case Nos. IPR2018-00291, IPR2018-00318, IPR2018-00322, IPR2018-00385, and IPR2018-00797).
Excerpts from Prosecution History of U.S. Pat. No. 9,725,480 ("Ju") (Exhibit 1038 filed by Illumina, Inc. with the Petition for Inter Partes Review, in connection with Case Nos. IPR2018-00291, IPR2018-00318, and IPR2018-00322).
Vollhardt, et al., "Organic Chemistry", Second Edition, W.H. Freeman and Co., New York (1994) ("Vollhardt") (Exhibit 1039 filed by Illumina, Inc. with the Petition for Inter Partes Review, in connection with Case Nos. IPR2018-00291, IPR2018-00318, IPR2018-00322, IPR2018-00385, and IPR2018-00797).
Yu, et al., "Cyanine dye dUTP analogs for enzymatic labeling of DNA probes", Nucleic Acids Research, 22:3226-3232 (1994) ("Yu") (Exhibit 1040 filed by Illumina, Inc. with the Petition for Inter Partes Review, in connection with Case Nos. IPR2018-00291, IPR2018-00318, IPR2018-00322, IPR2018-00385, and IPR2018-00797).
Livak, et al., "Detection of single base differences using biotinylated nucleotides with very long linker arms", Nucleic Acids Research, 20:4831-4837 (1992) ("Livak") (Exhibit 1041 filed by Illumina, Inc. with the Petition for Inter Partes Review, in connection with Case Nos. IPR2018-00291, IPR2018-00318, IPR2018-00322, IPR2018-00385, and IPR2018-00797).
Watson, et al., "Genetical Implication of the Structure of Deoxyribonucleic Acid", Nature, 171:964-967 (1953) ("Watson & Crick") (Exhibit 1042 filed by Illumina, Inc. with the Petition for Inter Partes Review, in connection with Case Nos. IPR2018-00291, IPR2018-00318, IPR2018-00322, IPR2018-00385, and IPR2018-00797).
Zavgorodny, et al., "1-Alkylthioalkylation of Nucleoside Hydroxyl Functions and its Synthetic Applications: A New Versatile Method in Nucleoside Chemistry", Tetrahedron Letters, 32:7593-7596 (1991) ("Zavgorodny") (Exhibit 1043 filed by Illumina, Inc. with the Petition for Inter Partes Review, in connection with Case Nos. IPR2018-00291, IPR2018-00318, IPR2018-00322, IPR2018-00385, and IPR2018-00797).
Feb. 11, 2015 Final Written Decision in IPR2013-00517 (Exhibit 1044 filed by Illumina, Inc. with the Petition for Inter Partes Review, in connection with Case Nos. IPR2018-00291, IPR2018-00318, IPR2018-00322, IPR2018-00385, and IPR2018-00797).
May 9, 2016 Federal Circuit Opinion Affirming IPR2013-00517 (Exhibit 1045 filed by Illumina, Inc. with the Petition for Inter Partes Review, in connection with Case Nos. IPR2018-00291, IPR2018-00318, IPR2018-00322, IPR2018-00385, and IPR2018-00797).
Gigg, et al., "The Allyl Ether as a Protecting Group in Carbohydrate Chemistry Part II", J. Chem. Soc. (C), 1903-1911 (1968) ("Gigg") (Exhibit 1046 filed by Illumina, Inc. with the Petition for Inter Partes Review, in connection with Case Nos. IPR2018-00291, IPR2018-00318, IPR2018-00322, IPR2018-00385, and IPR2018-00797).
Aug. 30, 2013 Substitute Columbia Patent Owner Response in IPR2012-00007, Paper 77 (Exhibit 1047 filed by Illumina, Inc. with the Petition for Inter Partes Review, in connection with. Case Nos. IPR2018-00291, IPR2018-00318, IPR2018-00322, IPR2018-00385, and IPR2018-00797).
Jul. 25, 2014 Final Written Decision in IPR2013-00128, Paper 92 (Exhibit 1048 filed by Illumina, Inc. with the Petition for Inter Partes Review, in connection with Case Nos. IPR2018-00291, IPR2018-00318, IPR2018-00322, IPR2018-00385, and IPR2018-00797).
Oct. 28, 2014 Final Written Decision in IPR2013-00266, Paper 73 (Exhibit 1049 filed by Illumina, Inc. with the Petition for Inter

(56) References Cited

OTHER PUBLICATIONS

Partes Review, in connection with Case Nos. IPR2018-00291, IPR2018-00318, IPR2018-00322, IPR2018-00385, and IPR2018-00797).

Jan. 29, 2016 Federal Circuit Opinion Affirming IPR2013-00128 and IPR2013-00266 (Exhibit 1050 filed by Illumina, Inc. with the Petition for Inter Partes Review, in connection with Case Nos. IPR2018-00291, IPR2018-00318, IPR2018-00322, IPR2018-00385, and IPR2018-00797).

Greenberg, et al., "Optimization and Mechanistic Analysis of Oligonucleotide Cleavage from Palladium-Labile Solid-Phase Synthesis Supports", J. Org. Chem., 63:4062-4068 (1998) ("Greenberg") (Exhibit 1051 filed by Illumina, Inc. with the Petition for Inter Partes Review, in connection with Case Nos. IPR2018-00291, IPR2018-00318, IPR2018-00322, IPR2018-00385, and IPR2018-00797).

Seitz, et al., HYCRON, an Allylic Anchor for High-Efficiency Solid Phase Synthesis of Protected Peptides and Glycopeptides, J. Org. Chem., 62:813-826 (1997) ("Seitz") (Exhibit 1052 filed by Illumina, Inc. with the Petition for Inter Partes Review, in connection with Case Nos. IPR2018-00291, IPR2018-00318, IPR2018-00322, IPR2018-00385, and IPR-2018-00797).

Gullier, et al., "Linkers and Cleavage Strategies in Solid-Phase Organic Synthesis and Combinatorial Chemistry", Chem. Rev., 100:2091-2157 (2000) ("Gullier") (Exhibit 1053 filed by Illumina, Inc. with the Petition for Inter Partes Review, in connection with Case Nos. IPR2018-00291, IPR2018-00318, IPR2018-00322, IPR2018-00385, and IPR2018-00797).

Stryer, "Biochemistry", Fourth Edition, W. H. Freeman and Co., New York (1995) ("Stryer") (Exhibit 1055 filed by Illumina, Inc. with the Petition for Inter Partes Review, in connection with Case Nos. IPR2018-00291, IPR2018-00318, IPR2018-00322, IPR2018-00385, and IPR2018-00797).

Columbia's complaint for U.S. Pat. No. 9,718,852 and U.S. Pat. No. 9,719,139 (Exhibit 1056 filed by Illumina, Inc. with the Petition for Inter Partes Review, in connection with Case Nos. IPR2018-00291 and IPR2018-00318).

Curriculum Vitae of Floyd Romesberg, Ph.D. (Exhibit 1057 filed by Illumina, Inc. with the Petition for Inter Partes Review, in connection with Case Nos. IPR2018-00291, IPR2018-00318, IPR2018-00322, IPR2018-00385, and IPR2018-00797).

List of documents considered by Floyd Romesberg, Ph.D. (Exhibit 1058 filed by Illumina, Inc. with the Petition for Inter Partes Review, in connection with Case Nos. IPR2018-00291, IPR2018-00318, IPR2018-00322, and IPR2018-00385).

Sears, et al., "CircumVent Thermal Cycle Sequencing and Alternative Manual and Automated DNA Sequencing Protocols Using the Highly Thermostable VentR (exo) DNA Polymerase", BioTechniques, 13:626-633 (1992) ("Sears") (Exhibit 1059 filed by Iiumina, Inc. with the Petition for Inter Partes Review, in connection with Case Nos. IPR2018-00291, IPR2018-00318, IPR2018-00322, IPR2018-00385, and IPR2018-00797).

Columbia's complaint for U.S. Pat. No. 9,708,358 (Exhibit 1060 filed by Illumina, Inc. with the Petition for Inter Partes Review, in connection with Case No. IPR2018-00322).

Columbia's complaint for U.S. Pat. No. 9,725,480 (Exhibit 1061 filed by Illumina, Inc. with the Petition for Inter Partes Review, in connection with Case No. IPR2018-00385).

Excerpts from Prosecution History of U.S. Pat. No. 9,719,139 (Exhibit 1062 filed by Illumina, Inc. with the Petition for Inter Partes Review, in connection with Case No. IPR2018-00318).

Declaration of Jingyue Ju from Prosecution History of U.S. Pat. No. 9,719,139 (Exhibit 1063 filed by Illumina, Inc. with the Petition for Inter Partes Review, in connection with Case No. IPR2018-00318).

Declaration of Floyd Romesberg, Ph.D. for '139 (Exhibit 1064 filed by Illumina, Inc. with the Petition for Inter Partes Review, in connection with Case No. IPR2018-00318).

Excerpts from Prosecution History of U.S. Pat. No. 9,708,358 (Exhibit 1065 filed by Iiumina, Inc. with the Petition for Inter Partes Review, in connection with Case No. IPR2018-00322).

Declaration of Jingyue Ju from Prosecution History of U.S. Pat. No. 9,708,358 (Exhibit 1066 filed by Illumina, Inc. with the Petition for Inter Partes Review, in connection with Case No. IPR2018-00322).

Declaration of Floyd Romesberg, Ph.D. for '358 (Exhibit 1067 filed by Illumina, Inc. with the Petition for Inter Partes Review, in connection with Case No. IPR2018-00322).

Excerpts from Prosecution History of U.S. Pat. No. 9,725,480 ("Ju") (Exhibit 1068 filed by Illumina, Inc. with the Petition for Inter Partes Review, in connection with Case Nos. IPR2018-00385 and IPR2018-00797).

Declaration of Jingyue Ju from Prosecution History of U.S. Pat. No. 9,725,480 ("Ju") (Exhibit 1069 filed by Illumina, Inc. with the Petition for Inter Partes Review, in connection with Case No. IPR2018-00385).

Declaration of Dr. Floyd Romesberg, Ph.D. for '480 (Exhibit 1070 filed by Illumina, Inc. with the Petition for Inter Partes Review, in connection with Case No. IPR2018-00385).

Excerpts from Prosecution History of U.S. Pat. No. 9,718,852 ("Ju") (Exhibit 1072 filed by Illumina, Inc. with the Petition for Inter Partes Review, in connection with Case Nos. IPR2018-00385 and IPR2018-00797).

Excerpts from Prosecution History of U.S. Pat. No. 9,719,139 ("Ju") (Exhibit 1073 filed by Illumina, Inc. with the Petition for Inter Partes Review, in connection with Case Nos. IPR2018-00385 and IPR2018-00797).

Excerpts from Prosecution History of U.S. Pat. No. 9,708,358 ("Ju") (Exhibit 1074 filed by Illumina, Inc. with the Petition for Inter Partes Review, in connection with Case Nos. IPR2018-00385 and IPR2018-00797).

Excerpts from Prosecution History of U.S. Pat. No. 9,868,985 (Exhibit 1076 filed by Illumina, Inc. with the Petition for Inter Partes Review, in connection with Case No. IPR2018-00797).

Declaration of Jingyue Ju from Prosecution History of U.S. Pat. No. 9,868,985 (Exhibit 1077 filed by Illumina, Inc. with the Petition for Inter Partes Review, in connection with Case No. IPR2018-00797).

Declaration of Floyd Romesberg, Ph.D. for '985 (Exhibit 1078 filed by Illumina, Inc. with the Petition for Inter Partes Review, in connection with Case No. IPR2018-00797).

List of documents considered by Floyd Romesberg, Ph.D. (Exhibit 1079 filed by Illumina, Inc. with the Petition for Inter Partes Review, in connection with Case No. IPR2018-00797).

English translation of Anazawa with affidavit (Exhibit 1084 filed by Illumina, Inc. with the Petition for Inter Partes Review, in connection with Case No. IPR2018-00797).

Columbia's complaint for U.S. Pat. No. 9,868,985 (Exhibit 1086 filed by Illumina, Inc. with the Petition for Inter Partes Review, in connection with Case No. IPR2018-00797).

Sep. 16, 2012 Petition for Inter Partes Review of U.S. Pat. No. 7,790,869.

Sep. 17, 2012 Motion to Waive Page Limit and Proposed Petition in connection with Petition for Inter Partes Review of U.S. Pat. No. 7,790,869.

Dec. 21, 2012 Preliminary Response under 37 C.F.R. 42.107 in connection with IPR2012-00007.

Mar. 12, 2013 Decision on Petition for Inter Partes Review in connection with IPR2012-00007.

Mar. 26, 2013 Request for Reconsideration in connection with IPR2012-00007.

Mar. 26, 2013 Request for Rehearing under 37 C.F.R. 42.71 of Decision to Institute Inter Partes Review in connection with IPR2012-00007.

Apr. 26, 2013 Opposition to Request for Reconsideration (Rehearing) Under 37 C.F.R. 42.71.(C) in connection with IPR2012-00007.

May 10, 2013 Decision on Request for Rehearing in connection with IPR2012-00007.

Aug. 30, 2013 Substitute Patent Owner Response Under 37 C.F.R. 42.120 in connection with IPR2012-00007.

Aug. 30, 2013 Substitute Patent Owner Motion to Amend Under 37 C.F.R. 42.121 in connection with IPR2012-00007.

Sep. 27, 2013 Petitioner Opposition to Motion to Amend in connection with IPR2012-00007.

Sep. 27, 2013 Petitioner Reply to Response to Petition in connection with IPR2012-00007.

(56) References Cited

OTHER PUBLICATIONS

Nov. 18, 2013 Substitute Patent Owner Reply on Motion to Amend in connection with IPR2012-00007.
Excerpts of File History of U.S. Pat. No. 7,790,869 (Exhibit 1022, filed Sep. 16, 2012 in connection with IPR2012-00007).
Sep. 27, 2013 Declaration of Kevin Burgess (Exhibit 1053, filed Sep. 27, 2013 in connection with IPR2012-00007).
Composition of a Nucleotide (Exhibit 2001, filed Dec. 21, 2012 in connection with IPR2012-00007).
Jun. 25, 2013 Substitute Declaration of Dr. George L. Trainor [redacted] (Exhibit 2033, filed Aug. 30, 2013 in connection with IPR2012-00007).
Nov. 26, 2013 Petitioner's Response to Motion for Observations in connection with IPR2012-00007.
Nov. 26, 2013 Patent Owner's Opposition to Petitioner's Motion to Exclude in connection with IPR2012-00007.
Nov. 26, 2013 Petitioner's Opposition to Motion to Exclude in connection with IPR2012-00007.
Dec. 3, 2013 Petitioner Reply to Patent Owner's Opposition to Motion to Exclude in connection with IPR2012-00007.
Dec. 3, 2013 Patent Owner Reply on Motion to Exclude in connection with IPR2012-00007.
Mar. 6, 2014 Final Written Decision in connection with IPR2012-00007.
Krečmerová (1990) "Synthesis of 5'-O-Phosphonomethyl Derivatives of Pyrimidine 2'-Deoxynucleosides." Coll. Czech. Chem. Commun., 55:2521-2536.
Kurata et al. (2001) "Fluorescent quenching-based quantitative detection of specific DNA/RNA using BODIPY® FL-labeled probe of primer," Nucleic Acids Research, vol. 29, No. 6, p. e34.
Kvam et al., (1994) "Characterization of singlet oxygen-induced guanine residue damage after photochemical treatment of free nucleosides and DNA," Biochemica et Biophysica Acta., 1217:9-15.
Lee, L.G., et al. (1992) "DNA sequencing with dye labeled terminators and T7 DNA polymerase effect of dyes and dNTPs on incorporation of dye terminators and probability analysis of termination fragments," Nucleic Acids Res. 20:2471-2483.
Lee L.G. et al, (1997) "New energy transfer dyes for DNA sequencing," Nucleic Acids Res. 25:2816-2822.
Leroy, E.M. et al. (2000) "Diagnosis of Ebola Haemorrhagic Fever by RT-PCR in an Epidemic Setting," Journal of Medical Virology 60:463-467.
Lewis et al. (2002) "Click Chemistry in Situ: Acetylcholinesterase as a Reaction Vessel for the Selective Assembly of a Femtomolar Inhibitor from an Array of Building Blocks," Angew. Chem. Int. Ed. 41(6):1053-1057.
Li, J. (1999) "Single Oligonucleotide Polymorphism Determination Using Primer Extension and Time-of-Flight Mass Spectrometry," Electrophoresis 20:1258-1265.
Li et al. (2003) "A photocleavable Fluorescent Nucleotide for DNA Sequencing and Analysis," PNAS 100(2):414-419.
Liu, H. et al. (2000) "Development of Multichannel Devices with an Array of Electrospray Tips for High-Throughput Mass Spectrometry," Anal. Chem. 72:3303-3310.
Loubinoux, B. et al. "Protection Des Phenols Par Le Groupement Azidomethylene Application A La Synthese De Phenols Instables," Tetrahedron, 1998, 44(19): 6055 (English Abstract Only).
Lu, G. and Burgess, K. (2006) "A Diversity Oriented Synthesis of 3'-O-Modified Nucleoside Triphosphates for DNA 'Sequencing by Synthesis'" Bioorg. Med. Chem. Lett., 16:3902-3905.
Lyamichev, V. et al. (1999) "Polymorphism Identification and Quantitative Detection of Genomic DNA by Invasive Cleavage of Oligonucleotide Probes," Nat. Biotech 17:292-296.
Maier et al. (1995) "Synthesis and Properties of New Fluorescein-Labeled Oligonucleotides," Nucleosides and Nucleotides, 14:961-965.
Margulies, M.; Egholm, M.; Altman, W. E.(2005) "Genome Sequencing in Microfabricated High-Density Picolitre Reactors." Nature, 437:376-380.

Markiewicz et al. (1997) "A new method of synthesis of fluorescently labeled oligonucleotides and their application in DNA sequencing," Nucleic Acids Research, 25:3672-3690.
Marquez et al. (2003) "Selective Fluorescence Quenching of 2,3-Diazabicyclo[2.2.2]oct-2-ene by Nucleotides," Organic Letters, 5:3911-3914.
Mathews C.K. et al. (1985) "Chemical Synthesis of Oligonucleotides," Biochemistry, 2nd Edition, pp. 127-128.
Meng et al. (2006) "Design and Synthesis of a Photocleavable Fluorescent Nucleotide 3'-O-Allyl-dGTP-PC-Biodipy-FL-510 as a Reversible Terminator for DNA Sequencing by Synthesis," J. Org. Chem 71:3248-3252.
Metzker, M.L. et al. (1994) "Termination of DNA synthesis by novel 3' modified deoxyribonucleoside 5' triphosphates," Nucleic Acids Res. 22: 4259-4267.
Metzker M.L. (2005) "Emerging Technologies in DNA Sequencing." Genome Res., 15:1767-1776.
Mitra, R. D.; Shendure J.; Olejnik, J.; et al. (2003) "Fluorescent in situ sequencing on polymerase colonies." Anal. Biochem. 320:55-65.
Monforte, J.A. and Becker, C.H. (1997) "High-throughput DNA analysis by time-of-flight mass spectrometry," Nat. Med. 3(3):360-362.
Nazarenko et al. (2002) "Effect of primary and secondary structure of oligodeoxyribonucleotides on the fluorescent properties of conjugated dyes," Nucleic Acids Research, 30:2089-2095.
Nickel et al. (1992) "Interactions of Azidothymidine triphosphate with the Cellular DNA polymerases alpha, delta, and episilon and with DNA Primase," J. Biol. Chem. 267(2):848-854.
Nielsen et al. (2004) "Multiplexed Sandwich Assays in Microarray Format," Journal of Immunological Methods, vol. 290, pp. 107-120.
Nishino et al. (1991) "Efficient Deanilidation of Phosphoranilidates by the Use of Nitrites and Acetic Anhydride." Heteroatom Chemistry, vol. 2, pp. 187-196.
Olejnik, J. et al. (1995) "Photocleavable biotin derivatives: a versatile approach for the isolation of biomolecules," Proc. Natl. Acad. Sci. USA. 92:7590-7594.
Olejnik, J. et al. (1999) "Photocleavable peptide DNA conjugates: synthesis and applications to DNA analysis using MALDI MS," Nucleic Acids Res. 27:4626-4631.
Pastinen et al. (1997) "Minisequencing: A Specific Tool for DNA Analysis and Diagnostics on Oligonucleotide Arrays," Genomic Res., 7:606-614.
Pelletier, H. et al. (1994) "Structures of ternary complexes of rat DNA polymerase β, a DNA template-primer, and ddCTP," Science 264:1891-1903.
Prober, J.M. et al. (1987) "A system for rapid DNA sequencing with fluorescent chain-terminating dideoxynucleotides," Science 238:336-341.
Quaedflieg et al. (1992) "An Alternative Approach Toward the Synthesis of (3'→5') Methylene Acetal Linked Dinucleosides." Tetrahedron Letters, vol. 33, pp. 3081-3084.
Rao et al. (2001) "Four Color FRET Dye Nucleotide Terminators for DNA Sequencing," Nucleosides, Nucleotides and Nucleic Acids, 20:673-676.
Rasolonjatovo et al. (1998) "6-N-(N-Methylanthranylamido)-4-Oxo-Hexanoic Acid: A New Fluorescent Protecting Group Applicable to a New DNA Sequencing Method," Nucleosides and Nucleotides, 17:2021-2025.
Ronaghi, (1998) "PCR-Introduced Loop Structure as Primer in DNA Sequencing." BioTechniques, 25:876.
Ronaghi, M., Uhlen, M., and Nyren, P. (1998) "A Sequencing Method Based on Real-time Pyrophosphate," Science 281:364-365.
Rosenblum, B. B. et al. (1997) "New dye-labeled terminators for improved DNA sequencing patterns," Nucleic Acids Res. 25:4500-4504.
Roskey, M.T., Juhasz, P., Smirnov, I.P., Takach, E.J., Martin, S.A., and Haff, L.A. (1996) "DNA sequencing by delayed extraction-matrix-assisted laser desorption/ionization time of flight mass spectrometry," Proc. Natl. Acad. Sci. USA. 93:4724-4729.

(56) References Cited

OTHER PUBLICATIONS

Ross, P. L. et al. (1997) "Discrimination of Single-Nucleotide Polymorphisms in Human DNA Using Peptide Nucleic Acid Probes Detected by MALDI-TOF Mass Spectrometry," Anal. Chem. 69:4197-4202.

Ross, P. et al. (1998) High Level Multiplex Genotyping by MALDI-TOF Mass Spectrometry. Nat. Biotech 16:1347-1351.

Ruparel et al. (2005) "Design and Synthesis of a 3'-O-Allyl Photocleavable Fluorescent Nucleotide as a Reversible Terminator for DNA Sequencing by Synthesis," PNAS 102(17):5932-5937.

Sarfati et al., (1995) "Synthesis of fluorescent derivatives of 3'-O-(6-aminohexanoyl)-pyrimidine nucleosides 5'-triphosphates that act as DNA polymerase substrates reversibly tagged at C-3'," JCS Perkin Trans, 1163-1171.

Saxon, E. and Bertozzi, C.R. (2000) "Cell surface engineering by a modified Staudinger reaction," Science 287:2007-2010.

Schena, M., Shalon, D. and Davis, R. Brown P.O. (1995) "Quantitative monitoring of gene expression patterns with a cDNA microarray," Science 270: 467-470.

Seeger (1998) "Single Molecule Fluorescence: High-Performance Molecular Diagnosis and Screening," Bioforum, Git Verlag, Darmstadt, DE vol. 21, (German text).

Seo et al. (2003) "Click Chemistry to Construct Fluorescent Oliginucleotides for DNA Sequencing," J. Org. Chem. 68: 609-612.

Seo et al. (2004) "Photocleavable Fluorescent Nucleotides for DNA Sequencing on a Chip Constructed by Site-Specific Coupling Chemistry," PNAS 101(15):5488-5493.

Seo et al. (2005) "Four-Color DNA Sequencing by Synthesis on a Chip Using Photocleavable Fluorescent Nucleotides," PNAS 102(17):5926-593.

Shendure, J.; Porreca, G. J.; Reppas, N.B.; et al. (2005) "Accurate Multiplex Polony Sequencing of an Evolved Bacterial Genome." Science 309:1728-1732.

Smith, L.M., Sanders, J.Z., Kaiser, R.J., et al. (1986) "Fluorescence Detection in Automated DNA Sequence Analysis," Nature 321:674-679.

Speicher, M.R., Ballard, S.G., and Ward, D.C. (1996) "Karyotyping human chromosomes by combinatorial multi-fluor FISH," Nature Genetics 12: 368-375.

Stoerker, J. et al. (2000) "Rapid Genotyping by MALDI-monitored nuclease selection from probe Libraries," Nat. Biotech 18:1213-1216.

Tang, K., Fu, D.J., Julien, D., Braun, A., Cantor, C.R., and Koster, H. (1999) "Chip-based genotyping by mass spectrometry," Proc. Natl. Acad. Sci. USA. 96:10016-10020.

Tong, X. and Smith, L.M. (1992) "Solid-Phase Method for the Purification of DNA Sequencing Reactions," Anal. Chem. 64:2672-2677.

Torimura et al. (2001) "Fluorescence-Quenching Phenomenon by Photoinduced Electron Transfer between a Fluorescent Dye and Nucleotide Base," Analytical Sciences, 17:155-160.

Tuncel et al. (1999) "Catalytically Self-Threading Polyrotaxanes," Chem. Comm. 1509-1510.

Veeneman et al. (1991) "An Efficient Approach to the Synthesis of Thymidine Derivatives containing Phosphate-Isosteric Methylene Acetyl Linkages," Tetrahedron, 47:1547-1562.

Wada et al. (2001) "2-(Azidomethyl)benzoyl as a new protecting group in nucleosides," Tetrahedron Letters, 42:1069-1072.

Weiss (1999) "Fluorescent Spectroscopy of Single Biomolecules." Science, 283:1676.

Welch et al. (1999) "Synthesis of Nucleosides Designed for Combinatorial DNA Sequencing," Chemistry, European Journal, 5:951-960.

Welch MB, Burgess K, (1999) "Synthesis of fluorescent, photolabile 3'-O-protected nucleoside triphosphates for the base addition sequencing scheme," Nucleosides and Nucleotides 18:197-201.

Wendy, Jen. Et al. (2000) "New Strategies for Organic Catalysis: The First Enantioselective Orgacnocatalytic 1,3-Dipolar Cycloaddition," J. Am. Chem. Soc. 122:9874-9875.

Woolley, A. T. et al. (1997) "High-Speed DNA Genotyping Using Microfabricated Capillary Array Electrophoresis Chips," Anal. Chem. 69:2181-2186.

Yamashita et al. (1987) "Studies on Antitumor Agents VII. Antitumor Activities of O-Alkoxyalkyl Derivatives of 2'-Deoxy-5-trifluoromethyluridine." Chem Pharm. Bull., vol. 35, pp. 2373-2381.

Zavgorodny, S. et al. (1991) "1-Alkylthioalkylation of Nucleoside Hydroxyl Functions and Its synthetic Applications: A New Versatile Method in Nucleoside Chemistry," Tetrahedron Letters, 32(51): 7593-7596.

Zavgorodny et al. (2000) "S,X-Acetals in Nucleoside Chemistry. III. Synthesis of 2'- and 3'-O-Azidomethyl Derivatives of Ribonucleosides" Nucleosides, Nucleotides and Nucleic Acids, 19(10-12):1977-1991.

Zhang et al. (2002) "Synthesis of Releasable Electrophore Tags for Applications in Mass Spectrometry," Bioconjugate Chem., vol. 13, pp. 1002-1012.

Zhu, Z., Chao, J., Yu, H, et al. (1994) "Directly Labeled DNA Probes Using Fluorescent Nucleotides with Different Length Linkers," Nucleic Acids Res., 22:3418-3422.

Sanger et al. (1977) DNA sequencing with chain-terminating inhibitors, Proc. Natl. Acad. Sci. USA. 74:5463-5467 (Exhibit 2025, filed Jun. 24, 2013 in connection with IPR2012-00006).

Pennisi (2000) DOE Team Sequences Three Chromosomes, Science. 288:417-419 (Exhibit 2026, filed Jun. 24, 2013 in connection with IPR2012-00006).

Welch and Burgess (1999) Synthesis of Fluorescent, Photolabile 3'-O-Protected nucleoside Triphosphates for the Base Addition Sequencing Scheme, nucleosides & Nucleotides. 18:197-201 (Exhibit 2027, filed Jun. 24, 2013 in connection with IPR2012-00006).

Hyman (1998) A New Method, of Sequencing DNA, Analytical Biochemistry 174:423-436 (Exhibit 2028, filed Jun. 24, 2013 in connection with IPR2012-00006).

Canard and Sarfati (1994) DNA polymerase fluorescent, substrates with reversible 3'-tags, Gene. 148:1-6 (Exhibit 2030, filed Jun. 24, 2013 in connection with IPR2012-00006).

Sarfati et al. (1987) Synthesis of Fluorescent or Biotinylated Nucleoside Compounds, Tetrahedron Letters. 43:3491-3497 (Exhibit 2032, filed Jun. 24, 2013 in connection with IPR2012-00006).

Jun. 25, 2013 Substitute Declaration of Dr. George L. Trainor [redacted] (Exhibit 2033, filed Aug. 30, 2013 in connection with IPR2012-00006).

Jingyue Ju et. al. (2006) Four-color DNA sequencing by synthesis using cleavable fluorescent nucleotide reversible terminators, Proceedings of the National Academy of Sciences. 103: 19635-19640 (Exhibit 2034, filed Jun. 25, 2013 in connection with IPR2012-00006).

Batista et al. (2008) PRG-1 and 21U-RNAs Interact to Form the piRNA Complex Required for Fertility in C. elegans. Molecular Cell 31:1-12 (Exhibit 2035, filed Jun. 25, 2013 in connection with IPR2012-00006).

Form 7 Review Context and Analysis, Biomedical Engineering and Research to Aid Persons with Disabilities Programs Dec. 19-20, 2000 Panel Review, Fluorescence Imaging Chip System for Massive Parallel DNA Sequencing. Proposal No. BES-0097793 (Exhibit 2036, filed Jun. 25, 2013 in connection with IPR2012-00006).

Oct. 1, 2006 Request for opinion on manuscript by J. Ju et. al., Proceedings of National Academy of Sciences, U.S.A. (Exhibit 2037, filed Jun. 25, 2013 in connection with IPR2012-00006).

Correspondence between George Rupp, Chancellor, Columbia University and Richard T. Schlossberg, President, The David and Lucile Packard Foundation (2001) (Exhibit 2038, filed Jun. 25, 2013 in connection with IPR2012-00006).

The David and Lucile Packard Foundation, Packard Fellowships for Science and Engineering, http://www.packard.org/what-wefund/conservation-and-science/packard-fellowships-for-science-andengineering/ (last visited Jun. 25, 2013) (Exhibit 2039, filed Jun. 25, 2013 in connection with IPR2012-00006).

"Chemistry for Next-Generation Sequencing." http://www.illumina.com/technology/sequencing_technology.ilmn (Exhibit 2040, filed Jun. 25, 2013 in connection with IPR2012-00006).

(56) References Cited

OTHER PUBLICATIONS

Chiang et al. (2010) Mammalian microRNAs: experimental evaluation of novel and previously annotated genes, Genes & Dev. 24:992, 993 (Exhibit 2041, filed Jun. 25, 2013 in connection with IPR2012-00006).
Seo et al. (2004) Photocleavable fluorescent nucleotides for DNA sequencing on a chip constructed by site-specific coupling chemistry, Proc. Natl Acad. Sci. 101(15):5488-5493, (Exhibit 2042, filed Jun. 25, 2013 in connection with IPR2012-00006).
Curriculum vitae of Mr. Raymond S. Sims (Exhibit 2043, filed Jun. 25, 2013 in connection with IPR2012-00006).
Prior Testimony of Mr. Raymond S. Sims (Exhibit 2044, filed Jun. 25, 2013 in connection with IPR2012-00006).
Documents reviewed by Mr. Raymond S. Sims in this Proceeding (Exhibit 2045, filed Jun. 25, 2013 in connection with IPR2012-00006).
Gary Schroth Proof of Chiang Paper (Exhibit 2052, filed Jun. 25, 2013 in connection with IPR2012-00006).
Information about Dr. Ju's intellectual property sent to Illumina (Exhibit 2074, filed Jun. 25, 2013 in connection with IPR2012-00006).
IPR Default Protective Order (Exhibit 2090, filed Jun. 26, 2013 in connection with IPR2012-00006).
Declaration of Raymond S. Sims (Exhibit 2091, filed Jun. 26, 2013 in connection with IPR2012-00006).
Rough Transcript of the Sep. 4, 2013 deposition of Dr. George L. Trainor (Exhibit 2092, filed Oct. 10, 2013 in connection with IPR2012-00006).
Excerpt from Protective Groups in Organic Synthesis, 3rd Ed. (Theodora W. Greene and Peter G.M. Wuts ed., John Wiley & Sons, Inc. 1999) (Exhibit 2093, filed Oct. 1, 2013 in connection with IPR2012-00006).
Final transcript of the Sep. 4-6, 2013 deposition of Dr. George L. Trainor (Exhibit 2094, filed Oct. 1, 2013 in connection with IPR2012-00006).
Final transcript of the Sep. 3, 2013 deposition of Raymond S. Sims (Exhibit 2095, filed Oct. 1, 2013 in connection with IPR2012-00006).
Nov. 12, 2013 Petitioner Motion to Exclude Evidence in connection with IPR2012-00006.
Videotaped Deposition Transcript of Kevin Burgess, Ph.D., Oct. 28, 2013, signed with errata (Exhibit 1056, filed Nov. 19, 2013 in connection with IPR2012-00006).
Nov. 12, 2013 Patent Owner Motion for Observations on the Cross-Examination Testimony of Kevin Burgess, Ph.D. in connection with IPR2012-00006.
Nov. 12, 2013 Patent Owner Motion to Exclude Evidence in connection with IPR2012-00006.
Welch, M., et al (2005) Corrigenda to Syntheses of Nucleosides Designed for Combinatorial DNA Sequencing Chem. Eur.J., 1999, 951-960. Published in Chem. Eur. J, 2005, 11, 7136-7145 (Exhibit 2099, filed Nov. 12, 2013 in connection with IPR2012-00006).
Welch, M (1999) "Base Additions Sequencing Scheme (BASS) and Studies Toward New Sequencing Methodologies." PhD. Dissertation, Texas A&M University (Exhibit 2100, filed Nov. 12, 2013 in connection with IPR2012-00006).
Lu and Burgess (2006) "A Diversity Oriented Synthesis of 3'-O-modified nucleoside triphosphates for DNA 'Sequencing by Synthesis'." Bioorganic & Medicinal Chemistry Letters, 16, 3902-3905 (Exhibit 2101, filed Nov. 12, 2013 in connection with IPR2012-00006).
Advanced Sequencing Technology Awards 2004. http://www.genome.gov/12513162 (accessed Oct. 14, 2013) (Exhibit 2102, filed Nov. 12, 2013 in connection with IPR2012-00006).
Welch and Burgess (2006) Erratum to Synthesis of Fluorescent, Photolabile 3'-O-Protected Nucleoside Triphosphates for the Base Addition Sequencing Scheme, Nucleosides & Nucleotides,18:197-201. Published in Nucleosides, Nucleotides and Nucleic Acids, 25:1, 119 (Exhibit 2013, filed Nov. 12, 2013 in connection with IPR2012-00006).

Nov. 26, 2013 Petitioner Response to Motion for Observations in connection with IPR2012-00006.
Nov. 26, 2013 Patent Owner Opposition to Petitioner's Motion to Exclude in connection with IPR2012-00006.
Nov. 26, 2013 Petitioner Opposition to Motion to Exclude in connection with IPR2012-00006.
Dec. 3, 2013 Petitioner Reply to Patent Owner's Opposition to Motion to Exclude in connection with IPR2012-00006.
Dec. 3, 2013 Patent Owner Reply on Motion to Exclude in connection with IPR2012-00006.
Columbia's Demonstratives Under 42.70(b) for Dec. 17, 2013 Oral Hearing in connection with IPR2012-00006, IPR2012-00007, and IPR2013-00011 (Exhibit 2105, filed Dec. 15, 2013 in connection with IPR2012-00006).
Illumina's Invalidity Demonstratives for Final Hearing Dec. 17, 2013 in connection with IPR2012-00006, IPR2012-00007, and IPR2013-00011 (Exhibit 1057, filed Dec. 16, 2013 in connection with IPR2012-00006).
Feb. 10, 2014 Record of Dec. 17, 2013 Oral Hearing in connection with IPR2012-00006, IPR2012-00007, and IPR2013-00011.
Mar. 6, 2014 Final Written Decision in connection with IPR2012-00006.
Office Action dated Sep. 21, 2007 in connection with U.S. Appl. No. 10/380,256.
Office Action dated Oct. 25, 2002 in connection with U.S. Appl. No. 09/972,364.
Office Action dated Mar. 14, 2003 in connection with U.S. Appl. No. 09/972,364.
Office Action dated Dec. 20, 2006 in connection with U.S. Appl. No. 10/702,203.
Amendment filed May 21, 2007 in response to Office Action dated Dec. 20, 2006 in connection with U.S. Appl. No. 10/702,203.
Notice of Allowance dated Sep. 6, 2007 in connection with U.S. Appl. No. 10/702,203.
Office Action dated Jun. 24, 2008 in connection with U.S. Appl. No. 11/894,690.
Amendment filed Oct. 16, 2008 in response to Office Action dated Jun. 24, 2008 in connection with U.S. Appl. No. 11/894,690.
Supplemental Amendment filed Jan. 16, 2009 in connection with U.S. Appl. No. 11/894,690.
Notice of Allowance dated Feb. 24, 2009 in connection with U.S. Appl. No. 11/894,690.
Office Action dated Jun. 5, 2009 in connection with U.S. Appl. No. 11/894,690.
Nov. 5, 2009 Amendment in response to Office Action dated Jun. 5, 2009 in connection with U.S. Appl. No. 11/894,690.
Office Action dated Sep. 3, 2008 in connection with U.S. Appl. No. 11/894,808.
Dec. 19, 2008 Amendment in response to Office Action dated Sep. 3, 2008 in connection with U.S. Appl. No. 11/894,808.
Amendment after Notice of Allowance filed Jun. 23, 2009 in connection with U.S. Appl. No. 11/894,808.
Office Action dated Jul. 10, 2009 in connection with U.S. Appl. No. 11/810,509.
Jan. 11, 2010 Amendment in response to Office Action dated Jul. 10, 2009 in connection with U.S. Appl. No. 11/810,509.
Jan. 26, 2010 Supplemental Amendment in connection with U.S. Appl. No. 11/810,509.
Notice of Allowance and Fee(s) Due dated Apr. 2, 2010 in connection with U.S. Appl. No. 11/810,509.
Office Action dated Oct. 28, 2010 in connection with U.S. Appl. No. 12/804,284.
Office Action dated Feb. 4, 2011 in connection with U.S. Appl. No. 12/804,284.
Aug. 4, 2011 Amendment in response to Office Action dated Feb. 4, 2011 in connection with U.S. Appl. No. 12/804,284.
Notice of Allowance dated Sep. 1, 2011 in connection with U.S. Appl. No. 12/804,284.
Office Action dated May 8, 2012 in connection with U.S. Appl. No. 13/339,089.
Notice of Abandonment dated Sep. 13, 2013 in connection with U.S. Appl. No. 13/672,437.

(56) References Cited

OTHER PUBLICATIONS

Office Action dated Dec. 1, 2014 in connection with U.S. Appl. No. 13/959,660.
Amendment filed Feb. 27, 2015 in connection with U.S. Appl. No. 13/959,660.
Notice of Allowance dated May 3, 2015 in connection with U.S. Appl. No. 13/959,660.
Official Action dated Mar. 17, 2009 in connection with Canadian Patent Application No. CA 2425112 OA.
Sep. 17, 2009 Response to Official Action dated Mar. 17, 2009 in connection with Canadian Patent Application No. CA 2425112 OA.
Official Action dated Mar. 16, 2010 in connection with Canadian Patent Application No. CA 2425112 OA.
Sep. 16, 2010 Response to Official Action dated Mar. 16, 2010 in connection with Canadian Patent Application No. CA 2425112 OA.
Partial European Search Report dated Apr. 26, 2007 in connection with European Patent Application No. 07004522.4.
Extended European Search Report dated Jul. 18, 2007 in connection with European Patent Application No. 07004522.4.
Official Action dated Mar. 14, 2008 in connection with European Patent Application No. 07004522.4.
Sep. 24, 2008 Response to Official Action dated Mar. 14, 2008 in connection with European Patent Application No. 07004522.4.
Communication Pursuant to Article 94(3) EPC dated Apr. 30, 2009 in connection with counterpart European Patent Application No. 07004522.4.
Nov. 10, 2009 Response to Communication Pursuant to Article 94(3) EPC dated Apr. 30, 2009 in connection with counterpart European Patent Application No. 07004522.4.
Communication Pursuant to Article 94(3) EPC dated Jun. 10, 2012 in connection with counterpart European Patent Application No. 07004522.4.
Oct. 20, 2010 Response to Communication Pursuant to Article 94(3) EPC dated Jun. 10, 2012 in connection with counterpart European Patent Application No. 07004522.4.
Communication Pursuant to Article 94(3) EPC issued Apr. 1, 2011 in connection with counterpart European Patent Application No. 07004522.4.
Oct. 11, 2011 Response to Communication Pursuant to Article 94(3) EPC dated Apr. 1, 2011 in connection with counterpart European Patent Application No. 07004522.4.
Communication Pursuant to Article 94(3) EPC dated May 24, 2012 in connection with counterpart European Patent Application No. 07004522.4.
Nov. 30, 2012 Response to Communication Pursuant to Article 94(3) EPC dated May 24, 2012 in connection with counterpart European Patent Application No. 07004522.4.
Communication Pursuant to Article 94(3) EPC dated Jun. 12, 2013 in connection with counterpart European Patent Application No. 07004522.4.
Dec. 31, 2013 Response to Communication Pursuant to Article 94(3) EPC dated Jun. 12, 2013 in connection with counterpart European Patent Application No. 07004522.4.
Jul. 9, 2014 Communication accompanying Summons to Attend Oral Proceedings in connection with counterpart European Patent Application No. 07004522.4.
Jan. 2, 2015 Written Submission in connection with counterpart European Patent Application No. 07004522.4.
Jan. 15, 2015 Communication in connection with counterpart European Patent Application No. 07004522.4.
Jan. 29, 2015 Written Submission in connection with counterpart European Patent Application No. 07004522.4.
Feb. 5, 2015 Communication in connection with counterpart European Patent Application. No. 07004522.4.
Mar. 23, 2015 Decision of Refusal in connection with counterpart European Patent Application No. 07004522.4.
Jun. 1, 2015 Notice of Appeal in connection with counterpart European Patent Application No. 07004522.4.
Aug. 3, 2015 Statement of Grounds of Appeal in connection with counterpart European Patent Application No. 07004522.4.
International Search Report dated May 13, 2002 in connection with PCT/US01/31243.
European Search Report dated Feb. 27, 2004 in connection with European Patent Application No. 01977533.7.
Supplementary European Search Report dated Feb. 16, 2004 in connection with European Patent Application No. 01977533.
Communication Pursuant to Article 94(3) EPC dated Mar. 30, 2005 in connection with European Patent Application No. 01977533.7.
Oct. 10, 2005 Response to Communication Pursuant to Article 94(3) EPC dated Mar. 30, 2005 in connection with European Patent Application No. 01977533.7.
Communication Pursuant to Article 94(3) EPC dated Nov. 16, 2005 in connection with European Patent Application No. 01977533.7.
Mar. 22, 2006 Response to Communication Pursuant to Article 94(3) EPC dated Nov. 16, 2005 in connection with European Patent Application No. 01977533.7.
International Preliminary Examination Report dated Jun. 13, 2003 in connection with PCT/US01/31243.
Official Action dated Mar. 31, 2006 in connection with European Patent Application No. 01968905.8.
Official Action dated May 21, 2007 in connection with European Patent Application No. 01968905.8.
International Preliminary Examination Report dated Feb. 25, 2003 in connection with PCT/US01/28967.
Supplementary European Search Report dated Jun. 7, 2005 in connection with European Patent Application No. 01968905.
International Search Report dated Jan. 23, 2002 in connection with PCT/US01/28967.
European Search Report dated May 18, 2016 in connection with European Patent Application No. EP15195765.1, Ju et al.
Notification of Transmittal of International Search Report and the Written Opinion of the International Searching Authority, or the Declaration dated Sep. 9, 2008 in connection with International Application No. PCT/US06/24157.
Notification of Transmittal of International Search Report and Written Opinion, dated Feb. 6, 2008 in connection with International Application No. PCT/06/042739.
Notification Concerning Transmittal of International Preliminary Report on Patentability dated May 15, 2008 in connection with International Application No. PCT/US2006/042698.
Notification of Transmittal of the International Search Report and Written Opinion, dated Aug. 12, 2008 in connection with International Application No. PCT/US07/24646.
Office Action dated Nov. 14, 2007 in connection with U.S. Appl. No. 10/735,081.
Office Action dated Jul. 8, 2008 in connection with U.S. Appl. No. 10/591,520.
Restriction Requirement dated Oct. 1, 2007 in connection with U.S. Appl. No. 10/521,206.
Jun. 4, 2013 Petition for Inter Partes Review of U.S. Pat. No. 7,057,026.
J. Meinwald, An Approach to the Synthesis of Pederin, 49 Pure and Appl. Chem. 1275 (1977) (Exhibit 1004, filed Jun. 4, 2013 in connection with IPR2013-00324).
Takeshi Matsumoto et al., A Revised Structure of Pederin, 60 Tetrahedron Letters 6297 (1968) (Exhibit 1005, filed Jun. 4, 2013 in connection with IPR2013-00324).
Jun. 4, 2013 Declaration of Dr. Bruce Branchaud (Exhibit 1009, filed Jun. 4, 2013 in connection with IPR2013-00324).
Excerpts from the '026 Patent File History (Exhibit 1010, filed Jun. 4, 2013 in connection with IPR2013-00324).
Excerpts from the file history of European Patent Application No. 02781434.2 (Exhibit 1011, filed Jun. 4, 2013 in connection with IPR2013-00324).
Nov. 21, 2013 Decision Denying Institution of Inter Partes Review of U.S. Pat. No. 7,057,026 in connection with IPR2013-00324.
*Trustees of Columbia University in the City of New York v. Illumina, Inc.*, Nos. 2014-1547, 2014-1548, and 2014-1550 (Fed. Cir. Jul. 17, 2015).
*Illumina Cambridge Ltd. v. Intelligent Bio-Systems, Inc.*, Nos. 167. 2015-1123 and 2015-1243 (Fed. Cir. Jan. 29, 2016).
*Intelligent Bio-Systems, Inc. v. Illumina Cambridge Ltd.*, No. 2015-1693 (Fed. Cir. May 9, 2016).

(56) References Cited

OTHER PUBLICATIONS

Declaration of Michael Metzker in Opposition to Plaintiffs' Motion for Preliminary Injunction, Illumina, Inc. v. Qiagen, N.V., No. 3:16-cv-02788-WHa (N.D. Cal. Jul. 25, 2016)(Doc. 76), first made publicly available Aug. 25, 2016.
Notice of Motion to Stay Injunction Pending Appeal or, Alternatively, Pending Decision by the Federal Circuit on Stay Pending Appeal, Illumina, Inc. v. Qiagen, N.V., No. 3:16-cv-02788-WHA (N.D. Cal. Sep. 15, 2016)(Doc. 122) (Redacted Version of Document Sought to be Sealed), first made publicly available Sep. 22, 2016.
Sep. 23, 2016 Response to May 24, 2016 Communication Pursuant to Article 94(3) EPC filed with the European Patent Office in connection with European Patent Application No. 15195765.1.
Petition for Inter Partes Review of U.S. Pat. No. 9,718,852, filed by Illumina, Inc. Dec. 8, 2017, in connection with Case No. IPR2018-00291.
Declaration of Floyd Romesberg, Ph.D., filed by Illumina, Inc. Dec. 8, 2017 with the Petition for Inter Partes Review of U.S. Pat. No. 9,718,852, in connection with Case No. IPR2018-00291.
Petition for Inter Partes Review of U.S. Pat. No. 9,719,139, filed by Illumina, Inc. Dec. 15, 2017, in connection with Case No. IPR2018-00318.
Declaration of Floyd Romesberg, Ph.D., filed by Illumina, Inc. Dec. 15, 2017 with the Petition for Inter Partes Review of U.S. Pat. No. 9,719,139, in connection with Case No. IPR2018-00318.
Petition for Inter Partes Review of U.S. Pat. No. 9,708,358, filed by Illumina, Inc. Dec. 18, 2017, in connection with Case No. IPR2018-00322.
Declaration of Floyd Romesberg, Ph.D., filed by Illumina, Inc. Dec. 18, 2017 with the Petition for Inter Partes Review of U.S. Pat. No. 9,708,358, in connection with Case No. IPR2018-00322.
Petition for Inter Partes Review of U.S. Pat. No. 9,725,480, filed by Illumina, Inc. Dec. 22, 2017, in connection with Case No. IPR2018-00385.
Declaration of Floyd Romesberg, Ph.D., filed by Illumina, Inc. Dec. 22, 2017 with the Petition for Inter Partes Review of U.S. Pat. No. 9,725,480, in connection with Case No. IPR2018-00385.
Petition for Inter Partes Review of U.S. Pat. No. 9,868,985 filed by Illumina, Inc. Mar. 16, 2018, in connection with Case No. IPR2018-00797.
Declaration of Floyd Romesberg, Ph.D., filed by Illumina, Inc. Mar. 16, 2018 with the Petition for Inter Partes Review of U.S. Pat. No. 9,868,985, in connection with Case No. IPR 2018-00797.
First Office Action dated Jul. 20, 2016 in connection with U.S. Appl. No. 15/167,917, Ju et al.
Applicant-Initiated Interview Summary, dated Nov. 11, 2017 in connection with U.S. Appl. No. 15/167,917, Ju et al.
Second Office Action dated Jan. 4, 2017 in connection with U.S. Appl. No. 15/617,917, Ju et al.
Response to Second Office Action, filed Jan. 10, 2017 in connection with U.S. Appl. No. 15/167,917.
Terminal Disclaimer filed on Jan. 10, 2017 in connection with U.S. Appl. No. 15/167,917, Ju et al.
Third Office Action, dated Mar. 30, 2017 in connection with U.S. Appl. No. 15/167,917, Ju et al.
Response to Mar. 30, 2017 Office Action, filed May 26, 2017 in connection with U.S. Appl. No. 15/617,917, Ju et al.
First Office Action dated Feb. 9, 2017 in connection with U.S. Appl. No. 15/380,270, Ju et al.
Applicant-Initiated Interview Summary, dated Apr. 24, 2017 in connection with U.S. Appl. No. 15/380,270, Ju et al.
Response to Feb. 9, 2017 Office Action, filed May 9, 2017 in connection with U.S. Appl. No. 15/380,270, Ju et al.
Terminal Disclaimer filed on May 9, 2017 in connection with U.S. Appl. No. 15/380,270, Ju et al.
Notice of Allowance, dated May 26, 2017 in connection with U.S. Appl. No. 15/380,270, Ju et al.
First Office Action dated Feb. 8, 2017 in connection with U.S. Appl. No. 15/380,284, Ju et al.
Applicant-Initiated Interview Summary, dated Apr. 25, 2017 in connection with U.S. Appl. No. 15/380,284, Ju et al.
Response to First Office Action, filed May 8, 2017 in connection with U.S. Appl. No. 15/380,284, Ju et al.
Terminal Disclaimer filed on May 8, 2017 in connection with U.S. Appl. No. 15/380,284, Ju et al.
Notice of Allowance, dated May 26, 2017 in connection with U.S. Appl. No. 15/380,284, Ju et al.
First Office Action dated Feb. 10, 2017 in connection with U.S. Appl. No. 15/380,311, Ju et al.
Applicant-Initiated Interview Summary, dated Apr. 25, 2017 in connection with U.S. Appl. No. 15/380,311, Ju et al.
Response to First Office Action, filed May 9, 2017 in connection with U.S. Appl. No. 15/380,311.
Terminal Disclaimer filed on May 9, 2017 in connection with U.S. Appl. No. 15/380,311, Ju et al.
Notice of Allowance, dated May 26, 2017 in connection with U.S. Appl. No. 15/380,311, Ju et al.
Communication Pursuant to Article 94(3) EPC, dated May 24, 2016 in connection with European Patent Application No. 15195765.1.
Sep. 23, 2016 Response to the May 24, 2016 Communication Pursuant to Article 94(3) EPC, issued by the EPO in connections with EP 15195765.1.
Communication Pursuant to Article 94(3) EPC, dated Nov. 10, 2016 in connection with European Patent Application No. 15195765.1.
Mar. 20, 2017 Response to Communication Pursuant to Article 94(3) EPC, dated Nov. 10, 2016 in connection with European Patent Application No. 15195765.1.
Patent Owner Preliminary Response filed by The Trustees of Columbia University in the City of New York Mar. 27, 2018, in connection with Case No. IPR2018-00291.
Patent Owner Preliminary Response filed by The Trustees of Columbia University in the City of New York Apr. 9, 2018, in connection with Case No. IPR2018-00318.
Patent Owner Preliminary Response filed by The Trustees of Columbia University in the City of New York Apr. 9, 2018, in connection with Case No. IPR2018-00322.
Patent Owner Preliminary Response filed by The Trustees of Columbia University in the City of New York May 4, 2018, in connection with Case No. IPR2018-00385.
Patent Owner Preliminary Response filed by The Trustees of Columbia University in the City of New York Jul. 6, 2018, in connection with Case No. IPR2018-00797.
Excerpts from the Prosecution History of U.S. Pat. No. 9,718,852 not included in Ex-1009 (Exhibit 2005 filed by The Trustees of Columbia University in the City of New York with the Patent Owner Preliminary Response, in connection with Case No. IPR2018-00291).
Excerpts from the Prosecution History of U.S. Pat. No. 9,725,480 not included in Ex-1038 (Exhibit 2006 filed by The Trustees of Columbia University in the City of New York with the Patent Owner Preliminary Response, in connection with Case Nos. IPR2018-00291, IPR2018-00318, and IPR2018-00322).
IPR2013-00517, Ex. 2011, Declaration of Floyd Romesberg, Ph.D. (May 5, 2014) (Exhibit 2007 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
IPR2013-00517, Paper 32, Illumina's Patent Owner Response (May 5, 2014) (Exhibit 2008 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
Excerpts from the Ex Parte Reexamination History of U.S. Pat. No. 5,808,045 (Exhibit 2009 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
Assignment data in connection with U.S. Pat. No. 5,808,045 (Exhibit 2010 filed by The Trustees of Columbia University in the City of New York with the Patent Owner Preliminary Response, in con-

(56) References Cited

OTHER PUBLICATIONS nection with Case Nos. IPR2018-00291, IPR2018-00318, IPR2018-00322, IPR2018-00385, and IPR2018-00797).
Metzker, et al., "Elimination of Residual Natural Nucleotides from 3'-O-Modified-dNTP Syntheses by Enzymatic Mop-Up," BioTechniques, 25:814-817 (1998) (Exhibit 2012 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
PCT International Application Publication No. WO 00/53805, ASM Scientific, Inc., published Sep. 14, 2000 ("Stemple") (Exhibit 2013 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
Metzker, et al., "Stop-Start DNA Synthesis in the Base Addition Sequencing Scheme (BASS)," Genome Mapping & Sequencing (1994) (Exhibit 2014 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
Boons, et al., "A New Procedure for the Isomerisation of Substituted and Unsubstituted Allyl Ethers of Carbohydrates," Chemical Communications, 141-142 (1196) (Exhibit 2018 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
Ociai, et al., "Hypervalent (tert-Butylperoxy)iodanes Generate Iodine-Centered Radicals at Room Temperature in Solution: Oxidation and Deprotection on Benzyl and Allyl Ethers, and Evidence for Generation of $\alpha$-Oxy Carborn Radicals," J. Am. Chem. Soc., 118:7716-7730 (1996) (Exhibit 2019 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
Olivero & Dunach, "Nichel-catalysed Electrochemical Reductive Deprotection of Allyl Ethers," J. Chem. Soc., Chem. Commun., 2498-2498 (1995) (Exhibit 2020 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
Excerpts from the Ex Parte Reexamination History of U.S. Pat. No. 6,232,465 (Exhibit 2022 filed by The Trustees of Columbia University in the City of New York with the Patent Owner Preliminary Response, in connection with Case Nos. IPR2018-00291, IPR2018-00318, IPR2018-00322, and IPR2018-00385).
Solexa, Inc.'s Fed. R. Civ. P. 7.1 Statement (Feb. 19, 2010) (Exhibit 2023 filed by The Trustees of Columbia University in the City of New York with the Patent Owner Preliminary Response, in connection with Case Nos. IPR2018-00291, IPR2018-00318, IPR2018-00322, and IPR2018-00385).
Solexa, Inc.'s Schedule 13D-A Submission to the United States Securities and Exchange Commission (Feb. 2, 2007) (Exhibit 2024 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
Litosh, et al., "Improved Nucleotide Selectivity and Termination of 3'-OH Unblocked Reversible Terminators by Molecular Tuning of 2-Nitrobenzyl Alkylated HOMedU Triphosphates," Nucleic Acids Research, 39:1-13 (2011) (Exhibit 2025 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).

IPR2017-02172, Paper 6, Preliminary Response of Patent Owner Illumina Cambridge Ltd. (Jan. 23, 2018) (Exhibit 2026 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
IPR2017-02174, Paper 6, Preliminary Response of Patent Owner Illumine Cambridge Ltd. (Jan. 23, 2018) (Exhibit 2027 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
No. 2015-1123 (CAFC), Brief of Patent Owner-Appellant Illumina Cambridge Ltd., D.I. 27 (Mar. 10, 2015) (Exhibit 2029 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
IPR2013-00266, Paper 39, Patent Owner Illumina's Reply to Petitioner's Opposition to Illumina's Motion to Amend (Mar. 21, 2014) (Exhibit 2030 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
Canard & Sarfati, "DNA Polymerase Fluorescent Substrates with Reversible 3'-Tags," Gene, 148:1-6 (1994) (Exhibit 2031 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
IPR2013-00517, Paper 84, Oral Hearing Transcript (Feb. 2, 2015) (Exhibit 2032 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
IPR2013-00517, Paper 64, Illumina's Motion for Observations on the Cross-Examination Testimony of Bruce Branchaud, Ph.D. and Michael Metzker, Ph.D. (Sep. 2, 2014) (Exhibit 2033 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
IPR2012-00007, Paper 5, Petition for Inter Partes Review of U.S. Pat. No. 7,790,869 (Sep. 16, 2012) (Exhibit 2034 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
IPR2013-00517, Exhibit 1025, Deposition of Floyd Romesberg, Ph.D. (Jul. 8, 2014) (Exhibit 2035 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
IPR2012-00007, Paper 38, Decision on Petition for Inter Partes REview (Mar. 12, 2013) (Exhibit 2036 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
Assignment data in connection with U.S. Patent Application Publication No. 2007-0166705 and U.S. Pat. No. 7,541,444 (Exhibit 2037 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
Assignment data in connection with U.S. Pat. No. 6,232,465 (Exhibit 2038 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
Translation Affidavit for Anazawa (Exhibit 2040 filed by The Trustees of Columbia University in the City of New York with the

(56) References Cited

OTHER PUBLICATIONS

Patent Owner Preliminary Response, in connection with Case Nos. IPR2018-00291, IPR2018-00318, IPR2018-00322, IPR2018-00385, and IPR2018-00797).
Welch & Burgess, "Synthesis of Fluorescent, Photolabile 3'-O-Protected Nucleoside Triphosphates for the Base Addition Sequencing Scheme," Nucleosides & Nucleotides, 18:197-201 (1999) (Exhibit 2041 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
IPR2013-00517, Paper 68, Illuminais Opposition to IBS Motion to Exclude Evidence (Exhibit 2042 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
Excerpts from the Prosecution History of U.S. Pat. No. 7,771,973 (Exhibit 2043 filed by The Trustees of Columbia University in the City of New York with the Patent Owner Preliminary Response, in connection with Case Nos. IPR2018-00291, IPR2018-00318, IPR2018-00322, IPR2018-00385, and IPR2018-00797).
Excerpts from the Prosecution History of U.S. Pat. No. 9,719,139 not included in Ex-1062 (Exhibit 2044 filed by The Trustees of Columbia University in the City of New York with the Patent Owner Preliminary Response, in connection with Case No. IPR2018-00318).
Excerpts from the Prosecution History of U.S. Pat. No. 9,708,358 not included in Ex-1065 (Exhibit 2045 filed by The Trustees of Columbia University in the City of New York with the Patent Owner Preliminary Response, in connection with Case No. IPR2018-00322).
Froehler, et al. "Oligodeoxynucleotides Containing C-5 Propyne Analogs of 2'-Deoxyuridine and 2'-Deoxycytidine," Tetrahedron Letters, 33:5307-5310 (1922) (Exhibit 2046 filed by The Trustees of Columbia University in the City of New York with the Patent Owner Preliminary Response, in connection with Case Nos. IPR2018-00318, IPR2018-00322, and IPR2018-00797).
Excerpts from the Prosecution History of U.S. Pat. No. 9,725,480 not included in Ex-1068 (Exhibit 2047 filed by The Trustees of Columbia University in the City of New York with the Patent Owner Preliminary Response, in connection with Case No. IPR2018-00385).
Excerpts from the Prosecution History of U.S. Pat. No. 9,718,852 not included in Ex-1072 (Exhibit 2048 filed by The Trustees of Columbia University in the City of New York with the Patent Owner Preliminary Response, in connection with Case No. IPR2018-00385).
IPR2018-00291, Petition for Inter Partes Review fo U.S. Pat. No. 9,718,852 (Dec. 8, 2017) (Exhibit 2049 filed by The Trustees of Columbia University in the City of New York with the Patent Owner Preliminary Response, in connection with Case Nos. IPR2018-00385 and IPR2018-00797).
Excerpts from the Prosecution History of U.S. Pat. No. 9,868,985 not included in Ex. 1076 (Exhibit 2051 filed by The Trustees of Columbia University in the City of New York with the Patent Owner Preliminary Response, in connection with Case No. IPR2018-00797).
Declaration of Steven M. Menchen, Ph. D. (Exhibit 2052 filed by The Trustees of Columbia University in the City of New York with the Patent Owner Preliminary Response, in connection with Case No. IPR2018-00797).
Metzker "Sequencing technologies—the next generation," Nature Review, 11(1):31-46 (2010) (Exhibit 2053 filed by The Trustees of Columbia University in the City of New York with the Patent Owner Preliminary Response, in connection with Case No. IPR2018-00797).
Ronaghi, et al. "A Sequencing Method Based on Real-Time Pyrophosphate," Science, 281(5375):363-365 (1998) (Exhibit 2054 filed by The Trustees of Columbia University in the City of New York with the Patent Owner Preliminary Response, in connection with Case No. IPR2018-00797).
Genomeweb, "Illumina Closes Solexa Acquisition," Jan. 26, 2007 (Exhibit 2055 filed by The Trustees of Columbia University in the City of New York with the Patent Owner Preliminary Response, in connection with Case No. IPR2018-00797).
Lee et al., "Unwinding of Double-Stranded DNA Helix by Dehydration," Proc. Natl. Acad. Sci. USA, 78(5):2838-2842 (1981) (Exhibit 2056 filed by The Trustees of Columbia University in the City of New York with the Patent Owner Preliminary Response, in connection with Case No. IPR2018-00797).
Lindahl, "Instability and decay of the primary structure of DNA," Nature, 362:709-715 (1993) (Exhibit 2057 filed by The Trustees of Columbia University in the City of New York with the Patent Owner Preliminary Response, in connection with Case No. IPR2018-00797).
Mozingo, "Palladium Catalysts," Organic Syntheses, Coll. 3:658 (1955) (Exhibit 2058 filed by The Trustees of Columbia University in the City of New York with the Patent Owner Preliminary Response, in connection with Case No. IPR2018-00797).
Johnson, "Rapid Quench Kinetic Analysis of Polymerases, Adenosinetriphosphatases, and Enzyme Intermediates," Methods in Enzymology, 249:38-61 (1995) (Exhibit 2059 filed by The Trustees of Columbia University in the City of New York with the Patent Owner Preliminary Response, in connection with Case No. IPR2018-00797).
IPR2018-00291, Institution Decision, Paper No. 16 (Jun. 25, 2018) (Exhibit 2060 filed by The Trustees of Columbia University in the City of New York with the Patent Owner Preliminary Response, in connection with Case No. IPR2018-00797).
Zielonacka-Lis, "The Acidic Hydrolysis of Nucleosides and Nucleotides," Nucleosides & Nucleotides, 8(3):838-405 (1989) (Exhibit 2061 filed by The Trustees of Columbia University in the City of New York with the Patent Owner Preliminary Response, in connection with Case No. IPR2018-00797).
IPR2013-00128, Ex. 1029, Substitute Declaration of Floyd Romesberg, Ph.D. (Jan. 9, 2014) (Exhibit 2062 filed by The Trustees of Columbia University in the City of New York with the Patent Owner Preliminary Response, in connection with Case No. IPR2018-00797).
IPR2018-00318, Institution Decision, Paper No. 16 (Jul. 3, 2018) (Exhibit 2063 filed by The Trustees of Columbia University in the City of New York with the Patent Owner Preliminary Response, in connection with Case No. IPR2018-00797).
IPR2018-00322, Institution Decision, Paper No. 16 (Jul. 3, 2018) (Exhibit 2064 filed by The Trustees of Columbia University in the City of New York with the Patent Owner Preliminary Response, in connection with Case. No. IPR2018-00797).
Excerpts from the Ex Parte Reexamination History of U.S. Pat. No. 6,232,465 (Exhibit 2065 filed by The Trustees of Columbia University in the City of New York with the Patent Owner Preliminary Response, in connection with Case No. IPR2018-00797).
Curriculum Vitae of Steven M. Menchen, Ph.D. (Exhibit 2066 filed by The Trustees of Columbia University in the City of New York with the Patent Owner Preliminary Response, in connection with Case No. IPR2018-00797).
Decision on Institution of Inter Partes Review Under 35 U.S.C. § 314(a) of U.S. Pat. No. 9,718,852 B2, issued on Jun. 25, 2018 in connection with Case No. IPR2018-00291.
Decision on Institution of Inter Partes Review Under 35 U.S.C. § 314(a) of U.S. Pat. No. 9,719,139 B2, issued on Jul. 3, 2018 in connection with Case No. IPR2018-00318.
Decision on Institution of Inter Partes Review Under 35 U.S.C. § 314(a) of U.S. Pat. No. 9,708,358 B2, issued on Jul. 3, 2018 in connection with Case No. IPR2018-00322.
Decision on Institution of Inter Partes Review Under 35 U.S.C. § 314(a) of U.S. Pat. No. 9,725,480 B2, issued on Jul. 27, 2018 in connection with Case No. IPR2018-00385.
Decision on Institution of Inter Partes Review Under 35 U.S.C. § 314 of U.S. Pat. No. 9,868,985 B2, issued on Sep. 18, 2018 in connection with Case No. IPR2018-00797.

(56) References Cited

OTHER PUBLICATIONS

U.S. Application for a Method for Direct Nucleic Acid Sequencing; U.S. Appl. No. 09/266,187, filed Mar. 10, 1999.
U.S. Appl. No. 90/008,149, filed Aug. 4, 2006, Gitten.
U.S. Appl. No. 90/008,152, filed Aug. 3, 2006, Gitten.
International Search Report dated Sep. 26, 2003 in connection with PCT/US03/21818.
International Preliminary Examination Report dated Mar. 18, 2005 in connection with PCT/US03/21818.
Notification of Transmittal of International Search Report and Written Opinion, dated May 22, 2008 in connection with International Application No. PCT/US06/45180.
International Preliminary Report on Patentability dated Sep. 5, 2006 in connection with PCT/US05/06960.
International Search Report dated Oct. 29, 2007 in connection with PCT International Application No. PCT/US07/13559.
Supplementary European Search Report dated Feb. 9, 2007 in connection with European Patent Application No. 03764568.6.
Supplementary European Search Report dated Sep. 9, 2008 in connection with PCT International Application No. PCT/US05/06960.
International Search Report dated Sep. 18, 2002 in connection with PCT/US02/09752.
International Preliminary Examination Report dated Mar. 17, 2003 in connection with PCT/US02/09752.
Supplementary European Search Report dated May 25, 2005 in connection with European Patent Application No. 02728606.1.
Written Opinion of the International Searching Authority dated Oct. 27, 2005 in connection with PCT/US05/06960.
Written Opinion of the International Searching Authority dated Dec. 15, 2006 in connection with PCT/US05/13883.
International Search Report dated Jun. 8, 2004 in connection with PCT/US03/39354.
International Search Report dated Nov. 4, 2005 in connection with PCT/US05/06960.
International Search Report dated Dec. 15, 2006 in connection with PCT/US05/13883.
Aug. 19, 2013 Petition 2 of 2 for Inter Partes Review of U.S. Pat. No. 7,566,537, issued Aug. 19, 2013.
Aug. 16, 2013 Declaration of Dr. Bruce Branchaud (Exhibit 1015, filed Aug. 19, 2013 in connection with IPR2013-00518).
Excerpts from the '537 Patent file History (Exhibit 1016, filed Aug. 19, 2013 in connection with IPR2013-00518).
Excerpts from the file history of European Patent Application No. 02781434.2 (Exhibit 1017, filed Aug. 19, 2013 in connection with IPR2013-00518).
Feb. 13, 2014 Decision of Institution of Inter Partes Review IPR2013-00518.
May 5, 2014 Patentee Request for Adverse Judgment in IPR2013-00518.
2014 Decision of Adverse Judgment in IPR2013-00518.
U.S. Appl. No. 10/227,131, filed Jun. 5, 2003, Barnes et al.
Jan. 29, 2013 Petition for Inter Partes Review of U.S. Pat. No. 7,057,026.
Feb. 7, 2013 Revised Petition for Inter Partes Review of U.S. Pat. No. 7,057,026.
May 1, 2013 Preliminary Response under 37 C.F.R. 42.107 in connection with IPR2013-00128.
Jul. 29, 2013 Decision on Petition for Inter Partes Review in connection with IPR2013-00128.
Oct. 24, 2013 Patent Owner Motion to Amend the Patent in connection with IPR2013-00128.
Beckman Coulter CEQTM 2000 DNA Analysis System User's Guide, Jun. 2000 (Exhibit 1006, filed Jan. 29, 2013 in connection with IPR2013-00128.
Kamal, Tetrahedron Letters 40(2):371-372, 1999 (Exhibit 1010, filed Jan. 29, 2013 in connection with IPR2013-00128).
Jung, J.C.S. Chem. Comm. (7):315-316, 1978 (Exhibit 1011, filed Jan. 29, 2013 in connection with IPR2013-00128).
Jan. 28, 2013 Declaration of Dr. Bruce Branchaud (Exhibit 1015, filed Jan. 29, 2013 in connection with IPR2013-00128).
Excerpts from the '026 Patent File History (Exhibit 1016, filed Jan. 29, 2013 in connection with IPR2013-00128).
Transcript of Initial Conference Call Held on Aug. 29, 2013 (Exhibit 1020, filed Jan. 29, 2013 in connection with IPR2013-00128).
*The Trustees of Columbia University in the City of New York* v. *Illumina, Inc.*, 1:12-cv-00376-GMS—Columbia's Amended Complaint (Exhibit 2001, filed May 1, 2013 in connection with IPR2013-00128).
*The Trustees of Columbia University in the City of New York* v. *Illumina, Inc.*, 1:12-cv-00376-GMS—Columbia's Amended Answer (Exhibit 2002, filed May 1, 2013 in connection with IPR2013-00128).
*The Trustees of Columbia University in the City of New York* v. *Illumina, Inc.*, 1:12-cv-00376-GMS—IBS's Responses to Illumina's Requests for Admission (Exhibit 2003, filed May 1, 2013 in connection with IPR2013-00128).
*The Trustees of Columbia University in the City of New York* v. *Illumina, Inc.*, 1:12-cv-00376-GMS—Columbia's Response to Illumina's Requests for Admission (Exhibit 2004, filed May 1, 2013 in connection with IPR2013-00128).
Green & Wuts, Protective Groups in Organic Synthesis, excerpts from "Protection From the Hydroxyl Group," (1999) (Exhibit 2006, filed Oct. 24, 2013 in connection with IPR2013-00128).
Katagiri et al., "Selective Protection of the Primary Hydroxyl Groups of Oxetanocin A," Chem. Pharm. Bull. 43:884-886 (1995) (Exhibit 2007, filed Oct. 24, 2013 in connection with IPR2013-00128).
Jan. 9, 2014 Substitute Declaration of Floyd Romesberg, Ph.D. (Exhibit 1029, filed Jan. 24, 2014 in connection with IPR2013-00128).
Oct. 3, 2013 Deposition Transcript of Bruce Branchaud, Ph.D. (Exhibit 2012, filed Oct. 24, 2013 in connection with IPR2013-00128).
Ruby, Methods in Enzymology (1990) (Exhibit 2016, filed Oct. 24, 2013 in connection with IPR2013-00128).
U.S. Pat. No. 7,057,026 file history (Exhibit 2025, filed Oct. 24, 2013 in connection with IPR2013-00128).
Substitute Eric Vermaas Declaration, Dec. 20, 2013 (Exhibit 1025, filed Jan. 24, 2014 in connection with IPR2013-00128).
Excerpts from Protective Groups in Organic Synthesis (Theodora W. Greene & Peter G. M. Wuts eds., John Wiley & Sons, Inc. 3rd ed. 1999) (1991) (Exhibit 1021, filed Dec. 23, 2013 in connection with IPR2013-00128).
Signed Deposition Transcript of Dr. Bruce Branchaud on Oct. 3, 2013 (Exhibit 1022, filed Dec. 23, 2013 in connection with IPR2013-00128).
Jan. 24, 2014 Intelligent Bio-Systems Opposition to Illumina's Motion to Amend in connection with IPR2013-00128.
Dawson et al., "Affinity Isolation of Transcriptionally Active Murine Erythroleukemia Cell DNA Using a Cleavable Biotinylated Nucleotide Analog" J. of Biol. Chem., 264, 12830-37 (1989) (Exhibit 1030, filed Jan. 24, 2014 in with IPR2013-00128).
Mitra et al., "Fluorescent in situ sequencing on polymerase colonies" Analytical Biochem. 320, 55-65 (2003) (Exhibit 1032, filed Jan. 24, 2014 in connection with IPR2013-00128).
Deposition of Floyd Romesberg, Ph.D., from Jan. 14, 2014 (Exhibit 1033, filed Jan. 24, 2014 in connection with IPR2013-00128).
1999/2000 Pierce Chemical Company catalog (1999) (Exhibit 1034, filed Jan. 24, 2014 in connection with IPR2013-00128).
Second Declaration of Dr. Bruce Branchaud, dated Jan. 23, 2014 (Exhibit 1035, filed Jan. 24, 2014 in connection with IPR2013-00128).
Excerpts from the file history of European Patent Application No. 02781434.2 (Exhibit 1039, filed Jan. 24, 2014 in connection with IPR2013-00128).
Lukesh et al., "A Potent, Versatile Disulfide-Reducing Agent from Aspartic Acid" J. Am. Chem. Soc., 134:4057-59 (2012) (Exhibit 1041, filed Jan. 24, 2014 in connection with IPR2013-00128).
Klausner, "DuPont's DNA Sequencer Uses New Chemistry" Nat. Biotech., 5:1111-12 (1987) (Exhibit 1042, filed Jan. 24, 2014 in connection with IPR2013-00128).

(56) References Cited

OTHER PUBLICATIONS

Murakami et al., "Structure of a Plasmodium yoelii gene-encoded protein homologous to the Ca2+-ATPase of rabbit skeletal muscle sarcoplasmic reticulum" J. Cell Sci., 97, 487-95 (1990) (Exhibit 1043, filed Jan. 24, 2014 in connection with IPR2013-00128).
Letsinger et al., "2,4-Dinitrobenzenesulfenyl as a Blocking Group for Hydroxyl Functions in Nucleosides" J. Org. Chem., 29: 2615-2618 (1964) (Exhibit 1044, filed Jan. 24, 2014 in connection with IPR2013-00128).
Handlon & Oppenheimer, "Thiol Reduction of 3'-Azidothymidine to 3'-Aminothymidine: Kinetics and Biomedical Implications" Pharm. Res., 5:297-99 (1988) (Exhibit 1045, filed Jan. 24, 2014 in connection with IPR2013-00128).
Burns et al., "Selective Reduction of Disulfides by Tris(2-carboxyethyl)phosphine" J. Org. Chem., 56:2648-50 (1991) (Exhibit 1047, filed Jan. 24, 2014 in connection with IPR2013-00128).
Feb. 19, 2014 Substitute Motion to Amend Under 37 C.F.R. §42.121 in connection with IPR2013-00128.
Substitute Declaration of Floyd Romesberg, Ph.D., in Support of Patent Owner's Motion to Amend (Exhibit 2009, filed Feb. 19, 2014 in connection with IPR2013-00128).
Substitute Declaration of Eric Vermaas Accompanying Patent Owner's Motion to Amend (Exhibit 2028, filed Feb. 19, 2014 in connection with IPR2013-00128).
Feb. 24, 2014 Patent Owner Illumina's Reply to Petitioner's Opposition to Illumina's Motion to Amend.
Supplementary information for Ex. 1032 (Mitra et al., Analytical Biochem. 320, 55-65, 2003) (Exhibit 2029, filed Feb. 24, 2014 in connection with 1PR2013-00128).
ScanArray Express Line of Microarray Scanners—Brochure (Exhibit 2032, filed Feb. 24, 2014 in connection with IPR2013-00128).
Feb. 11, 2014 Second Deposition Transcript of Bruce Branchadd, Ph.D. (Exhibit 2034, filed Feb. 24, 2014 in connection with IPR2013-00128).
Mullis et al., "Specific Synthesis of DNA in Vitro via a Polymerase-Catalyzed Chain Reaction," pp. 335-350, in Methods in Enzymology, vol. 155, Recombinant DNA, Part F, ed. Wu, Academic Press, Inc., San Diego (1987) (Exhibit 2037, filed Feb. 24, 2014 in connection with IPR2013-00128).
Brown et al., "Modern machine-aided methods of oligodeoxyribonucleotide synthesis," pp. 1-11; and Ruth, "Oligodeoxynucleotides with reporter groups attached to the base," p. 255, in Oligonucleotides and Analogues, A Practical Approach, ed. Eckstein, Oxford Univ. Press, New York (1991) (Exhibit 2038, filed Feb. 24, 2014 in connection with IPR2013-00128).
Dawson and Herman et al., "Affinity isolation of active murine erythroleukemia cell chromatin: Uniform distribution of ubiquitinated histone H2A between active and inactive fractions", Journal of Cellular Biochemistry 46:166-173 (1991) (Exhibit 2039, filed Feb. 24, 2014 in connection with IPR2013-00128).
Rigas et al., "Rapid plasmid library screening using RecA-coated biotinylated probes," PNAS USA 83:9591-9595 (1986) (Exhibit 2040, filed Feb. 24, 2014 in connection with IPR2013-00128).
Westheimer et al., "Why nature chose phosphates" Science 235:1173-1178 (1987) (Exhibit 2042, filed Feb. 24, 2014 in connection with IPR2013-00128).
Mar. 18, 2014 Petitioner's Motion to Exclude in connection with IPR2013-00128.
Petitioner's Objections to Patentee's Exhibits submitted with its Reply to Petitioner's Opposition to Patentee's Motion to Amend (Exhibit 1048, filed Mar. 18, 2014 in connection with IPR2013-00128).
Mar. 18, 2014 Patentee's Motion to Exclude Petitioner's Evidence in connection with IPR2013-00128.
Demonstrative Exhibits of Intelligent Bio-Systems, Inc., for Apr. 23, 2014 hearing, filed Apr. 18, 2014 in connection with IPR2013-00128.
Demonstrative Exhibits of Illumina for Apr. 23, 2014 hearing, filed Apr. 21, 2014 in connection with IPR2013-00128.
May 22, 2014 Record of Apr. 23, 2014 Oral Hearing in connection with IPR2013-00128.
Jul. 25, 2014 Final Written Decision in connection with IPR2013-00128.
Patent Owner Response (PUBLIC version) filed by The Trustees of Columbia University in the City of New York Oct. 26, 2018, in connection with Case Nos. IPR2018-00291, IPR2018-00318, IPR2018-00322, and IPR2018-00385.
Patent Owner Response (PUBLIC version) filed by The Trustees of Columbia University in the City of New York Oct. 26, 2018, in connection with Case No. IPR2018-00797.
Metzker, "Sequencing technologies—the next generation," Nature Review, 11(1):31-46 (2010) (Exhibit 2053 filed by The Trustees of Columbia University in the City of New York with the Patent Owner Response, in connection with Case Nos. IPR2018-00291, IPR2018-00318, IPR2018-00322, and IPR2018-00385).
Ronaghi, et al., "A sequencing method based on real-time pyrophosphate," Science, 281 (5375):363-365 (1998) (Exhibit 2054 filed by The Trustees of Columbia University in the City of New York with the Patent Owner Response, in connection with Case Nos. IPR2018-00291, IPR2018-00318, IPR2018-00322, and IPR2018-00385).
Genomeweb, "Illumina Closes Solexa Acquisition," Jan. 26, 2007 (Exhibit 2055 filed by The Trustees of Columbia University in the City of New York with the Patent Owner Response, in connection with Case Nos. IPR2018-00291, IPR2018-00318, IPR2018-00322, and IPR2018-00385).
Lindahl, "Instability and decay of the primary structure of DNA," Nature, 362:709-715 (1993) (Exhibit 2057 filed by The Trustees of Columbia University in the City of New York with the Patent Owner Response, in connection with Case Nos. IPR2018-00291, IPR2018-00318, IPR2018-00322, and IPR2018-00385).
Johnson, "Rapid Quench Kinetic Analysis of Polymerases, Adenosinetriphosphatases, and Enzyme Intermediates," Methods in Enzymology, 249:38-61 (1995) (Exhibit 2059 filed by The Trustees of Columbia University in the City of New York with the Patent Owner Response, in connection with Case Nos. IPR2018-00291, IPR2018-00318, IPR2018-00322, and IPR2018-00385).
Excerpts from the Ex Parte Reexamination History of U.S. Pat. No. 6,232,465 (Exhibit 2065 filed by The Trustees of Columbia University in the City of New York with the Patent Owner Response, in connection with Case Nos. IPR2018-00291, IPR2018-00318, IPR2018-00322, and IPR2018-00385).
Curriculum Vitae of Steven M. Menchen, Ph.D. (Exhibit 2066 filed by The Trustees of Columbia University in the City of New York with the Patent Owner Response, in connection with Case Nos. IPR2018-00291, IPR2018-00318, IPR2018-00322, and IPR2018-00385).
IPR2013-00128, Exhibit 1033, Deposition of Floyd Romesberg, Ph.D. (Jan. 14, 2014) (Exhibit 2080 filed by The Trustees of Columbia University in the City of New York with the Patent Owner Response, in connection with Case Nos. IPR2018-00291, IPR2018-00318, IPR2018-00322, IPR2018-00385, and IPR2018-00797).
IPR2013-00266, Exhibit 2037, Second Declaration of Floyd Romesberg, Ph.D. (Mar. 21, 2014) (Exhibit 2081 filed by The Trustees of Columbia University in the City of New York with the Patent Owner Response, in connection with Case Nos. IPR2018-00291, IPR2018-00318, IPR2018-00322, IPR2018-00385, and IPR2018-00797).
IPR2013-00266, Exhibit 1042, Deposition of Floyd Romesberg, Ph.D. (Apr. 10, 2014) (Exhibit 2082 filed by The Trustees of Columbia University in the City of New York with the Patent Owner Response, in connection with Case Nos. IPR2018-00291, IPR2018-00318, IPR2018-00322, IPR2018-00385, and IPR2018-00797).
IPR2013-00128, Substitute Exhibit 2009, Substitute Declaration of Floyd Romesberg, Ph.D. in Support of Patent Owner's Motion to Amend (Feb. 19, 2014) (Exhibit 2083 filed by The Trustees of Columbia University in the City of New York with the Patent Owner Response, in connection with Case Nos. IPR2018-00291, IPR2018-00318, IPR2018-00322, IPR2018-00385, and IPR2018-00797).
Jannasch, "Deep sea hydrothermal vents: underwater oases," The NEB Transcript (1992) (Exhibit 2084 filed by The Trustees of Columbia University in the City of New York with the Patent Owner

(56) References Cited

OTHER PUBLICATIONS

Response, in connection with Case Nos. IPR2018-00291, IPR2018-00318, IPR2018-00322, IPR2018-00385, and IPR2018-00797).

Levine, et al. "The relationship of structure to the effectiveness of denaturing agents for deoxyribonucleic acid," Biochem., 2(1):168-175 (1963) (Exhibit 2085 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Kit, "Deoxyribonucleic acids," Annu. Rev. Biochem., 32:43-82 (1963) (Exhibit 2086 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Lindahl & Nyberg, "Rate of Depurination of Native Deoxyribonucleic Acid," Biochem., 11(19):3610-3618 (1972) (Exhibit 2087 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Hamed et al., "Palladium(II)-Catalyzed Oxidation of Aldehydes and Ketones. 1. Carbonylation of Ketones with Carbon Monoxide Catalyzed by Palladium(II) Chloride in Methanol," J. Org. Chem., 66(1):180-185 (2001) (Exhibit 2089 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Exhibit from Deposition of Dr. Floyd Romesberg, Sep. 19-20, 2018, in IPR2018-00291, -00318, -00322, and -00385 (Handwritten calculations) (Exhibit 2090 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Pillai & Nandi, "Interaction of Palladium (II) With DNA," Biochimica et Biophysica Acta, 474:11-16 (1977) (Exhibit 2094 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Transcript for the Deposition of Dr. Floyd Romesberg, Sep. 19-20, 2018, in IPR2018-00291, -00318, -00322, and -00385 (Original Transcript) (Exhibit 2096 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Qian et al., "Chemoenzymatic synthesis of α-(1→3)-Gal(NAc)-terminating glycosides of complex tertiary sugar alcohols," J. Am. Chem. Soc. 121:12063-12072 (1999) (Exhibit 2097 filed by The Trustees of Columbia University in the City of New York with the Patent Owner Response, in connection with Case Nos. IPR2018-00291, IPR2018-00318, IPR2018-00322, IPR2018-00385, and IPR2018-00797).

"Complete reverse regioselection in Wacker oxidation of acetonides and cyclic carbonates of allylic diols," J. Org. Chem. 60:4678-4679 (1995) (Exhibit 2098 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Tsuji, et al., "Regioselective oxidation of internal olefins bearing neighboring oxygen functions by means of palladium catalysts," Tetrahedron Letters, 23(26):2679-2682 (1982) (Exhibit 2101 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Qian, "Enzymatic and Chemical Synthesis of Oligosaccharide Analogs," Thesis, University of Alberta (2000) (Exhibit 2102 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Project Information for Dr. Romesberg NIH Grant, "Evolving Novel Polymerases for Genome Sequencing" (Exhibit 2103 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Genomeweb, "Helicos and Columbia to Test Scripps' Improved Polymerase for Next-Gen Sequencing," Oct. 3, 2006 (Exhibit 2104 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Bieg et al., "Isomerization and clevage of allyl ethers of carbohydrates by trans-[Pd(NH3)2 Cl2]," J. Carbohydrate Chem., 4(3):441-446 (1985) (Exhibit 2105 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Ochiai, "Hypervalent (tert-butylperoxy) iodanes generate iodine-centred radicals at room temperature in solution," J. Am. Chem. Soc., 118:7716-7730 (1996) (Exhibit 2106 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Katritzky, "The origins of the benzotrizole project, its versatility illustrated by a new —C=CHCH+OEt synthon, and novel synthesis of alpha beta-unsaturated aldehydes and ketones, furans, pyrroles and allyl ethers," Synthesis, 1215-1323 (1995) (Exhibit 2107 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Documents Considered by Dr. Menchen for Exhibits 2114 and 2116 (Exhibit 2108 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Martinez et al., "Acyclic nucleoside triphosphate analogs as terminators in biocatalytic DNA replication," Bioorganic & Medicinal Chemistry Letters, 7(23):3013-3016 (1997) (Exhibit 2111 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Hawley's Condensed Chemical Dictionary, Thirteenth Edition (1997) (excerpts) (Exhibit 2112 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Transcript for the Deposition of Dr. Floyd Romesberg, Oct. 9, 2018, in IPR2018-00797 (Exhibit 2113 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Declaration of Steven M. Menchen, Ph.D., Oct. 26, 2018 (IPR2018-00797) (Exhibit 2114 filed by The Trustees of Columbia University in the City of New York with the Patent Owner Response, in connection with Case No. IPR2018-00797).

Parshall, "Homogenous Catalysis, the Applications and Chemistry of Catalysis by Soluble Transition Metal Complexes," John Wiley and Sons (1980) (excerpts) (Exhibit 2115 filed by The Trustees of Columbia University in the City of New York with the Patent Owner Response, in connection with Case Nos. IPR2018-00291, IPR2018-00318, IPR2018-00322, IPR2018-00385, and IPR2018-00797).

Declaration of Steven M. Menchen, Ph.D., Oct. 26, 2018 (IPR2018-00291, -00318, -00322, and -00385) (Exhibit 2116 filed by The Trustees of Columbia University in the City of New York with the Patent Owner Response, in connection with Case Nos. IPR2018-00291, IPR2018-00318, IPR2018-00322, and IPR2018-00385).

(56) References Cited

OTHER PUBLICATIONS

IPR2017-02172, Paper 22, Decision Denying Petitioner's Request for Rehearing (Aug. 2, 2018) (Exhibit 2117 filed by The Trustees of Columbia University in the City of New York with the Patent Owner Response, in connection with Case Nos. IPR2018-00291, IPR2018-00318, IPR2018-00322, IPR2018-00385, and IPR2018-00797).
Dr. Romesberg NIH Grant, "Evolving Novel Polymerases for Genome Sequencing" (Exhibit 2118 filed by The Trustees of Columbia University in the City of New York with the Patent Owner Response, in connection with Case Nos. IPR2018-00291, IPR2018-00318, IPR2018-00322, IPR2018-00385, and IPR2018-00797).
Solexa, Inc.'s Form 425 Submission to the United States Securities and Exchange Commission (Nov. 14, 2006) (Exhibit 2119 filed by The Trustees of Columbia University in the City of New York with the Patent Owner Response, in connection with Case Nos. IPR2018-00291, IPR2018-00318, IPR2018-00322, IPR2018-00385, and IPR2018-00797).
Internal Solexa Email (PUBLIC version) (Exhibit 2120 filed by The Trustees of Columbia University in the City of New York with the Patent Owner Response, in connection with Case Nos. IPR2018-00291, IPR2018-00318, IPR2018-00322, IPR2018-00385, and IPR2018-00797).
Internal Illumina Email (PUBLIC version) (Exhibit 2121 filed by The Trustees of Columbia University in the City of New York with the Patent Owner Response, in connection with Case Nos. IPR2018-00291, IPR2018-00318, IPR2018-00322, IPR2018-00385, and IPR2018-00797).
Internal Illumina Email (PUBLIC version) (Exhibit 2122 filed by The Trustees of Columbia University in the City of New York with the Patent Owner Response, in connection with Case Nos. IPR2018-00291, IPR2018-00318, IPR2018-00322, IPR2018-00385, and IPR2018-00797).
Attachment to Internal Illumina Email (Ex. 2122) (PUBLIC version) (Exhibit 2123 filed by The Trustees of Columbia University in the City of New York with the Patent Owner Response, in connection with Case Nos. IPR2018-00291, IPR2018-00318, IPR2018-00322, IPR2018-00385, and IPR2018-00797).
Attachment to Internal Illumina Email (Ex. 2122) (PUBLIC version) (Exhibit 2124 filed by The Trustees of Columbia University in the City of New York with the Patent Owner Response, in connection with Case Nos. IPR2018-00291, IPR2018-00318, IPR2018-00322, IPR2018-00385, and IPR2018-00797).
Eckert et al., "DNA Polymerase Fidelity and the Polymerase Chain Reaction," Genome Research, 1:17-24 (1991) (Exhibit 2125 filed by The Trustees of Columbia University in the City of New York with the Patent Owner Response, in connection with Case Nos. IPR2018-00291, IPR2018-00318, IPR2018-00322, IPR2018-00385, and IPR2018-00797).
Transcript for the Deposition of Dr. Floyd Romesberg, Sep. 19-20, 2018, in IPR2018-00291, -00318, -00322, and -00385 (Revised Transcript) (Exhibit 2126 filed by The Trustees of Columbia University in the City of New York with the Patent Owner Response, in connection with Case Nos. IPR2018-00291, IPR2018-00318, IPR2018-00322, IPR2018-00385, and IPR2018-00797).
Jul. 18, 2018 Office Action issued in connection with U.S. Appl. No. 15/915,983.
Response to Jul. 18, 2018 Office Action filed Aug. 23, 2018 in connection with U.S. Appl. No. 15/915,983.
Nov. 5, 2018 Final Office Action issued in connection with U.S. Appl. No. 15/915,983.
U.S. Appl. No. 09/266,187, filed Mar. 10, 1999, Stemple et al.
Sep. 16, 2012 Petition for Inter Partes Review of U.S. Pat. No. 7,713,698, issued May 11, 2010.
Sep. 16, 2012 Motion to Waive Page Limit and Proposed Petition in connection with Petition for Inter Partes Review of U.S. Pat. No. 7,713,698, issued May 11, 2010.
Dec. 20, 2012 Preliminary Response under 37 C.F.R. 42.107 in connection with IPR2012-00006.
Mar. 12, 2013 Decision on Petition for Inter Partes Review in connection with IPR2012-00006.
Mar. 26, 2013 Request for Reconsideration in connection with IPR2012-00006.
Apr. 26, 2013 Opposition to Request for Reconsideration (Rehearing) Under 37 C.F.R. 42.71.(C) in connection with IPR2012-00006.
Sep. 27, 2013 Petitioner Opposition to Motion to Amend in connection with IPR2012-00006.
Sep. 27, 2013 Petitioner Reply to Response to Petition in connection with IPR2012-00006.
Nov. 18, 2013 Substitute Patent Owner Reply on Motion to Amend in connection with IPR2012-00006.
Prober et al. (1987), "A System for Rapid DNA Sequencing with Fluorescent Chain-Terminating Dideoxynucleotides", *Science* vol. 238, Oct. 16, 1987, pp. 336-341 (Exhibit 1003, filed Sep. 16, 2012 in connection with IPR2012-00006).
Sep. 15, 2012 Declaration of George Weinstock Under Rule 37 C.F.R. §1.132 (Exhibit 1021, filed Sep. 16, 2012 in connection with IPR2012-00006).
Excerpts of File History of U.S. Pat. No. 7,713,698 (Exhibit 1022, filed Sep. 16, 2012 in connection with IPR2012-00006).
Columbia's Amended Complaint from *The Trustees of Columbia University in the City of New York v. Illumina, Inc.*, D. Del C.A. No. 12-376 (GMS), filed Apr. 11, 2012 (Exhibit 1025, filed Apr. 30, 2013 in connection with IPR2012-00006).
Illumina's Answer to Amended Complaint from *The Trustees of Columbia University in the City of New York v. Illumina, Inc.*, D. Del C.A. No. 12-376 (GMS), filed Dec. 21, 2012 (Exhibit 1026, filed Apr. 30, 2013 in connection with IPR2012-00006).
Rosenblum et al., "New Dye-Labeled Terminators for Improved DNA Sequencing Patterns," Nucleic Acid Research, 1997, vol. 25, No. 22, pp. 4500-4504 (Exhibit 1030, filed Jun. 18, 2013 in connection with IPR2012-00006).
Jun. 8, 2013 Videotaped Deposition Transcript of George M. Weinstock, Ph.D. (Exhibit 1034, filed Jun. 18, 2013 in connection with IPR2012-0006).
"Next Generation Genomics: World Map of High-throughput Sequencers," Sep. 1, 2013 (Exhibit 1036, filed Sep. 27, 2013 in connection with IPR2012-00006).
Videotaped Deposition Transcript of Dr. Xiaohai Liu, Mar. 20, 2013 (Exhibit 1039, filed Sep. 27, 2013 in connection with IPR2012-0006).
Excerpt from videotaped Deposition Transcript of George M. Weinstock, Ph.D., Jun. 8, 2013 (Exhibit 1040, filed Sep. 27, 2013 in connection with IPR2012-00006).
Seela et al., "Oligonucleotide Duplex Stability Controlled by the 7-Substituents of 7-Deazaguanine Bases," Bioorganic & Medical Chemistry Letters, vol. 5, No. 24, pp. 3049-3052, 1995 (Exhibit 1041, filed Sep. 27, 2013 in connection with IPR2012-0006).
Ramzaeva et al., "123. 7-Deazaguanine DNA: Oligonucleotides with Hydrophobic or Cationic Side Chains," Helvetica Chimica Acta, vol. 80, pp. 1809-1822, 1997 (Exhibit 1042, filed Sep. 27, 2013 in connection with IPR2012-00006).
Ramzaeva et al., "88. 7-Substituted 7-Deaza-2'-deoxyguanosines: Regioselective Halogenation of Pyrrolo[2,3-d]pyrimidine Nucleosides," Helvetica Chimica Acta, vol. 78, pp. 1083-1090, 1995 (Exhibit 1043, filed Sep. 27, 2013 in connection with IPR2012-00006).
Seela et al., "Duplex Stability of Oligonucleotides Containing 7-Substituted 7-Deaza- and 8-Aza-7-Deazapurine Nucleosides," Nucleosides & Nucleotides, 16(7-9), pp. 963-966, 1997 (Exhibit 1044, filed Sep. 27, 2013 in connection with IPR2012-0006).
Burgess et al., "Syntheses of Nucleosides Designed for Combinatorial DNA Sequencing," Chemistry—A European Journal, vol. 5, No. 3, pp. 951-960, 1999 (Exhibit 1045, filed Sep. 27, 2013 in connection with IPR2012-00006).
Jan. 28, 2013 Declaration of Dr. Bruce P. Branchaud in Support of Petition for Inter Partes Review of U.S. Pat. No. 7,057,026 (Exhibit 1049, filed Sep. 27, 2013 in connection with IPR2012-0006).
Lee et al., "DNA sequencing with dye-labeled terminators and T7 DNA polymerase: effect of dyes and dNTPs on incorporation of dye-terminators and probability analysis of termination fragments," Nucleic Acids Research, vol. 20, No. 10, pp. 2471-2483, 1992 (Exhibit 1050, filed Sep. 27, 2013 in connection with IPR2012-00006).

(56) References Cited

OTHER PUBLICATIONS http://www.answers.com/topic/incubate, Accessed Sep. 27, 2013 (Exhibit 1051, filed Sep. 27, 2013 in connection with IPR2012-0006).
http://en.wikipedia.org/wiki/Fluorenylmethyloxycarbonyl_chloride, Accessed Sep. 27, 2013 (Exhibit 1052, filed Sep. 27, 2013 in connection with IPR2012-00006).
Sep. 27, 2013 Declaration of Kevin Burgess (Exhibit 1053, filed Sep. 27, 2013 in connection with IPR2012-00006).
Fuji, et al., "An Improved Method for Methoxymethylation of Alcohols under Mild Acidic Conditions," Synthesis—The Journal of Synthetic Organic Chemistry, pp. 276-277, Apr. 1975 (Exhibit 1054, filed Sep. 27, 2013 in connection with IPR2012-0006).
Dower patent with highlights (Exhibit 2006, filed Apr. 26, 2013 in connection with IPR2012-00006).
U.S. Pat. No. 7,713,698 (filed Aug. 20, 2007, issued May 11, 2010) (Exhibit 1001 in IPR2012-00006) (Exhibit 2011, filed Jun. 24, 2013 in connection with IPR2012-00006).
U.S. Pat. No. 7,790,869 (filed Jun. 5, 2007, issued Sep. 7, 2010) (Exhibit 1001 in IPR2012-00007) (Exhibit 2012, filed Jun. 24, 2013 in connection with IPR2012-00006).
Oct. 2, 2012 Declaration of George Weinstock Under 37 CFR 1.132 (Exhibit 1021 in IPR2013-00011) (Exhibit 2013, filed Jun. 24, 2013 in connection with IPR2012-00006).
Petition for Inter Partes Review of U.S. Pat. No. 8,088,575 (Paper 4 in IPR2013-00011) (Exhibit 2014, filed Jun. 24, 2013 in connection with IPR2012-0006).
Metzker et al. (1994) Termination of DNA synthesis by novel 3'-modified-deoxyribonucleoside 5'-triphosphates. Nucleic Acids Res. 22:4259-4267 (Exhibit 2015, filed Jun. 24, 2013 in connection with IPR2012-0006).
Wu et al. (2007) Termination of DNA synthesis by N6-alkylated, not 3'-O-alkylated, photocleavable 2'-deoxyadenosine triphosphates. Nucleic Acids Res. 35:6339-6349 (Exhibit 2016, filed Jun. 24, 2013 in connection with IPR2012-0006).
Sep. 15, 2012 Declaration of George Weinstock Under 37 CFR 1.132 (Exhibit 1021 in IPR2012-00007) (Exhibit 2017, filed Jun. 24, 2013 in connection with IPR2012-00006).
Sep. 15, 2012 Declaration of George Weinstock Under 37 CFR 1.132 (Exhibit 1021 in IPR2012-00006) (Exhibit 2018, filed Jun. 24, 2013 in connection with IPR2012-00006).
Definition of "DNA microarray." http://en/wikipedia.org/wiki/DNA_microarray (Exhibit 2019, filed Jun. 24, 2013 in connection with IPR2012-0006).
Brettin et al. (2005) Expression capable library for studies of Neisseria gonorrhoeae, version 1.0 MBC Microbiology. 5:50 (Exhibit 2020, filed Jun. 24, 2013 in connection with IPR2012-0006).
George M. Weinstock, Handbook of Molecular Microbial Ecology, vol. 1—Chapter 18: The Impact of Next-Generation Sequencing Technologies on Metagenomics 141-147 Frans J. de Bruijn ed., John Wiley & Sons, Inc. (2011) (Exhibit 2021, filed Jun. 24, 2013 in connection with IPR2012-0006).
Sep. 16, 2012 Petition for Inter Partes Review of U.S. Pat. No. 7,713,698 (Paper 3 in IPR2012-00006) (Exhibit 2022, filed Jun. 24, 2013 in connection with IPR2012-0006).
Sep. 16, 2012 Petition for Inter Partes Review of U.S. Pat. No. 7,790,869 (Paper 5 in IPR2012-00007) (Exhibit 2023, filed Jun. 24, 2013 in connection with IPR2012-0006).
Maxam and Gilbert (1977) A new method for sequencing DNA, Proc. Natl. Acad. Sci. USA. 74:560-564 (Exhibit 2024, filed Jun. 24, 2013 in connection with IPR2012-0006).
Final Written Decision dated Jun. 21, 2019, in connection with IPRs Nos. IPR2018-00291, IPR2018-00318, IPR2018-00322, and IPR2018-00385.

*CITMS = chlorotrimethylsilane (Nitro-Benzyl)-dATP

F-(Nitro-Benzyl)-dCTP 2F-(Nitro-Benzyl)-dGTP

2(Meo)-(Nitro-Benzyl)-dTTP

R = H, MOM or Allyl

SEQUENCE LISTING

<160> NUMBER OF SEQ ID NOS: 2

<210> SEQ ID NO 1
<211> LENGTH: 11
<212> TYPE: DNA
<213> ORGANISM: Artificial Sequence

```
<220> FEATURE:
<223> OTHER INFORMATION: Chemically Synthesized Template

<400> SEQUENCE: 1
acgtacgacg t                                                          11

<210> SEQ ID NO 2
<211> LENGTH: 105
<212> TYPE: DNA
<213> ORGANISM: Artificial Sequence
<220> FEATURE:
<223> OTHER INFORMATION: Chemically Synthesized Template

<400> SEQUENCE: 2
ttcctgcatg ggcggcatga acccgaggcc catcctcacc atcatcacac tggaagactc     60
cagtggtaat ctactgggac ggacggaaca gctttgaggt gcatt                    105
```

MASSIVE PARALLEL METHOD FOR DECODING DNA AND RNA

This application is a continuation of U.S. Ser. No. 15/915,983, filed Mar. 8, 2018, which is a continuation of U.S. Ser. No. 14/670,748, filed Mar. 27, 2015, which is a continuation of U.S. Ser. No. 13/959,660, filed Aug. 5, 2013, now U.S. Pat. No. 9,133,511, issued Sep. 15, 2015, which is a continuation of U.S. Ser. No. 13/672,437, filed Nov. 8, 2012, now abandoned, which is a continuation of U.S. Ser. No. 13/339,089, filed Dec. 28, 2011, now abandoned, which is a continuation of U.S. Ser. No. 12/804,284, filed Jul. 19, 2010, now U.S. Pat. No. 8,088,575, issued Jan. 3, 2012, which is a continuation of U.S. Ser. No. 11/810,509, filed Jun. 5, 2007, now U.S. Pat. No. 7,790,869, issued Sep. 7, 2010, which is a continuation of U.S. Ser. No. 10/702,203, filed Nov. 4, 2003, now U.S. Pat. No. 7,345,159, issued Mar. 18, 2008, which is a divisional of U.S. Ser. No. 09/972,364, filed Oct. 5, 2001, now U.S. Pat. No. 6,664,079, issued Dec. 16, 2003, claiming the benefit of U.S. Provisional Application No. 60/300,894, filed Jun. 26, 2001, and is a continuation-in-part of U.S. Ser. No. 09/684,670, filed Oct. 6, 2000, now abandoned, the contents of each which are hereby incorporated in entirety into this application.

This invention was made with government support under grant no. BES0097793 awarded by the National Science Foundation. The government has certain rights in the invention.

BACKGROUND OF THE INVENTION

Throughout this application, various publications are referenced in parentheses by author and year. Full citations for these references may be found at the end of the specification immediately preceding the claims. The disclosures of these publications in their entireties are hereby incorporated by reference into this application to more fully describe the state of the art to which this invention pertains.

The ability to sequence deoxyribonucleic acid (DNA) accurately and rapidly is revolutionizing biology and medicine. The confluence of the massive Human Genome Project is driving an exponential growth in the development of high throughput genetic analysis technologies. This rapid technological development involving chemistry, engineering, biology, and computer science makes it possible to move from studying single genes at a time to analyzing and comparing entire genomes.

With the completion of the first entire human genome sequence map, many areas in the genome that are highly polymorphic in both exons and introns will be known. The pharmacogenomics challenge is to comprehensively identify the genes and functional polymorphisms associated with the variability in drug response (Roses, 2000). Resequencing of polymorphic areas in the genome that are linked to disease development will contribute greatly to the understanding of diseases, such as cancer, and therapeutic development. Thus, high-throughput accurate methods for resequencing the highly variable intron/exon regions of the genome are needed in order to explore the full potential of the complete human genome sequence map. The current state-of-the-art technology for high throughput DNA sequencing, such as used for the Human Genome Project (Pennisi 2000), is capillary array DNA sequencers using laser induced fluorescence detection (Smith et al., 1986; Ju et al. 1995, 1996; Kheterpal et al. 1996; Salas-Solano et al. 1998). Improvements in the polymerase that lead to uniform termination efficiency and the introduction of thermostable polymerases have also significantly improved the quality of sequencing data (Tabor and Richardson, 1987, 1995). Although capillary array DNA sequencing technology to some extent addresses the throughput and read length requirements of large scale DNA sequencing projects, the throughput and accuracy required for mutation studies needs to be improved for a wide variety of applications ranging from disease gene discovery to forensic identification. For example, electrophoresis based DNA sequencing methods have difficulty detecting heterozygotes unambiguously and are not 100% accurate in regions rich in nucleotides comprising guanine or cytosine clue to compressions (Bowling et al. 1991; Yamakawa et al. 1997). In addition, the first few bases after the priming site are often masked by the high fluorescence signal from excess dye-labeled primers or dye-labeled terminators, and are therefore difficult to identify. Therefore, the requirement of electrophoresis for DNA sequencing is still the bottleneck for high-throughput DNA sequencing and mutation detection projects.

The concept of sequencing DNA by synthesis without using electrophoresis was first revealed in 1988 (Hyman, 1988) and involves detecting the identity of each nucleotide as it is incorporated into the growing strand of DNA in a polymerase reaction. Such a scheme coupled with the chip format and laser-induced fluorescent detection has the potential to markedly increase the throughput of DNA sequencing projects. Consequently, several groups have investigated such a system with an aim to construct an ultra high-throughput DNA sequencing procedure (Cheeseman 1994, Metzker et al. 1994). Thus far, no complete success of using such a system to unambiguously sequence DNA has been reported. The pyrosequencing approach that employs four natural nucleotides (comprising a base of adenine (A), cytosine (C), guanine (G), or thymine (T)) and several other enzymes for sequencing DNA by synthesis is now widely used for mutation detection (Ronaghi 1998). In this approach, the detection is based on the pyrophosphate (PPi) released during the DNA polymerase reaction, the quantitative conversion of pyrophosphate to adenosine triphosphate (ATP) by sulfurylase, and the subsequent production of visible light by firefly luciferase. This procedure can only sequence up to 30 base pairs (bps) of nucleotide sequences, and each of the 4 nucleotides needs to be added separately and detected separately. Long stretches of the same bases cannot be identified unambiguously with the pyrosequencing method.

More recent work in the literature exploring DNA sequencing by a synthesis method is mostly focused on designing and synthesizing a photocleavable chemical moiety that is linked to a fluorescent dye to cap the 3'-OH group of deoxynucleoside triphosphates (dNTPs) (Welch et al. 1999). Limited success for the incorporation of the 3'-modified nucleotide by DNA polymerase is reported. The reason is that the 3'-position on the deoxyribose is very close to the amino acid residues in the active site of the polymerase, and the polymerase is therefore sensitive to modification in this area of the deoxyribose ring. On the other hand, it is known that modified DNA polymerases (Thermo Sequenase and Taq FS polymerase) are able to recognize nucleotides with extensive modifications with bulky groups such as energy transfer dyes at the 5-position of the pyrimidines (T and C) and at the 7-position of purines (G and A) (Rosenblum et al. 1997, Zhu et al. 1994). The ternary complexes of rat DNA polymerase, a DNA template-primer, and dideoxycytidine triphosphate (ddCTP) have been determined (Pelletier et al. 1994) which supports this fact. As shown in FIG. 1, the 3-D structure indicates that the surrounding area of the 3'-position of the deoxyribose ring in ddCTP is very crowded, while there is ample space for modification on the 5-position the cytidine base.

The approach disclosed in the present application is to make nucleotide analogues by linking a unique label such as a fluorescent dye or a mass tag through a cleavable linker to the nucleotide base or an analogue of the nucleotide base, such as to the 5-position of the pyrimidines (T and C) and to the 7-position of the purines (G and A), to use a small cleavable chemical moiety to cap the 3'-OH group of the deoxyribose to make it nonreactive and to incorporate the nucleotide analogues into the growing DNA strand as terminators. Detection of the unique label will yield the sequence identity of the nucleotide. Upon removing the label and the 3'-OH capping group, the polymerase reaction will proceed to incorporate the next nucleotide analogue and detect the next base.

It is also desirable to use a photocleavable group to cap the 3'-OH group. However, a photocleavable group is generally bulky and thus the DNA polymerase will have difficulty to incorporate the nucleotide analogues containing a photocleavable moiety capping the 3'-OH group. If small chemical moieties that can be easily cleaved chemically with high yield can be used to cap the 3'-OH group, such nucleotide analogues should also be recognized as substrates for DNA polymerase. It has been reported that 3'-O-methoxy-deoxynucleotides are good substrates for several polymerases (Axelrod et al. 1978). 3'-O-allyl-dATP was also shown to be incorporated by Ventr(exo-) DNA polymerase in the growing strand of DNA (Metzker et al. 1994). However, the procedure to chemically cleave the methoxy group is stringent and requires anhydrous conditions. Thus, it is not practical to use a methoxy group to cap the 3'-OH group for sequencing DNA by synthesis. An ester group was also explored to cap the 3'-OH group of the nucleotide, but it was shown to be cleaved by the nucleophiles in the active site in DNA polymerase (Canard et al. 1995). Chemical groups with electrophiles such as ketone groups are not suitable for protecting the 3'-OH of the nucleotide in enzymatic reactions due to the existence of strong nucleophiles in the polymerase. It is known that MOM (—$CH_2OCH_3$) and allyl (—$CH_2CH=CH_2$) groups can be used to cap an —OH group, and can be cleaved chemically with high yield (Ireland et al. 1986; Kamal et al. 1999). The approach disclosed in the present application is to incorporate nucleotide analogues, which are labeled with cleavable, unique labels such as fluorescent dyes or mass tags and where the 3'-OH is capped with a cleavable chemical moiety such as either a MOM group (—$CH_2OCH_3$) or an allyl group (—$CH_2CH=CH_2$), into the growing strand DNA as terminators. The optimized nucleotide set ($3'_{-RO}$-A-$_{LABEL1}$, $3'_{-RO}$-C-$_{LABEL2}$, $3'_{-RO}$-G-$_{LABEL3}$, $3'_{-RO}$-T-$_{LABEL4}$, where R denotes the chemical group used to cap the 3'-OH) can then be used for DNA sequencing by the synthesis approach.

There are many advantages of using mass spectrometry (MS) to detect small and stable molecules. For example, the mass resolution can be as good as one dalton. Thus, compared to gel electrophoresis sequencing systems and the laser induced fluorescence detection approach which have overlapping fluorescence emission spectra, leading to heterozygote detection difficulty, the MS approach disclosed in this application produces very high resolution of sequencing data by detecting the cleaved small mass tags instead of the long DNA fragment. This method also produces extremely fast separation in the time scale of microseconds. The high resolution allows accurate digital mutation and heterozygote detection. Another advantage of sequencing with mass spectrometry by detecting the small mass tags is that the compressions associated with gel based systems are completely eliminated.

In order to maintain a continuous hybridized primer extension product with the template DNA, a primer that contains a stable loop to form an entity capable of self-priming in a polymerase reaction can be ligated to the 3' end of each single stranded DNA template that is immobilized on a solid surface such as a chip. This approach will solve the problem of washing off the growing extension products in each cycle.

Saxon and Bertozzi (2000) developed an elegant and highly specific coupling chemistry linking a specific group that contains a phosphine moiety to an azido group on the surface of a biological cell. In the present application, this coupling chemistry is adopted to create a solid surface which is coated with a covalently linked phosphine moiety, and to generate polymerase chain reaction (PCR) products that contain an azido group at the 5' end for specific coupling of the DNA template with the solid surface. One example of a solid surface is glass channels which have an inner wall with an uneven or porous surface to increase the surface area. Another example is a chip.

The present application discloses a novel and advantageous system for DNA sequencing by the synthesis approach which employs a stable DNA template, which is able to self prime for the polymerase reaction, covalently linked to a solid surface such as a chip, and 4 unique nucleotides analogues ($3'_{-RO}$-A-$_{LABEL1}$, $3'_{-RO}$-C-$_{LABEL2}$, $3'_{-RO}$-G-$_{LABEL3}$, $3'_{-RO}$-T-$_{LABEL4}$). The success of this novel system will allow the development of an ultra high-throughput and high fidelity DNA sequencing system for polymorphism, pharmacogenetics applications and for whole genome sequencing. This fast and accurate DNA resequencing system is needed in such fields as detection of single nucleotide polymorphisms (SNPs) (Chee et al. 1996), serial analysis of gene expression (SAGE) (Velculescu et al. 1995), identification in forensics, and genetic disease association studies.

SUMMARY OF THE INVENTION

This invention is directed to a method for sequencing a nucleic acid by detecting the identity of a nucleotide analogue after the nucleotide analogue is incorporated into a growing strand of DNA in a polymerase reaction, which comprises the following steps:

(i) attaching a 5' end of the nucleic acid to a solid surface;
(ii) attaching a primer to the nucleic acid attached to the solid surface;
(iii) adding a polymerase and one or more different nucleotide analogues to the nucleic acid to thereby incorporate a nucleotide analogue into the growing strand of DNA, wherein the incorporated nucleotide analogue terminates the polymerase reaction and wherein each different nucleotide analogue comprises (a) a base selected from the group consisting of adenine, guanine, cytosine, thymine, and uracil, and their analogues; (b) a unique label attached through a cleavable linker to the base or to an analogue of the base; (c) a deoxyribose; and (d) a cleavable chemical group to cap an —OH group at a 3'-position of the deoxyribose;
(iv) washing the solid surface to remove unincorporated nucleotide analogues;

(v) detecting the unique label attached to the nucleotide analogue that has been incorporated into the growing strand of DNA, so as to thereby identify the incorporated nucleotide analogue;

(vi) adding one or more chemical compounds to permanently cap any unreacted —OH group on the primer attached to the nucleic acid or on a primer extension strand formed by adding one or more nucleotides or nucleotide analogues to the primer;

(vii) cleaving the cleavable linker between the nucleotide analogue that was incorporated into the growing strand of DNA and the unique label;

(viii) cleaving the cleavable chemical group capping the —OH group at the 3'-position of the deoxyribose to uncap the —OH group, and washing the solid surface to remove cleaved compounds; and (ix) repeating steps (iii) through (viii) so as to detect the identity of a newly incorporated nucleotide analogue into the growing strand of DNA;

wherein if the unique label is a dye, the order of steps (v) through (vii) is: (v), (vi), and (vii); and wherein if the unique label is a mass tag, the order of steps (v) through (vii) is: (vi), (vii), and (v).

The invention provides a method of attaching a nucleic acid to a solid surface which comprises:

(i) coating the solid surface with a phosphine moiety, (ii) attaching an azido group to a 5' end of the nucleic acid, and (iii) immobilizing the 5' end of the nucleic acid to the solid surface through interaction between the phosphine moiety on the solid surface and the azido group on the 5' end of the nucleic acid.

The invention provides a nucleotide analogue which comprises:

(a) a base selected from the group consisting of adenine or an analogue of adenine, cytosine or an analogue of cytosine, guanine or an analogue of guanine, thymine or an analogue of thymine, and uracil or an analogue of uracil;

(b) a unique label attached through a cleavable linker to the base or to an analogue of the base;

(c) a deoxyribose; and (d) a cleavable chemical group to cap an —OH group at a 3'-position of the deoxyribose.

The invention provides a parallel mass spectrometry system, which comprises a plurality of atmospheric pressure chemical ionization mass spectrometers for parallel analysis of a plurality of samples comprising mass tags.

DETAILED DESCRIPTION OF THE INVENTION

Figure 1:
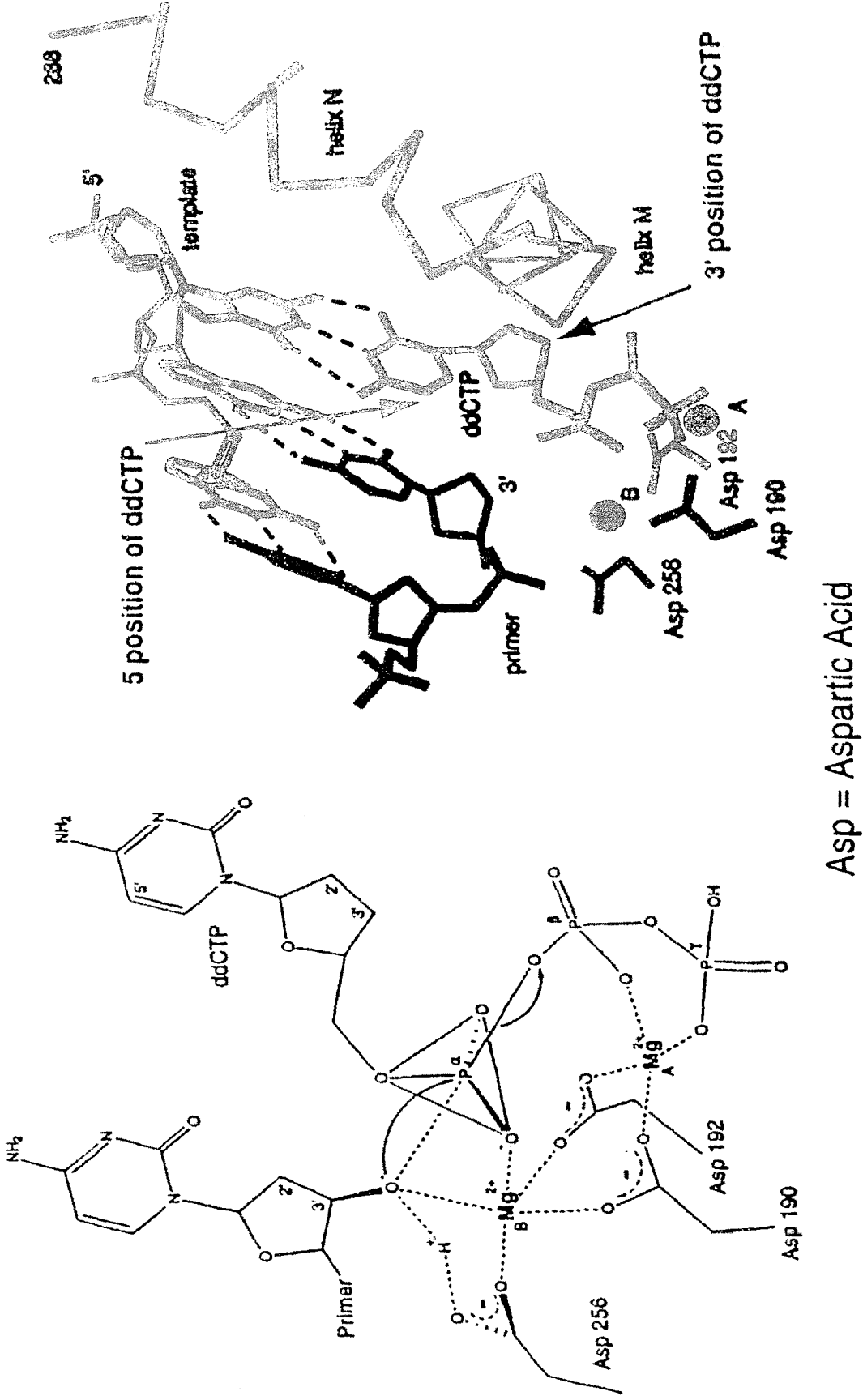
FIG. 1: The 3D structure of the ternary complexes of rat DNA polymerase, a DNA template-primer, and dideoxycytidine triphosphate (ddCTP). The left side of the illustration shows the mechanism for the addition of ddCTP and the right side of the illustration shows the active site of the polymerase. Note that the 3' position of the dideoxyribose ring is very crowded, while ample space is available at the 5 position of the cytidine base.

The following definitions are presented as an aid in understanding this invention.

As used herein, to cap an —OH group means to replace the "H" in the —OH group with a chemical group. As disclosed herein, the —OH group of the nucleotide analogue is capped with a cleavable chemical group. To uncap an —OH group means to cleave the chemical group from a capped —OH group and to replace the chemical group with "H", i.e., to replace the "R" in —OR with "H" wherein "R" is the chemical group used to cap the —OH group.

The nucleotide bases are abbreviated as follows: adenine (A), cytosine (C), guanine (G), thymine (T), and uracil (U).

An analogue of a nucleotide base refers to a structural and functional derivative of the base of a nucleotide which can be recognized by polymerase as a substrate. That is, for example, an analogue of adenine (A) should form hydrogen bonds with thymine (T), a C analogue should form hydrogen bonds with G, a G analogue should form hydrogen bonds with C, and a T analogue should form hydrogen bonds with A, in a double helix format. Examples of analogues of nucleotide bases include, but are not limited to, 7-deaza-adenine and 7-deaza-guanine, wherein the nitrogen atom at the 7-position of adenine or guanine is substituted with a carbon atom.

A nucleotide analogue refers to a chemical compound that is structurally and functionally similar to the nucleotide, i.e. the nucleotide analogue can be recognized by polymerase as a substrate. That is, for example, a nucleotide analogue comprising adenine or an analogue of adenine should form hydrogen bonds with thymine, a nucleotide analogue comprising C or an analogue of C should form hydrogen bonds with G, a nucleotide analogue comprising G or an analogue of G should form hydrogen bonds with C, and a nucleotide analogue comprising T or an analogue of T should form hydrogen bonds with A, in a double helix format. Examples of nucleotide analogues disclosed herein include analogues which comprise an analogue of the nucleotide base such as 7-deaza-adenine or 7-deaza-guanine, wherein the nitrogen atom at the 7-position of adenine or guanine is substituted with a carbon atom. Further examples include analogues in which a label is attached through a cleavable linker to the 5-position of cytosine or thymine or to the 7-position of deaza-adenine or deaza-guanine. Other examples include analogues in which a small chemical moiety such as —$CH_2OCH_3$ or —$CH_2CH=CH_2$ is used to cap the —OH group at the 3'-position of deoxyribose. Analogues of dideoxynucleotides can similarly be prepared.

As used herein, a porous surface is a surface which contains pores or is otherwise uneven, such that the surface area of the porous surface is increased relative to the surface area when the surface is smooth.

The present invention is directed to a method for sequencing a nucleic acid by detecting the identity of a nucleotide analogue after the nucleotide analogue is incorporated into a growing strand of DNA in a polymerase reaction, which comprises the following steps:

(i) attaching a 5' end of the nucleic acid to a solid surface;

(ii) attaching a primer to the nucleic acid attached to the solid surface;

(iii) adding a polymerase and one or more different nucleotide analogues to the nucleic acid to thereby incorporate a nucleotide analogue into the growing strand of DNA, wherein the incorporated nucleotide analogue terminates the polymerase reaction and wherein each different nucleotide analogue comprises (a) a base selected from the group consisting of adenine, guanine, cytosine, thymine, and uracil, and their analogues; (b) a unique label attached through a cleavable linker to the base or to an analogue of the base; (c) a deoxyribose; and (d) a cleavable chemical group to cap an —OH group at a 3'-position of the deoxyribose;

(iv) washing the solid surface to remove unincorporated nucleotide analogues;

(v) detecting the unique label attached to the nucleotide analogue that has been incorporated into the growing strand of DNA, so as to thereby identify the incorporated nucleotide analogue;

(vi) adding one or more chemical compounds to permanently cap any unreacted —OH group on the primer attached to the nucleic acid or on a primer extension strand formed by adding one or more nucleotides or nucleotide analogues to the primer;

(vii) cleaving the cleavable linker between the nucleotide analogue that was incorporated into the growing strand of DNA and the unique label;

(viii) cleaving the cleavable chemical group capping the —OH group at the 3'-position of the deoxyribose to uncap the —OH group, and washing the solid surface to remove cleaved compounds; and (ix) repeating steps (iii) through (viii) so as to detect the identity of a newly incorporated nucleotide analogue into the growing strand of DNA;

wherein if the unique label is a dye, the order of steps (v) through (vii) is: (v), (vi), and (vii); and wherein if the unique label is a mass tag, the order of steps (v) through (vii) is: (vi), (vii), and (v).

In one embodiment of any of the nucleotide analogues described herein, the nucleotide base is adenine. In one embodiment, the nucleotide base is guanine. In one embodiment, the nucleotide base is cytosine. In one embodiment, the nucleotide base is thymine. In one embodiment, the nucleotide base is uracil. In one embodiment, the nucleotide base is an analogue of adenine. In one embodiment, the nucleotide base is an analogue of guanine. In one embodiment, the nucleotide base is an analogue of cytosine. In one embodiment, the nucleotide base is an analogue of thymine. In one embodiment, the nucleotide base is an analogue of uracil.

In different embodiments of any of the inventions described herein, the solid surface is glass, silicon, or gold. In different embodiments, the solid surface is a magnetic bead, a chip, a channel in a chip, or a porous channel in a chip. In one embodiment, the solid surface is glass. In one embodiment, the solid surface is silicon. In one embodiment, the solid surface is gold. In one embodiments, the solid surface is a magnetic bead. In one embodiment, the solid surface is a chip. In one embodiment, the solid surface is a channel in a chip. In one embodiment, the solid surface is a porous channel in a chip. Other materials can also be used as long as the material does not interfere with the steps of the method.

In one embodiment, the step of attaching the nucleic acid to the solid surface comprises:

(i) coating the solid surface with a phosphine moiety,
(ii) attaching an azido group to the 5' end of the nucleic acid, and
(iii) immobilizing the 5' end of the nucleic acid to the solid surface through interaction between the phosphine moiety on the solid surface and the azido group on the 5' end of the nucleic acid.

In one embodiment, the step of coating the solid surface with the phosphine moiety comprises:

(i) coating the surface with a primary amine, and
(ii) covalently coupling a N-hydroxysuccinimidyl ester of triarylphosphine with the primary amine.

In one embodiment, the nucleic acid that is attached to the solid surface is a single-stranded deoxyribonucleic acid (DNA). In another embodiment, the nucleic acid that is attached to the solid surface in step (i) is a double-stranded DNA, wherein only one strand is directly attached to the solid surface, and wherein the strand that is not directly attached to the solid surface is removed by denaturing before proceeding to stop (ii). In one embodiment, the nucleic acid that is attached to the solid surface is a ribonucleic acid (RNA), and the polymerase in step (iii) is reverse transcriptase.

In one embodiment, the primer is attached to a 3' end of the nucleic acid in step (ii), and the attached primer comprises a stable loop and an —OH group at a 3'-position of a deoxyribose capable of self-priming in the polymerase reaction. In one embodiment, the step of attaching the primer to the nucleic acid comprises hybridizing the primer to the nucleic acid or ligating the primer to the nucleic acid. In one embodiment, the primer is attached to the nucleic acid through a ligation reaction which links the 3' end of the nucleic acid with the 5' end of the primer.

In one embodiment, one or more of four different nucleotide analogs is added in step (iii), wherein each different nucleotide analogue comprises a different base selected from the group consisting of thymine or uracil or an analogue of thymine or uracil, adenine or an analogue of adenine, cytosine or an analogue of cytosine, and guanine or an analogue of guanine, and wherein each of the four different nucleotide analogues comprises a unique label.

In one embodiment, the cleavable chemical group that caps the —OH group at the 3'-position of the deoxyribose in the nucleotide analogue is —$CH_2OCH_3$ or —$CH_2CH$=$CH_2$. Any chemical group could be used as long as the group 1) is stable during the polymerase reaction, 2) does not interfere with the recognition of the nucleotide analogue by polymerase as a substrate, and 3) is cleavable.

In one embodiment, the unique label that is attached to the nucleotide analogue is a fluorescent moiety or a fluorescent semiconductor crystal. In further embodiments, the fluorescent moiety is selected from the group consisting of 5-carboxyfluorescein, 6-carboxyrhodamine-6G, N,N,N',N'-tetramethyl-6-carboxyrhodamine, and 6-carboxy-X-rhodamine. In one embodiment, the fluorescent moiety is 5-carboxyfluorescein. In one embodiment, the fluorescent moiety is 6-carboxyrhodamine-6G, N,N,N',N'-tetramethyl-6-carboxyrhodamine. In one embodiment, the fluorescent moiety is 6-carboxy-X-rhodamine.

In one embodiment, the unique label that is attached to the nucleotide analogue is a fluorescence energy transfer tag which comprises an energy transfer donor and an energy transfer acceptor. In further embodiments, the energy transfer donor is 5-carboxyfluorescein or cyanine, and wherein the energy transfer acceptor is selected from the group consisting of dichlorocarboxyfluorescein, dichloro-6-carboxyrhodamine-6G, dichloro-N,N,N',N'-tetramethyl-6-carboxyrhodamine, and dichloro-6-carboxy-X-rhodainine. In one embodiment, the energy transfer acceptor is dichlorocarboxyfluorescein. In one embodiment, the energy transfer acceptor is dichloro-6-carboxyrhodamine-6G. In one embodiment, the energy transfer acceptor is dichloro-N,N,N',N'-tetramethyl-6-carboxyrhodamine. In one embodiment, the energy transfer acceptor is dichloro-6-carboxy-X-rhodamine.

In one embodiment, the unique label that is attached to the nucleotide analogue is a mass tag that can be detected and differentiated by a mass spectrometer. In further embodiments, the mass tag is selected from the group consisting of a 2-nitro-α-methyl-benzyl group, a 2-nitro-α-methyl-3-fluorobenzyl group, a 2-nitro-α-methyl-3,4-difluorobenzyl group, and a 2-nitro-α-methyl-3,4-dimethoxybenzyl group. In one embodiment, the mass tag is a 2-nitro-α-methyl-benzyl group. In one embodiment, the mass tag is a 2-nitro-α-methyl-3-fluorobenzyl group. In one embodiment, the mass tag is a 2-nitro-α-methyl-3, 4-difluorobenzyl group. In one embodiment, the mass tag is a 2-nitro-α-methyl-3,4-dimethoxybenzyl group. In one embodiment, the mass tag is detected using a parallel mass spectrometry system which comprises a plurality of atmospheric pressure chemical ionization mass spectrometers for parallel analysis of a plurality of samples comprising mass tags.

In one embodiment, the unique label is attached through a cleavable linker to a 5-position of cytosine or thymine or to a 7-position of deaza-adenine or deaza-guanine. The unique label could also be attached through a cleavable linker to another position in the nucleotide analogue as long as the attachment of the label is stable during the polymerase reaction and the nucleotide analog can be recognized by polymerase as a substrate. For example, the cleavable label could be attached to the deoxyribose.

In one embodiment, the linker between the unique label and the nucleotide analogue is cleaved by a means selected from the group consisting of one or more of a physical means, a chemical means, a physical chemical means, heat, and light. In one embodiment, the linker is cleaved by a physical means. In one embodiment, the linker is cleaved by a chemical means. In one embodiment, the linker is cleaved by a physical chemical means. In one embodiment, the linker is cleaved by heat. In one embodiment, the linker is cleaved by light. In one embodiment, the linker is cleaved by ultraviolet light. In a further embodiment, the cleavable linker is a photocleavable linker which comprises a 2-nitrobenzyl moiety.

In one embodiment, the cleavable chemical group used to cap the —OH group at the 3'-position of the deoxyribose is cleaved by a means selected from the group consisting of one or more of a physical means, a chemical means, a physical chemical means, heat, and light. In one embodiment, the linker is cleaved by a physical chemical means. In one embodiment, the linker is cleaved by heat. In one embodiment, the linker is cleaved by light. In one embodiment, the linker is cleaved by ultraviolet light.

In one embodiment, the chemical compounds added in step (vi) to permanently cap any un reacted —OH group on the primer attached to the nucleic acid or on the primer extension strand are a polymerase and one or more different dideoxynucleotides or analogues of dideoxynucleotides. In further embodiments, the different dideoxynucleotides are selected from the group consisting of 2',3'-dideoxyadenosine 5'-triphosphate, 2',3'-dideoxyguanosine 5'-triphosphate, 2',3'-dideoxycytidine 5'-triphosphate, 2',3'-dideoxythymidine 5'-triphosphate, 2',3'-dideoxyuridine 5'-triphosphase, and their analogues. In one embodiment, the dideoxynucleotide is 2',3'-dideoxyadenosine 5'-triphosphate. In one embodiment, the dideoxynucleotide is 2',3'-dideoxyguanosine 5'-triphosphate. In one embodiment, the dideoxynucleotide is 2',3'-dideoxycytidine 5'-triphosphate. In one embodiment, the dideoxynucleotide is 2',3'-dideoxythymidine 5'-triphosphate. In one embodiment, the dideoxynucleotide is 2',3'-dideoxyuridine 5'-triphosphase. In one embodiment, the dideoxynucleotide is an analogue of 2',3'-dideoxyadenosine 5'-triphosphate. In one embodiment, the dideoxynucleotide is an analogue of 2',3'-dideoxyguanosine 5'-triphosphate. In one embodiment, the dideoxynucleotide is an analogue of 2',3'-dideoxycytidine 5'-triphosphate. In one embodiment, the dideoxy nucleotide is an analogue of 2',3'-dideoxythymidine 5'-triphosphate. In one embodiment, the dideoxynucleotide is an analogue of 2',3'-dideoxyuridine 5'-triphosphase.

In one embodiment, a polymerase and one or more of four different dideoxynucleotides are added in step (vi), wherein each different dideoxynucleotide is selected from the group consisting of 2',3'-dideoxyadenosine 5'-triphosphate or an analogue of 2',3'-dideoxyadenosine 5'-triphosphate; 2',3'-dideoxyguanosine 5'-triphosphate or an analogue of 2',3'-dideoxyguanosine 5'-triphosphate; 2',3'-dideoxycytidine 5'-triphosphate or an analogue of 2',3'-dideoxycytidine 5'-triphosphate; and 2',3'-dideoxythymidine 5'-triphosphate or 2',3'-dideoxyuridine 5'-triphosphase or an analogue of 2',3'-dideoxythymidine 5'-triphosphate or an analogue of 2',3'-dideoxyuridine 5'-triphosphase. In one embodiment, the dideoxynucleotide is 2',3'-dideoxyadenosine 5'-triphosphate. In one embodiment, the dideoxynucleotide is an analogue of 2',3'-dideoxyadenosine 5'-triphosphate. In one embodiment, the dideoxynucleotide is 2',3'-dideoxyguanosine 5'-triphosphate. In one embodiment, the dideoxynucleotide is an analogue of 2',3'-dideoxyguanosine 5'-triphosphate. In one embodiment, the dideoxynucleotide is 2',3'-dideoxycytidine 5'-triphosphate. In one embodiment, the dideoxynucleotide is an analogue of 2',3'-dideoxycytidine 5'-triphosphate. In one embodiment, the dideoxynucleotide is 2',3'-dideoxythymidine 5'-triphosphate. In one embodiment, the dideoxynucleotide is 2',3'-dideoxyuridine 5'-triphosphase. In one embodiment, the dideoxynucleotide is an analogue of 2',3'-dideoxythymidine 5'-triphosphate. In one embodiment, the dideoxynucleotide is an analogue of 2',3'-dideoxyuridine 5'-triphosphase.

Another type of chemical compound that reacts specifically with the —OH group could also be used to permanently cap any unreacted —OH group on the primer attached to the nucleic acid or on an extension strand formed by adding one or more nucleotides or nucleotide analogues to the primer.

The invention provides a method for simultaneously sequencing a plurality of different nucleic acids, which comprises simultaneously applying any of the methods disclosed herein for sequencing a nucleic acid to the plurality of different nucleic acids. In different embodiments, the method can be used to sequence from one to over 100,000 different nucleic acids simultaneously.

The invention provides for the use of any of the methods disclosed herein for detection of single nucleotide polymorphisms, genetic mutation analysis, serial analysis of gene expression, gene expression analysis, identification in forensics, genetic disease association studies, DNA sequencing, genomic sequencing, translational analysis, or transcriptional analysis.

The invention provides a method of attaching a nucleic acid to a solid surface which comprises:
  (i) coating the solid surface with a phosphine moiety,
  (ii) attaching an azido group to a 5' end of the nucleic acid, and
  (iii) immobilizing the 5' end of the nucleic acid to the solid surface through interaction between the phosphine moiety on the solid surface and the azido group on the 5' end of the nucleic acid.

In one embodiment, the step of coating the solid surface with the phosphine moiety comprises:
  (i) coating the surface with a primary amine, and
  (ii) covalently coupling a N-hydroxysuccinimidyl ester of triarylphosphine with the primary amine.

In different embodiments, the solid surface is glass, silicon, or gold. In different embodiments, the solid surface is a magnetic bead, a chip, a channel in an chip, or a porous channel in a chip.

In different embodiments, the nucleic acid that is attached to the solid surface is a single-stranded or double-stranded DNA or a RNA. In one embodiment, the nucleic acid is a double-stranded DNA and only one strand is attached to the solid surface. In a further embodiment, the strand of the double-stranded DNA that is not attached to the solid surface is removed by denaturing.

The invention provides for the use of any of the methods disclosed herein for attaching a nucleic acid to a surface for gene expression analysis, microarray based gene expression analysis, or mutation detection, translation analysis, transcriptional analysis, or for other genetic applications.

The invention provides a nucleotide analogue which comprises:

(a) a base selected from the group consisting of adenine or an analogue of adenines, cytosine or an analogue of cytosine, guanine or an analogue of guanine, thymine or an analogue of thymine, and uracil or an analogue of uracil;
(b) a unique label attached through a cleavable linker to the base or to an analogue of the base;
(c) a deoxyribose; and
(d) a cleavable chemical group to cap an —OH group at a 3'-position of the deoxyribose.

In one embodiment of the nucleotide analogue, the cleavable chemical group that caps the —OH group at the 3'-position of the deoxyribose is —CH$_2$OCH$_3$ or —CH$_2$CH=CH$_2$.

In one embodiment, the unique label is a fluorescent moiety or a fluorescent semiconductor crystal. In further embodiments, the fluorescent moiety is selected from the group consisting of 5-carboxyfluorescein, 5-carboxyrhodamine-6G, N,N,N',N'-tetramethyl-6-carboxyrhodamine, and 6-carboxy-X-rhodamine.

In one embodiment, the unique label is a fluorescence energy transfer tag which comprises an energy transfer donor and an energy transfer acceptor. In further embodiments, the energy transfer donor is 5-carboxyfluorescein or cyanine, and wherein the energy transfer acceptor is selected from the group consisting of dichlorocarboxyfluorescein, dichloro-6-carboxyrhodamine-6G, dichloro-N,N,N',N'-tetramethyl-6-carboxyrhodamine, and dichloro-6-carboxy-X-rhodamine.

In one embodiment, the unique label is a mass tag that can be detected and differentiated by a mass spectrometer. In further embodiments, the mass tag is selected from the group consisting of a 2-nitro-α-methyl-benzyl group, a 2-nitro-α-methyl-3-fluorobenzyl group, a 2-nitro-α-methyl-3,4-difluorobenzyl group, and a 2-nitro-α-methyl-3,4-dimethoxybenzyl group.

In one embodiment, the unique label is attached through a cleavable linker to a 5-position of cytosine or thymine or to a 7-position of deaza-adenine or deaza-guanine. The unique label could also be attached through a cleavable linker to another position in the nucleotide analogue as long as the attachment of the label is stable during the polymerase reaction and the nucleotide analog can be recognized by polymerase as a substrate. For example, the cleavable label could be attached to the deoxyribose.

In one embodiment, the linker between the unique label and the nucleotide analogue is cleavable by a means selected from the group consisting of one or more of a physical means, a chemical means, a physical chemical means, heat, and light. In a further embodiment, the cleavable linker is a photocleavable linker which comprises a 2-nitrobenzyl moiety.

In one embodiment, the cleavable chemical group used to cap the —OH group at the 3'-position of the deoxyribose is cleavable by a means selected from the group consisting of one or more of a physical means, a chemical means, a physical chemical means, heat, and light.

In different embodiments, the nucleotide analogue is selected from the group consisting of:

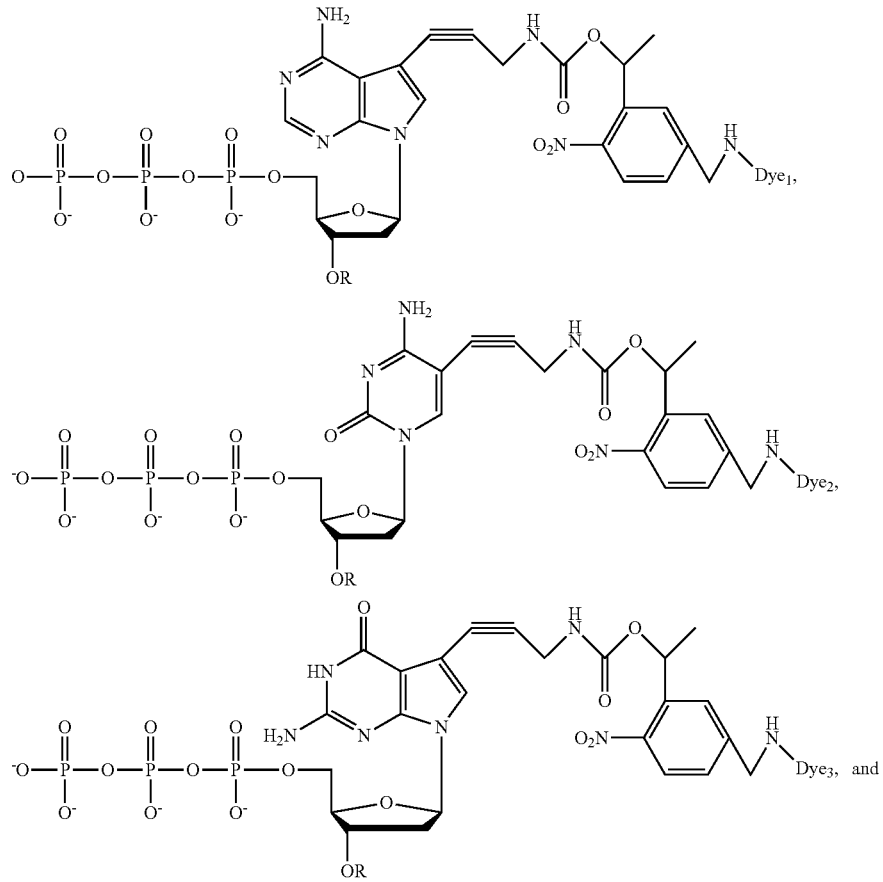

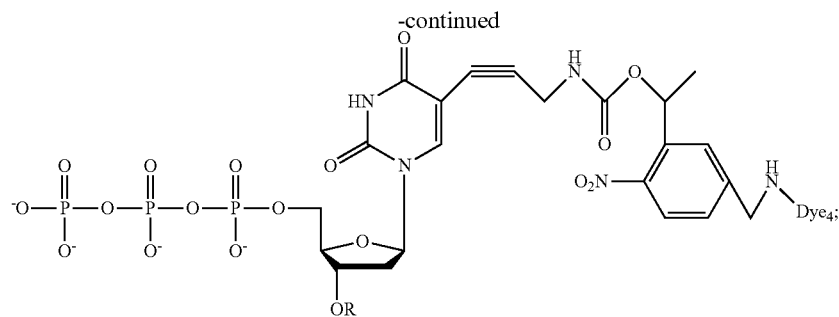
wherein $Dye_1$, $Dye_2$, $Dye_3$, and $Dye_4$ are four different unique labels; and
wherein R is a cleavable chemical group used to cap the —OH group at the 3'-position of the deoxyribose.
In different embodiments, the nucleotide analogue is selected from the group consisting of:
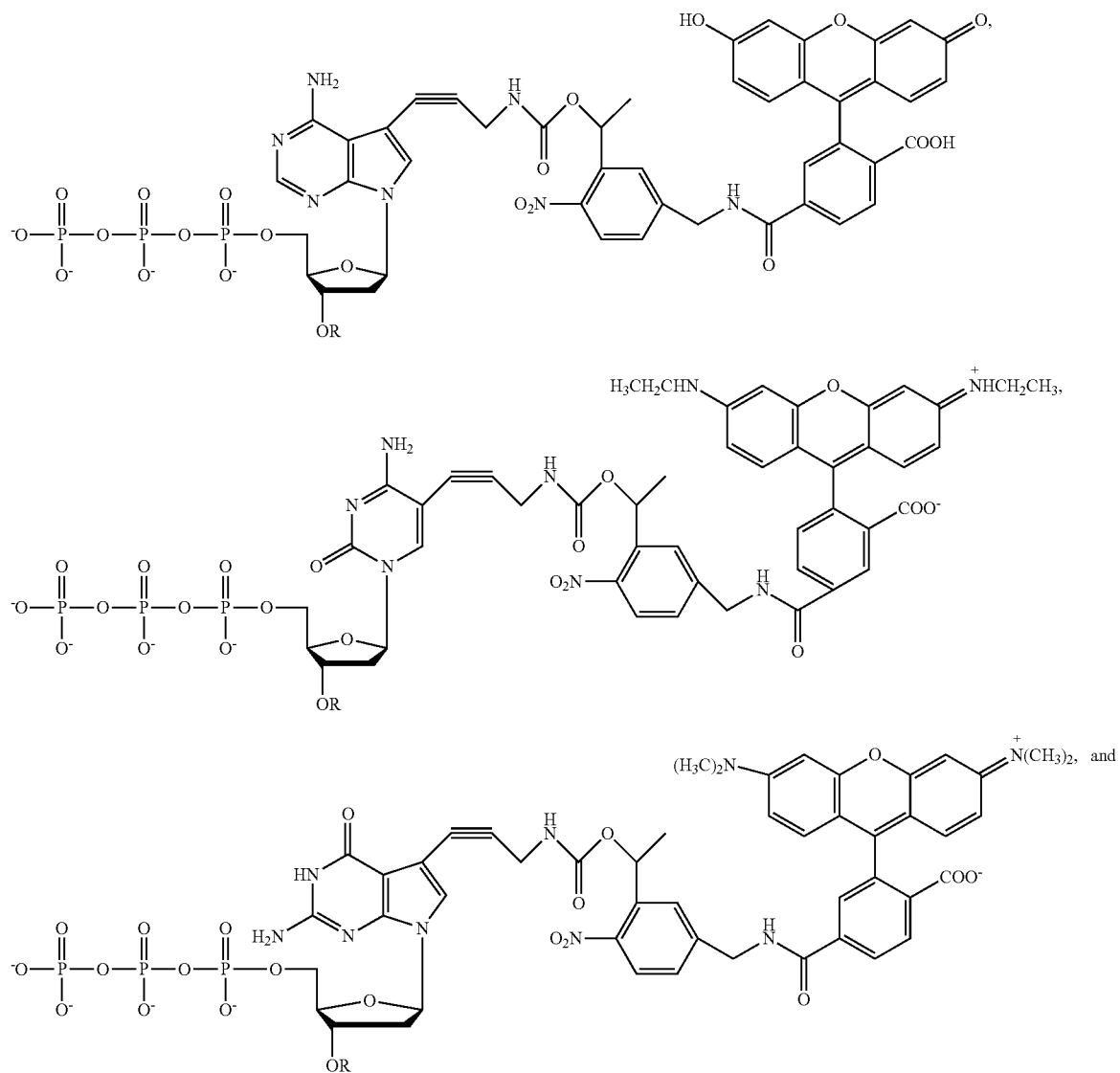

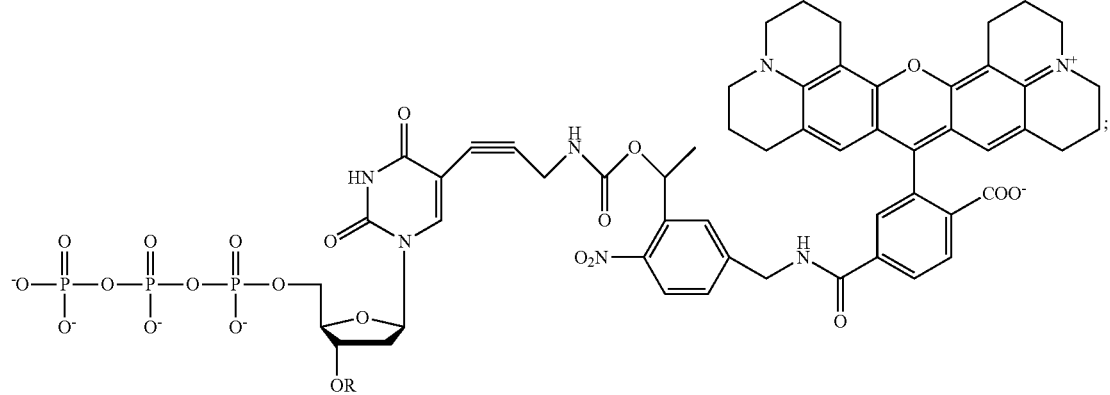

wherein R is —CH$_2$OCH$_3$ or —CH$_2$CH=CH$_2$.

In different embodiments, the nucleotide analogue is selected from the group consisting of:

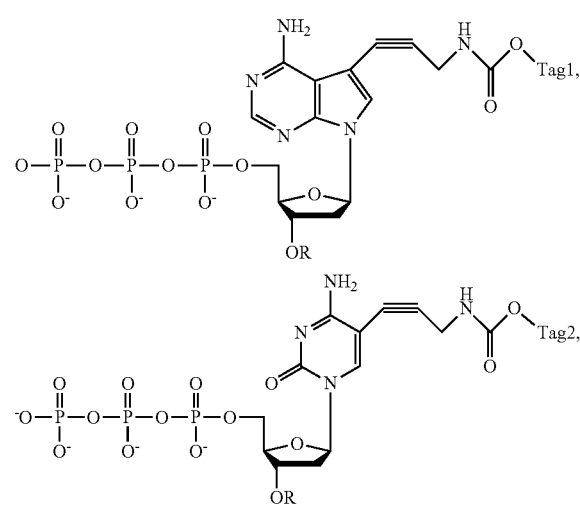

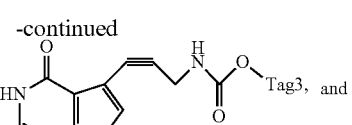

wherein Tag$_1$, Tag$_2$, Tag$_3$, and Tag$_4$ are four different mass tag labels; and wherein R is a cleavable chemical group used to cap the —OH group at the 3'-position of the deoxyribose.

In different embodiments, the nucleotide analogue is selected from the group consisting of:

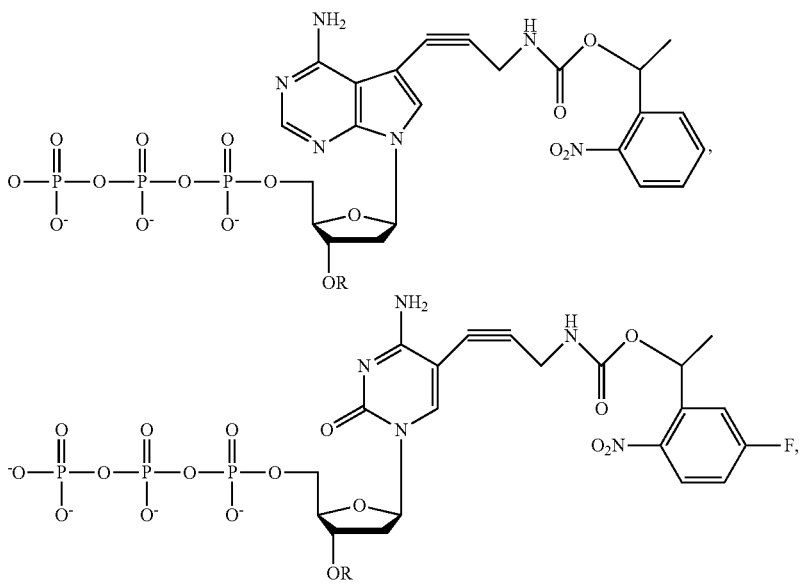

-continued

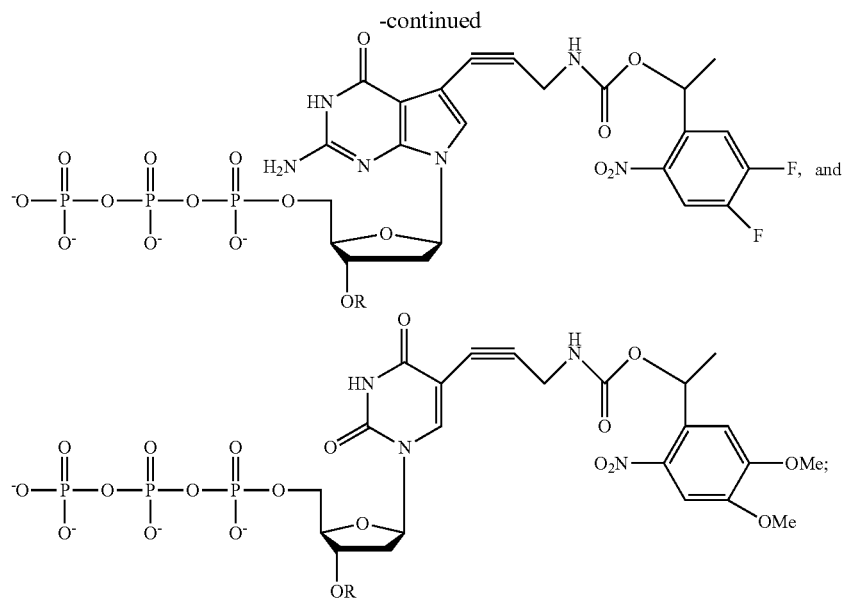

wherein R is —CH$_2$OCH$_3$ or —CH$_2$CH=CH$_2$.

The invention provides for the use any of the nucleotide analogues disclosed herein for detection of single nucleotide polymorphisms, genetic mutation analysis, serial analysis of gene expression, gene expression analysis, identification in forensics, genetic disease association studies, DNA sequencing, genomic sequencing, translational analysis, or transcriptional analysis.

The invention provides a parallel mass spectrometry system, which comprises a plurality of atmospheric pressure chemical ionization mass spectrometers for parallel analysis of a plurality of samples comprising mass tags. In one embodiment, the mass spectrometers are quadrupole mass spectrometers. In one embodiment, the mass spectrometers are time-of-flight mass spectrometers. In one embodiment, the mass spectrometers are contained in one device. In one embodiment, the system further comprises two turbopumps, wherein one pump is used to generate a vacuum and a second pump is used to remove undesired elements. In one embodiment, the system comprises at least three mass spectrometers. In one embodiment, the mass tags have molecular weights between 150 daltons and 250 daltons. The invention provides for the use of the system for DNA sequencing analysis, detection of single nucleotide polymorphisms, genetic mutation analysis, serial analysis of gene expression, gene expression analysis, identification in forensics, genetic disease association studies, DNA sequencing, genomic sequencing, translational analysis, or transcriptional analysis.

This invention will be better understood from the Experimental Details which follow. However, one skilled in the art will readily appreciate that the specific methods and results discussed are merely illustrative of the invention as described more fully in the claims which follow thereafter.

Experimental Details

1. The Sequencing by Synthesis Approach

Sequencing DNA by synthesis involves the detection of the identity of each nucleotide as it is incorporated into the growing strand of DNA in the polymerase reaction. The fundamental requirements for such a system to work are: (1) the availability of 4 nucleotide analogues (aA, aC, aG, aT) each labeled with a unique label and containing a chemical moiety capping the 3'-OH group; (2) the 4 nucleotide analogues (aA, aC, aG, aT) need to be efficiently and faithfully incorporated by DNA polymerase as terminators in the polymerase reaction; (3) the tag and the group capping the 3'-OH need to be removed with high yield to allow the incorporation and detection of the next nucleotide; and (4) the growing strand of DNA should survive the washing, detection and cleavage processes to remain annealed to the DNA template.

Figure 2A:
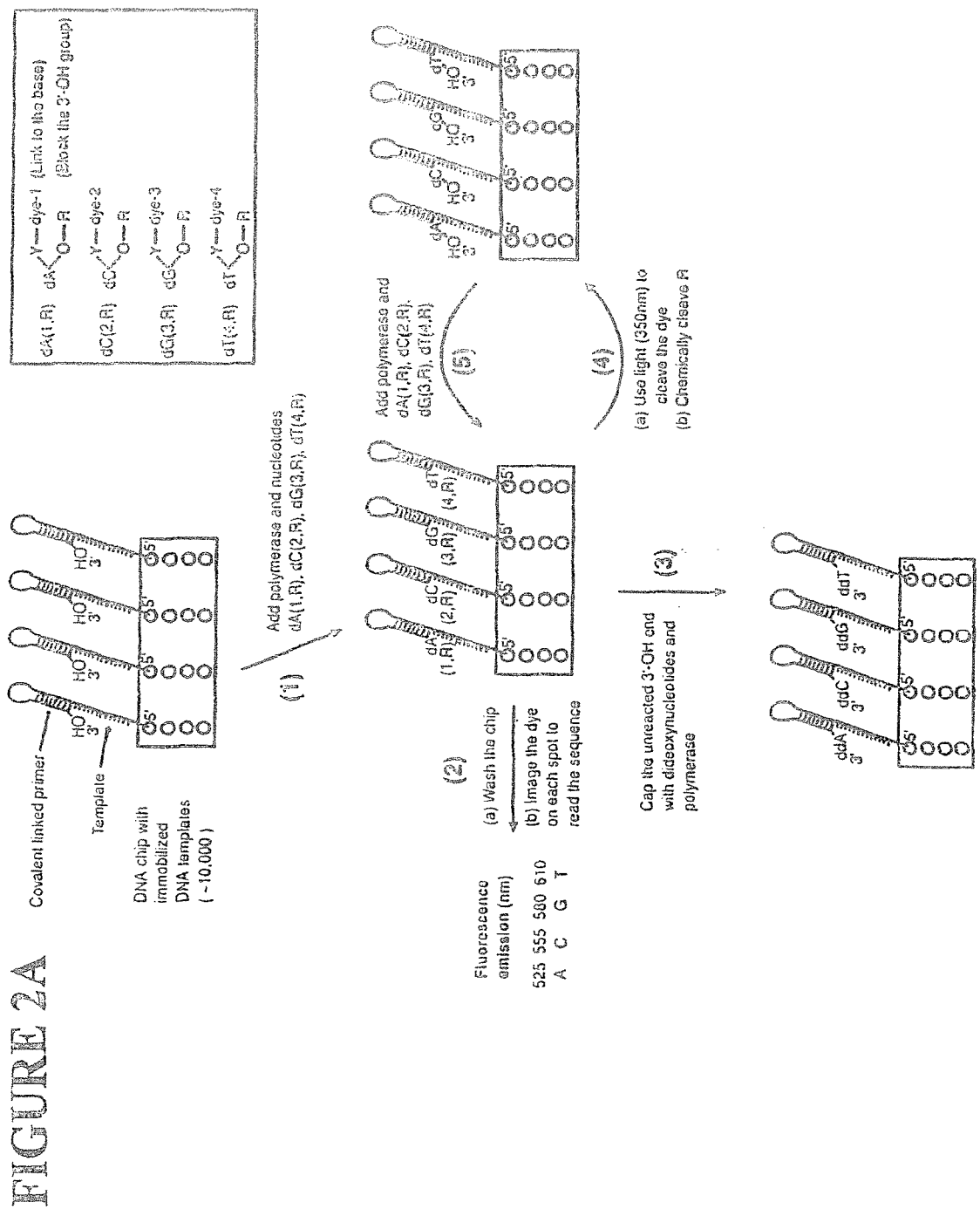
FIG. 2A-2B: Scheme of sequencing by the synthesis approach. A: Example where the unique labels are dyes and the solid surface is a chip. B: Example where the unique labels are mass tags and the solid surface is channels etched into a glass chip. A, C, G, T; nucleotide triphosphates comprising bases adenine, cytosine, guanine, and thymine; d, deoxy; dd, dideoxy; R, cleavable chemical group used to cap the —OH group; Y, cleavable linker.
Figure 2B:
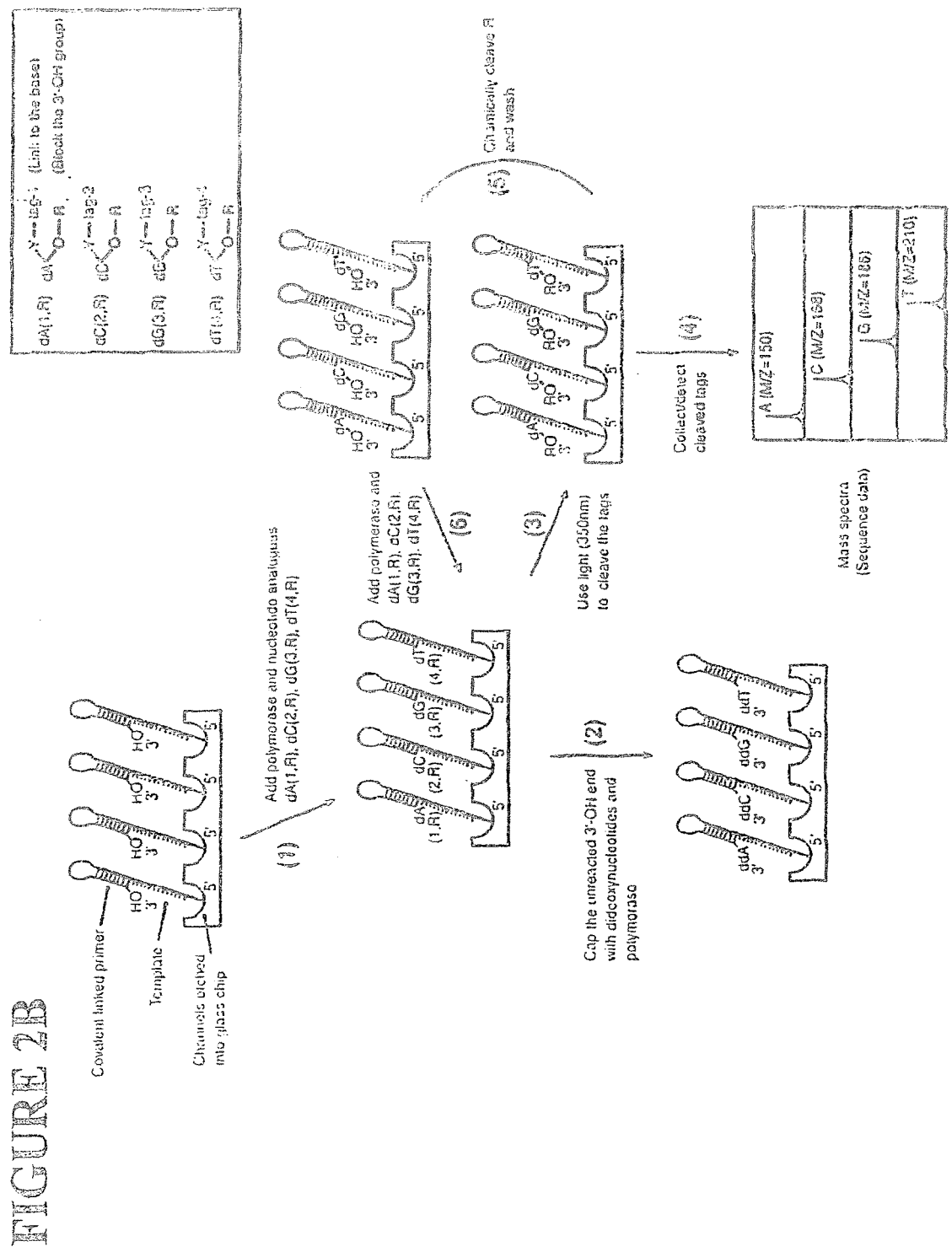

The sequencing by synthesis approach disclosed herein is illustrated in FIG. 2A-2B. In FIG. 2A, an example is shown where the unique labels are fluorescent dyes and the surface is a chip; in FIG. 2B, the unique labels are mass tags and the surface is channels etched into a chip. The synthesis approach uses a solid surface such as a glass chip with an immobilized DNA template that is able to self prime for initiating the polymerase reaction, and four nucleotide analogues (3'-RO-A-LABEL1, 3'-RO-C-LABEL2, 3'-RO-G-LABEL3, 3'-RO-T-LABEL4) each labeled with a unique label, e.g. a fluorescent dye or a mass tag, at a specific location on the purine or pyrimidine base, and a small cleavable chemical group (R) to cap the 3'-OH group. Upon adding the four nucleotide analogues and DNA polymerase, only one nucleotide analogue that is complementary to the next nucleotide on the template is incorporated by the polymerase on each spot of the surface (step 1 is FIGS. 2A and 2B).

As shown in FIG. 2A, where the unique labels are dyes, after removing the excess reagents and washing away any unincorporated nucleotide analogues on the chip, a detector is used to detect the unique label. For example, a four color fluorescence imager is used to image the surface of the chip, and the unique fluorescence emission from a specific dye on the nucleotide analogues on each spot of the chip will reveal the identity of the incorporated nucleotide (step 2 in FIG. 2A). After imaging, the small amount of unreacted 3'-OH group on the self-primed template moiety is capped by excess dideoxynucleoside triphosphates (ddNTPs) (ddATP, ddGTP, ddTTP, and ddCTP) and DNA polymerase to avoid interference with the next round of synthesis (step 3 in FIG. 2A), a concept similar to the capping step in automated solid phase DNA synthesis (Caruthers, 1985). The ddNTPs, which lack a 3'-hydroxyl group, are chosen to cap the unreacted 3'-OH of the nucleotide due to their small size compared with the dye-labeled nucleotides, and the excellent efficiency with which they are incorporated by DNA polymerase. The dye moiety is then cleaved by light (~350 nm), and the R group protecting the 3'-OH is removed chemically to generate free 3'-OH group with high yield (step 4 in FIG. 2A). A washing step is applied to wash away the cleaved dyes and the R group. The self-primed DNA moiety on the chip at this stage is ready for the next cycle of the reaction to identify the next nucleotide sequence of the template DNA (step 5 in FIG. 2A).

It is a routine procedure now to immobilize high density (>10,000 spots per chip) single stranded DNA on a 4 cm×1 cm glass chip (Schena et al. 1995). Thus, in the DNA sequencing system disclosed herein, more than 10,000 bases can be identified after each cycle and after 100 cycles, a million base pairs will be generated from one sequencing chip.

Possible DNA polymerases include Thermo Sequenase, Taq FS DNA polymerase, T7 DNA polymerase, and Vent (exo-) DNA polymerase. The fluorescence emission from each specific dye can be detected using a fluorimeter that is equipped with an accessory to detect fluorescence from a glass slide. For large scale evaluation, a multi-color scanning system capable of detecting multiple different fluorescent dyes (500 nm-700 nm) (GSI Lumonics ScanArray 5000 Standard Biochip Scanning System) on a glass slide can be used.

An example of the sequencing by synthesis approach using mass tags is shown in FIG. 2B. The approach uses a solid surface, such as a porous silica glass channels in a chip, with immobilized DNA template that is able to self prime for initiating the polymerase reaction, and four nucleotide analogues ($3'$-$_{RO}$-A-$_{Tag1}$, $3'$-$_{RO}$-C-$_{Tag2}$, $3'$-$_{RO}$-G-$_{Tag3}$, $3'$-$_{RO}$-T-$_{Tag4}$) each labeled with a unique photocleavable mass tag on the specific location of the base, and a small cleavable chemical group (R) to cap the 3'-OH group. Upon adding the four nucleotide analogues and DNA polymerase, only one nucleotide analogue that is complementary to the next nucleotide on the template is incorporated by polymerase in each channel of the glass chip (step 1 in FIG. 2B). After removing the excess reagents and washing away any unincorporated nucleotide analogues on the chip, the small amount of unreacted 3'-OH group on the self-primed template moiety is capped by excess ddNTPs (ddATP, ddGTP, ddTTP and ddCTP) and DNA polymerase to avoid interference with the next round of synthesis (step 2 in FIG. 2B). The ddNTPs are chosen to cap the unreacted 3'-OH of the nucleotide due to their small size compared with the labeled nucleotides, and their excellent efficiency to be incorporated by DNA polymerase. The mass tags are cleaved by irradiation with light (~350 nm) (step 3 in FIG. 2B) and then detected with a mass spectrometer. The unique mass of each tag yields the identity of the nucleotide in each channel (step 4 in FIG. 2B). The R protecting group is then removed chemically and washed away to generate free 3'-OH group with high yield (step 5 in FIG. 2B). The self-primed DNA moiety on the chip at this stage is ready for the next cycle of the reaction to identify the next nucleotide sequence of the template DNA (step 6 in FIG. 2B).

Since the development of new ionization techniques such as matrix assisted laser desorption ionization (MALDI) and electrospray ionization (ESI), mass spectrometry has become an indispensable tool in many areas of biomedical research. Though these ionization methods are suitable for the analysis of bioorganic molecules, such as peptides and proteins, improvements in both detection and sample preparation are required for implementation of mass spectrometry for DNA sequencing applications. Since the approach disclosed herein uses small and stable mass tags, there is no need to detect large DNA sequencing fragments directly and it is not necessary to use MALDI or ESI methods for detection. Atmospheric pressure chemical ionization (APCI) is an ionization method that uses a gas-phase ion-molecular reaction at atmospheric pressure (Dizidic et al. 1975). In this method, samples are introduced by either chromatography or flow injection into a pneumatic nebulizer where they are converted into small droplets by a high-speed beam of nitrogen gas. When the heated gas and solution arrive at the reaction area, the excess amount of solvent is ionized by corona discharge. This ionized mobile phase acts as the ionizing agent toward the samples and yields pseudo molecular $(M+H)^+$ and $(M-H)^-$ ions. Due to the corona discharge ionization method, high ionization efficiency is attainable, maintaining stable ionization conditions with detection sensitivity lower than femtomole region for small and stable organic compounds. However, due to the limited detection of large molecules, ESI and MALDI have replaced APCI for analysis of peptides and nucleic acids. Since in the approach disclosed the mass tags to be detected are relatively small and very stable organic molecules, the ability to detect large biological molecules gained by using ESI and MALDI is not necessary. APCI has several advantages over ESI and MALDI because it does not require any tedious sample preparation such as desalting or mixing with matrix to prepare crystals on a target plate. In ESI, the sample nature and sample preparation conditions (i.e. the existence of buffer or inorganic salts) suppress the ionization efficiency. MALDI requires the addition of matrix prior to sample introduction into the mass spectrometer and its speed is often limited by the need to search for an ideal irradiation spot to obtain interpretable mass spectra. These limitations are overcome by APCI because the mass tag solution can be injected directly with no additional sample purification or preparation into the mass spectrometer. Since the mass tagged samples are volatile and have small mass numbers, these compounds are easily detectable by APCI ionization with high sensitivity. This system can be scaled up into a high throughput operation.

Each component of the sequencing by synthesis system is described in more detail below.

2. Construction of a Surface Containing Immobilized Self-primed DNA Moiety

Figure 3:
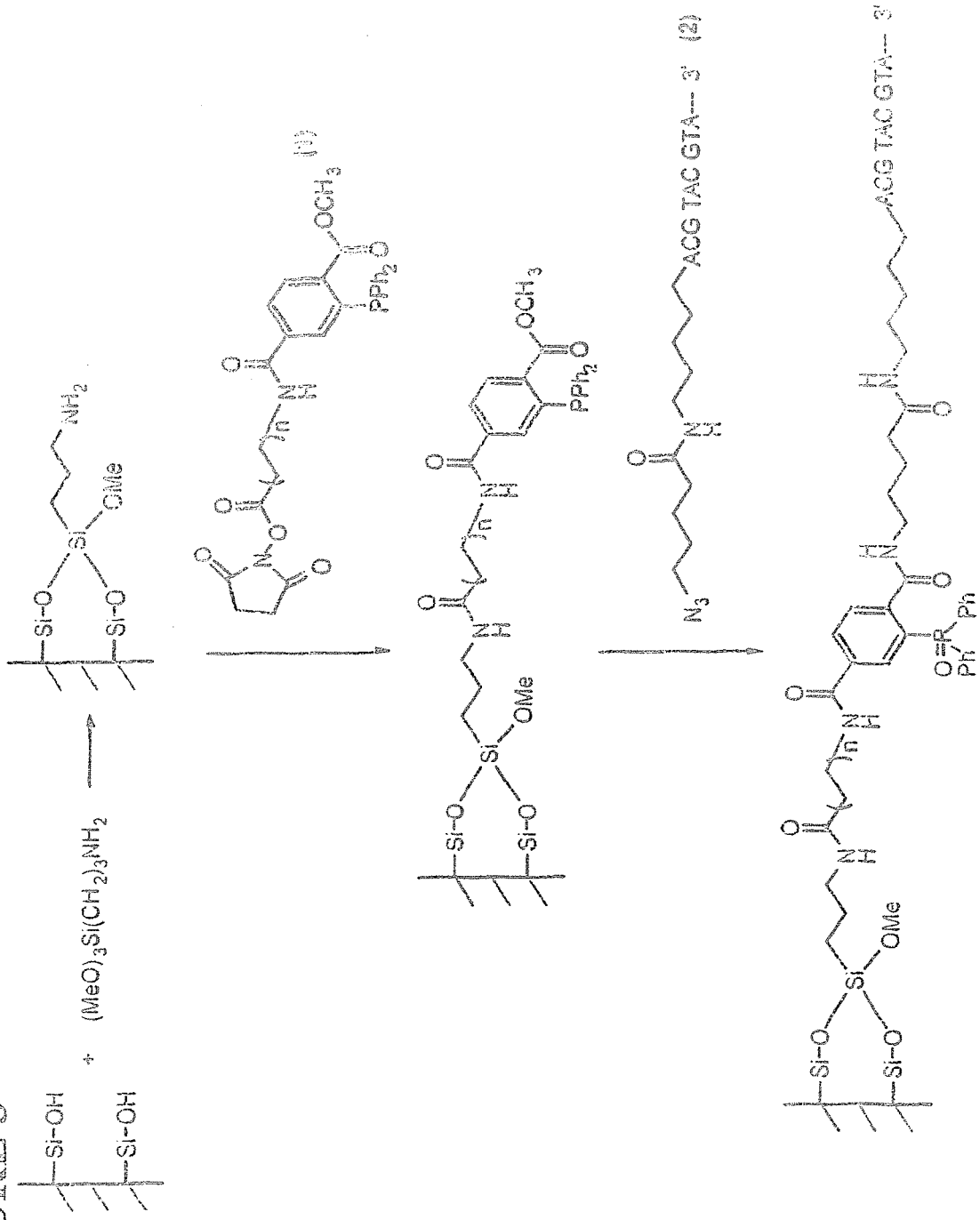
FIG. 3: The synthetic scheme for the immobilization of an azido ($N_3$) labeled DNA fragment to a solid surface coated with a triarylphosphine moiety. Me, methyl group; P, phosphorus; Ph, phenyl.

The single stranded DNA template immobilized on a surface is prepared according to the scheme shown in FIG. 3. The surface can be, for example, a glass chip, such as a 4 cm×1 cm glass chip, or channels in a glass chip. The surface is first treated with 0.5 M NaOH, washed with water, and then coated with high density 3-aminopropyltrimethoxysilane in aqueous ethanol (Woolley et al. 1994) forming a primary amine surface. N-Hydroxy Succinimidyl (NHS) ester of triarylphosphine (1) is covalently coupled with the primary amine group converting the amine surface to a novel triarylphosphine surface, which specifically reacts with DNA containing an azido group (2) forming a chip with immobilized DNA. Since the azido group is only located at the 5' end of the DNA and the coupling reaction is through the unique reaction of the triarylphosphine moiety with the azido group in aqueous solution (Saxon and Bertozzi 2000), such a DNA surface will provide an optimal condition for hybridization.

Figure 4:
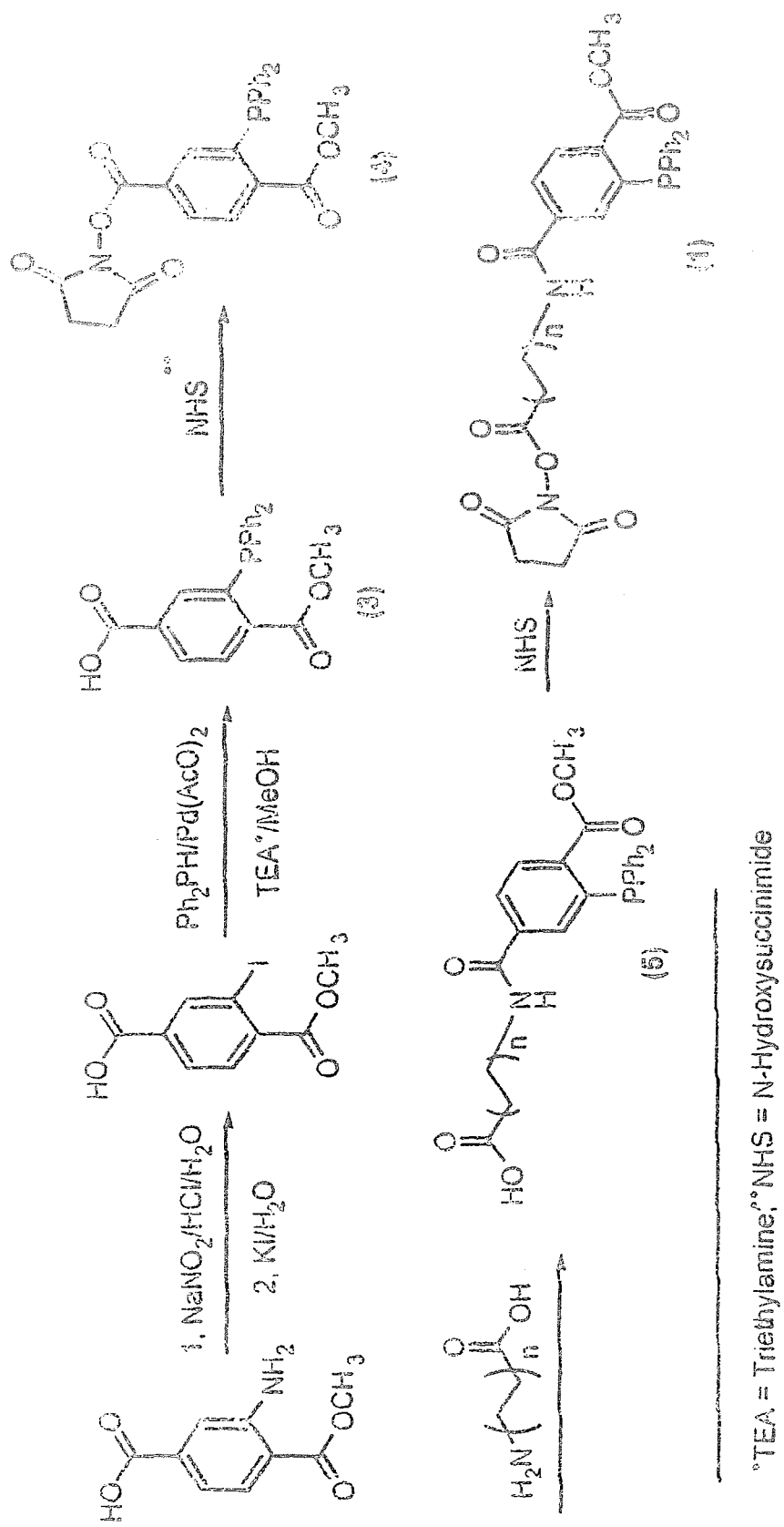
FIG. 4: The synthesis of triarylphosphine N-hydroxysuccinimide (NHS) ester.

The NHS ester of triarylphosphine (1) is prepared according to the scheme shown in FIG. 4. 3-diphenylphosphino-4-methoxycarbonyl-benzoic acid (3) is prepared according to the procedure described by Bertozzi et al. (Saxon and Bertozzi 2000). Treatment of (3) with N-Hydroxysuccinimide forms the corresponding NHS ester (4). Coupling of (4) with an amino carboxylic acid moiety produces compound (5) that has a long linker (n=1 to 10) for optimized coupling with DNA on the surface. Treatment of (5) with N-Hydroxysuccinimide generates the NHS ester (1) which is ready for coupling with the primary amine coated surface (FIG. 3).

Figure 5:
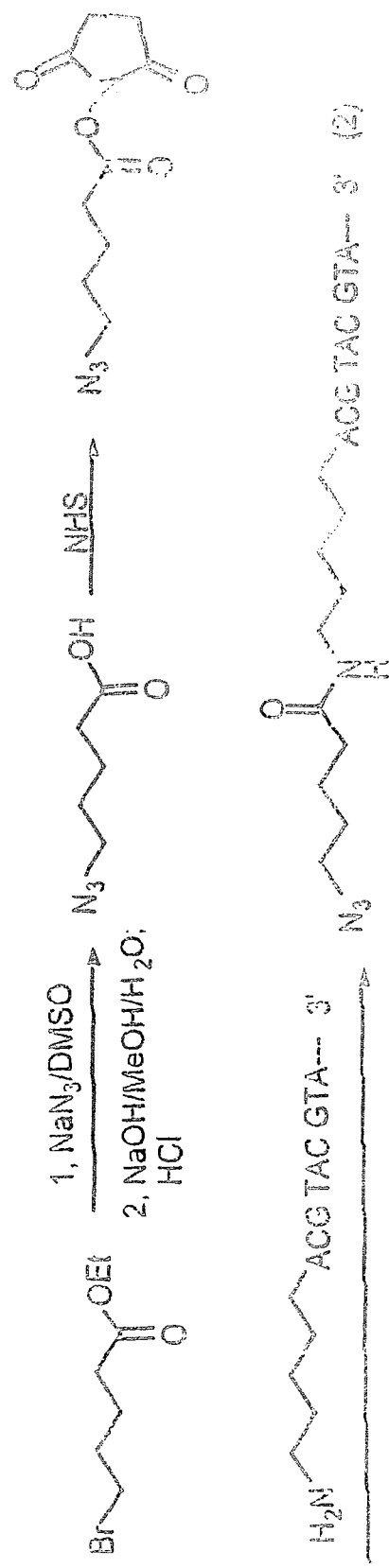
FIG. 5: The synthetic scheme for attaching an azido ($N_3$) group through a linker to the 5' end of a DNA fragment, which is then used to couple with the triarylphosphine moiety on a solid surface. DMSO, dimethylsulfonyl oxide.

The azido labeled DNA (2) is synthesized according to the scheme shown in FIG. 5. Treatment of ethyl ester of 5-bromovaleric acid with sodium azide and then hydrolysis produces 5-azidovaleric acid (Khoukhi et al., 1987), which is subsequently converted to a NHS ester for coupling with an amino linker modified oligonucleotide primer. Using the azido-labeled primer to perform polymerase chain reaction (PGR) reaction generates azido-labeled DNA template (2) for coupling with the triarylphosphine-modified surface (FIG. 3).

Figure 6A:
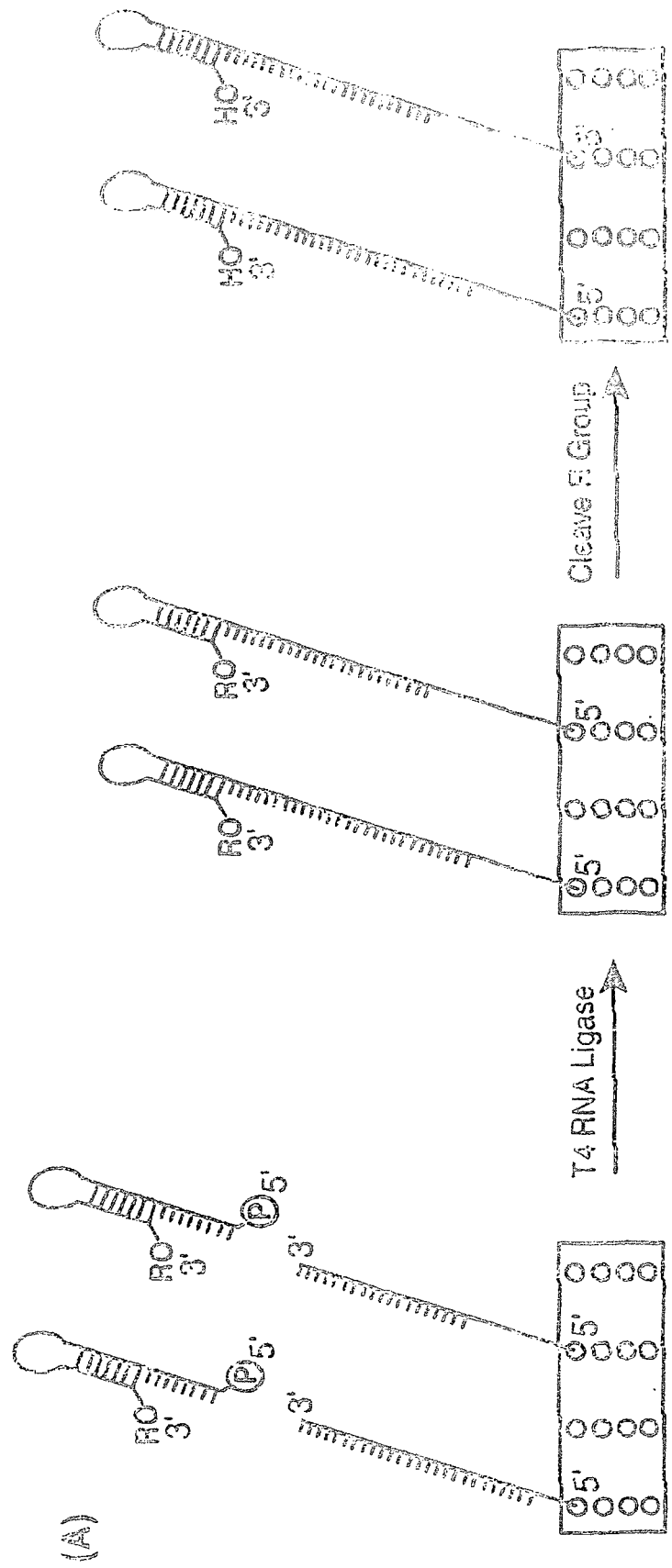
FIG. 6A-6B: Ligate the looped primer (B) to the immobilized single stranded DNA template forming a self-primed DNA template moiety on a solid surface. P (in circle), phosphate.
Figure 6B:
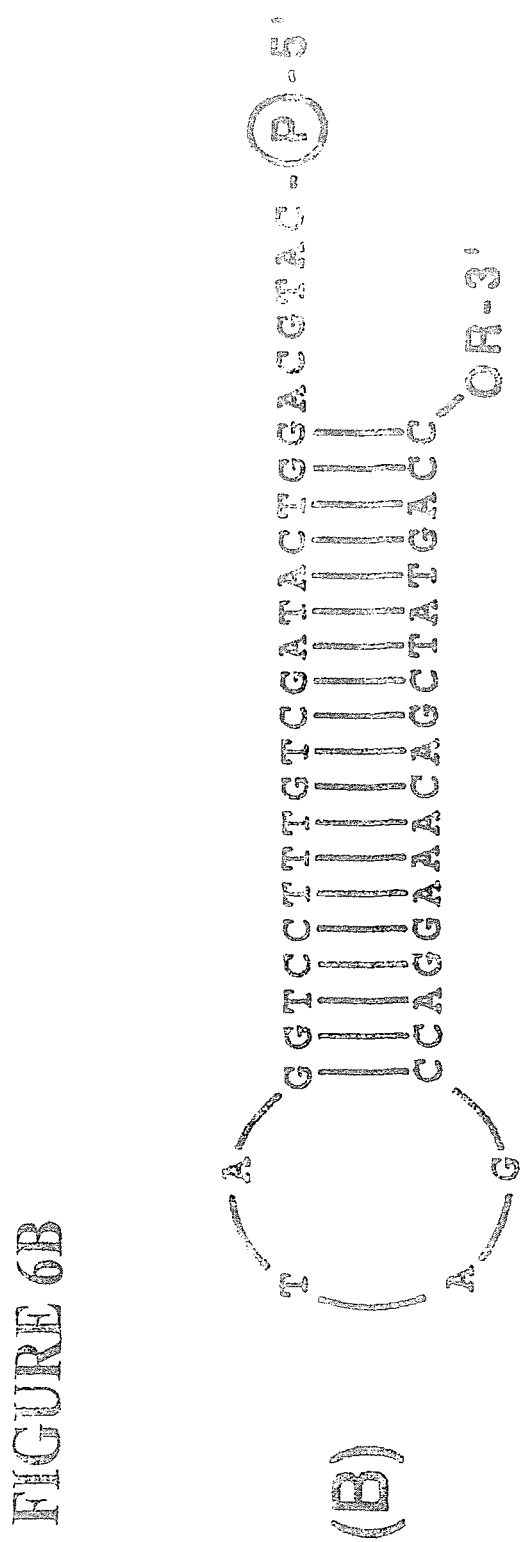

The self-primed DNA template moiety on the sequencing chip is constructed as shown in FIG. 6 (A & B) using enzymatic ligation. A 5'-phosphorylated, 3'-OH capped loop oligonucleotide primer (B) is synthesized by a solid phase DNA synthesizer. Primer (B) is synthesized using a modified C phosphoramidite whose 3'-OH is capped with either a MOM ($-CH_2OCH_3$) group or an allyl ($-CH_2CH=CH_2$) group (designated by "R" in FIG. 6) at the 3'-end of the oligonucleotide to prevent the self ligation of the primer in the ligation reaction. Thus, the looped primer can only ligate to the 3'-end of the DNA templates that are immobilized on the sequencing chip using T4 RNA ligase (Zhang et al. 1996) to form the self-primed DNA template moiety (A). The looped primer (B) is designed to contain a very stable loop (Antao et al. 1991) and a stem containing the sequence of M13 reverse DNA sequencing primer for efficient priming in the polymerase reaction once the p r i me r is ligated to the immobilized DNA on the sequencing chip and the 3'-OH cap group is chemically cleaved off (Ireland et al. 1986; Kamal et al. 1999).

Figure 7:
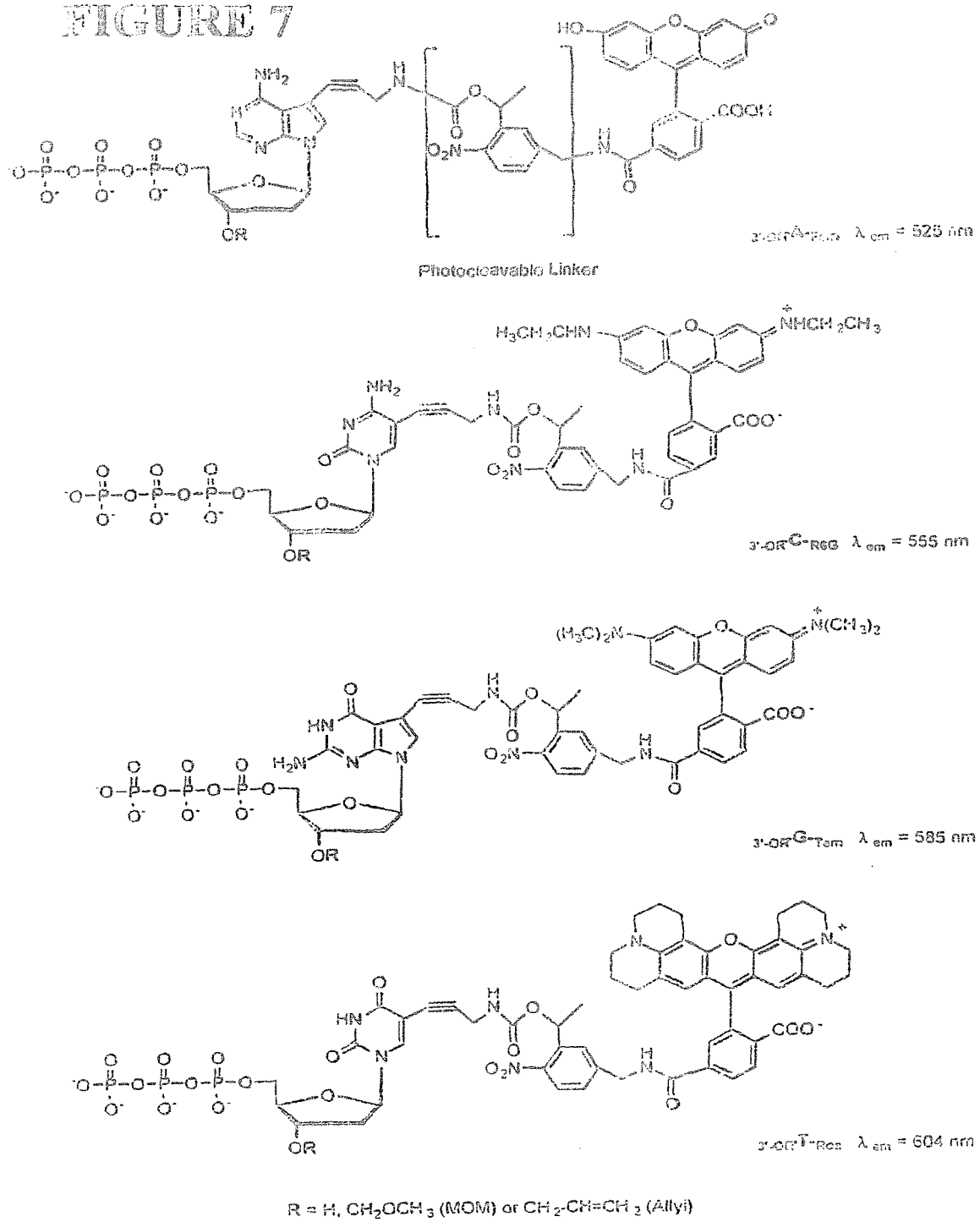
FIG. 7: Examples of structures of four nucleotide analogues for use in the sequencing by synthesis approach. Each nucleotide analogue has a unique fluorescent dye attached to the base through a photocleavable linker and the 3'-OH is either exposed or capped with a MOM group or an allyl group. FAM, 5-carboxyfluorescein; R6G, 6-carboxyrhodamine-6G; TAM, N,N,N',N'-tetramethyl-6-carboxyrhodamine; ROX, 6-carboxy-X-rhodamine. R=H, $CH_2OCH_3$ (MOM) or $CH_2CH=CH_2$(Allyl).

3. Sequencing by Synthesis Evaluation Using Nucleotide Analogpuos $_{3'-HO}$-A-$_{Dye1}$, $_{3'-HO}$—C—$_{Dye2}$, $_{3'-HO}$-G-$_{Dye3}$, $_{3'-HO}$-T-$_{Dye4}$ A scheme has been developed for evaluating the photocleavage efficiency using different dyes and testing the sequencing by synthesis approach. Four nucleotide analogues $_{3'-HO}$-A-$_{Dye1}$, $_{3'-HO}$—C—$_{Dye2}$, $_{3'-HO}$-G-$_{Dye3}$, $_{3'-HO}$-T=$_{Dye4}$ each labeled with a unique fluorescent dye through a photocleavable linker are synthesized and used in the sequencing by synthesis approach. Examples of dyes include, but are not limited to: Dye1=FAM, 5-carboxyfluorescein; Dye2=R6G, 6-carboxyrhodamine-6G; Dye3=TAM, N,N,N',N'-tetramethyl-6-carboxyrhodamine; and Dye 4=ROX, 6-carboxy-X-rhodamine. The structures of the 4 nucleotide analogues are shown in FIG. 7 (R=H).

The photocleavable 2-nitrobenzyl moiety has been used to link biotin to DNA and protein for efficient removal by UV light (~350 nm) (Olejnik et al. 1995, 1999). In the approach disclosed herein the 2-nitrobenzyl group is used to bridge the fluorescent dye and nucleotide together to form the dye labeled nucleotides as shown in FIG. 7.

Figure 8:
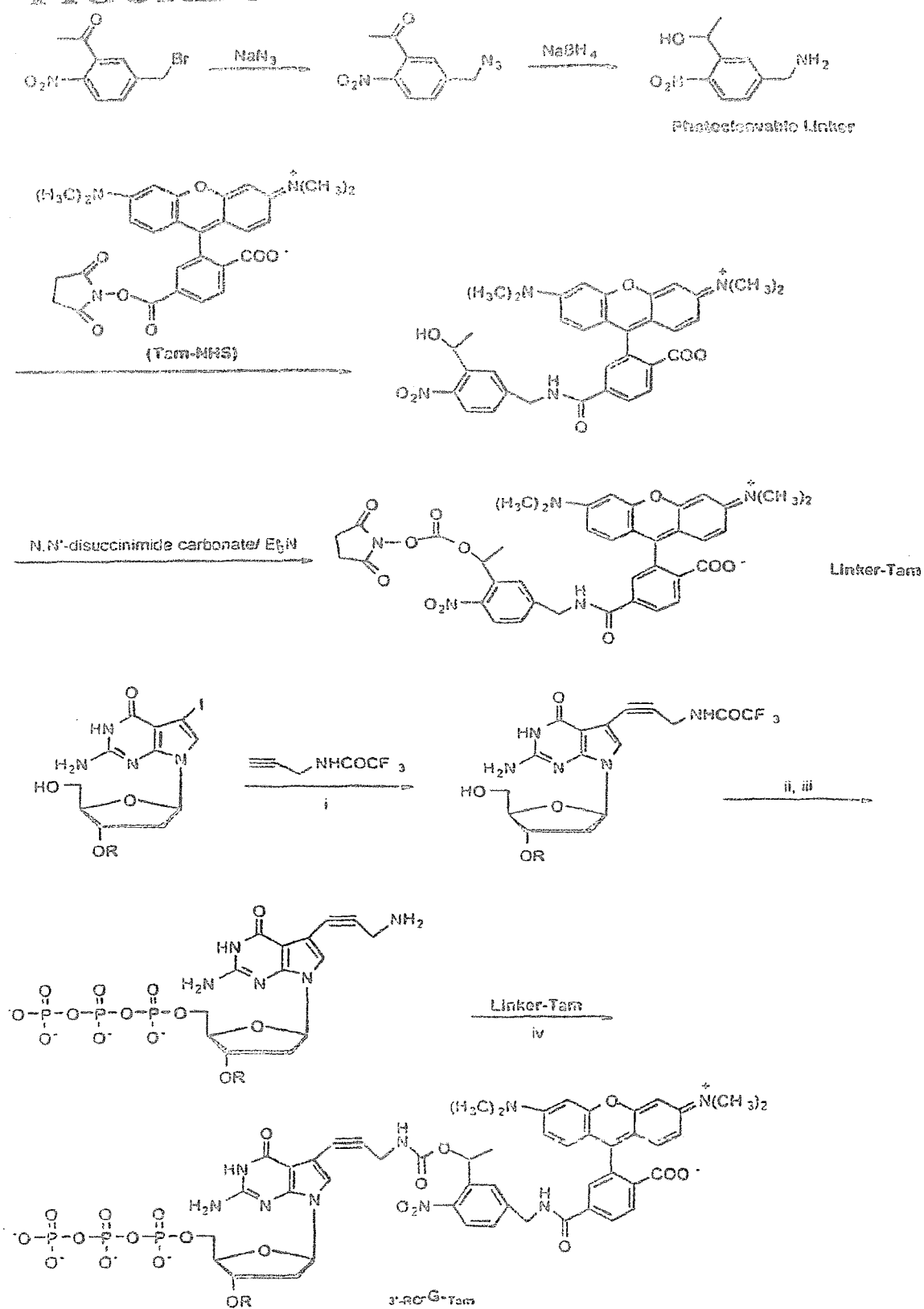
FIG. 8: A representative scheme for the synthesis of the nucleotide analogue $_{3'-RO}$-G-$_{Tam}$. A similar scheme can be used to create the other three modified nucleotides: $_{3'-RO}$-A-$_{Dye1}$, $_{3'-RO}$-C-$_{Dye2}$, $_{3'-RO}$-T-$_{Dye4}$. (i) tetrakis(triphenylphosphine)palladium(0); (ii) $POCl_3$, $Bn_4N^+$pyrophosphate; (iii) $NH_4OH$; (iv) $Na_2CO_3/NaHCO_3$ (pH=9.0)/DMSO.

As a representative example, the synthesis of $_{3'-HO}$-G-$_{Dye3}$ (Dye3=Tam) is shown in FIG. 8. 7-deaza-alkynylamino-dGTP is prepared using well-established procedures (Prober et al. 1987; Lee et al. 1992 and Hobbs et al. 1991). Linker-Tam is synthesized by coupling the Photocleavable Linker (Rollaf 1982) with NHS-Tam. 7-deaza-alkynylamino-dGTP is then coupled with the Linker-Tam to produce $_{3'-HO}$-G-$_{TAM}$. The nucleotide analogues with a free 3'-OH (i.e., R=H) are good substrates for the polymerase. An immobilized DNA template is synthesized (FIG. 9) that contains a portion of nucleotide sequence ACGTACGACGT (SEQ ID NO: 1) that has no repeated sequences after the priming site. $_{3'-HO}$-A-$_{Dye1}$ and DNA polymerase are added to the self-primed DNA moiety and it is incorporated to the 3' site of the DNA. Then the steps in FIG. 2A are followed (the chemical cleavage step is not required here because the 3'-OH is free) to detect the fluorescent signal from Dye-1 at 520 nm. Next, $_{3'-HO}$—C—$_{Dye2}$ is added to image the fluorescent signal from Dye-2 at 550 nm. Next, $_{3'-HO}$-G-$_{Dye3}$ is added to image the fluorescent signal from Dye-3 at 580 nm, and finally $_{3'-HO}$-T-$_{Dye4}$ is added to image the fluorescent signal from Dye-4 at 610 nm.

Results on Photochemical Cleavage Efficiency

Figure 10:
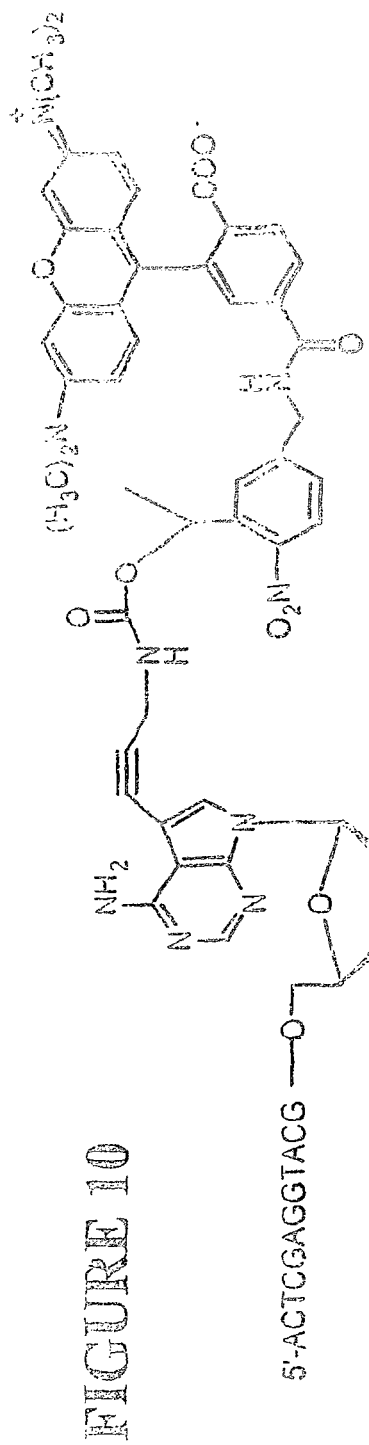
FIG. 10: The expected photocleavage products of DNA containing a photo-cleavable dye (Tam). Light absorption (300-360 nm) by the aromatic 2-nitrobenzyl moiety causes reduction of the 2-nitro group to a nitroso group and an oxygen insertion in to the carbon-hydrogen bond located in the 2-position followed by cleavage and decarboxylation (Pillai 1980).
Figure 10:
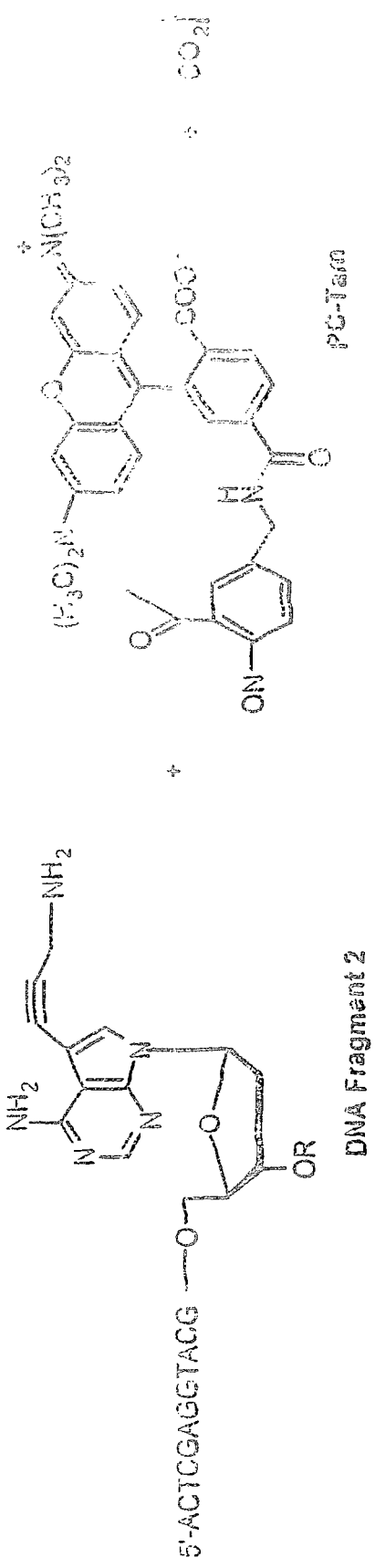

The expected photolysis products of DNA containing a photocleavable fluorescent dye at the 3' end of the DNA are shown in FIG. 10. The 2-nitrobenzyl moiety has been successfully employed in a wide range of studies as a photocleavable-protecting group (Pillai 1980). The efficiency of the photocleavage step depends on several factors including the efficiency of light absorption by the 2-nitrobenzyl moiety, the efficiency of the primary photochemical step, and the efficiency of the secondary thermal processes which lead to the final cleavage process (Turro 1991). Burgess et al. (1997) have reported the successful photocleavage of a fluorescent dye attached through a 2-nitrobenzyl linker on a nucleotide moiety, which shows that the fluorescent dye is not quenching the photocleavage process. A photoliable protecting group based on the 2-nitrobenzyl chromophore has also been developed for biological labeling applications that involve photocleavage (Olejnik et al. 1999). The protocol disclosed herein is used to optimize the photocleavage process shown in FIG. 10. The absorption spectra of 2-nitro benzyl compounds are examined and compared quantitatively to the absorption spectra of the fluorescent dyes. Since there will be a one-to-one relationship between the number of 2-nitrobenzyl moieties and the dye molecules, the ratio of extinction coefficients of these two species will reflect the competition for light absorption at specific wavelengths. From this information, the wavelengths at which the 2-nitrobenzyl moieties absorbed most competitively can be determined, similar to the approach reported by Olejnik et al. (1995).

A photolysis setup can be used which allows a high throughput of monochromatic light from a 1000 watt high pressure xenon lamp (LX1000UV, ILC) in conjunction with a monochromator (Kratos, Schoeffel Instruments). This instrument allows the evaluation of the photocleavage of model systems as a function of the intensity and excitation wavelength of the absorbed light. Standard analytical analysis is used to determine the extent of photocleavage. From this information, the efficiency of the photocleavage as a function of wavelength can be determined. The wavelength at which photocleavage occurs most efficiently can be selected as for use in the sequencing system.

Figure 11:
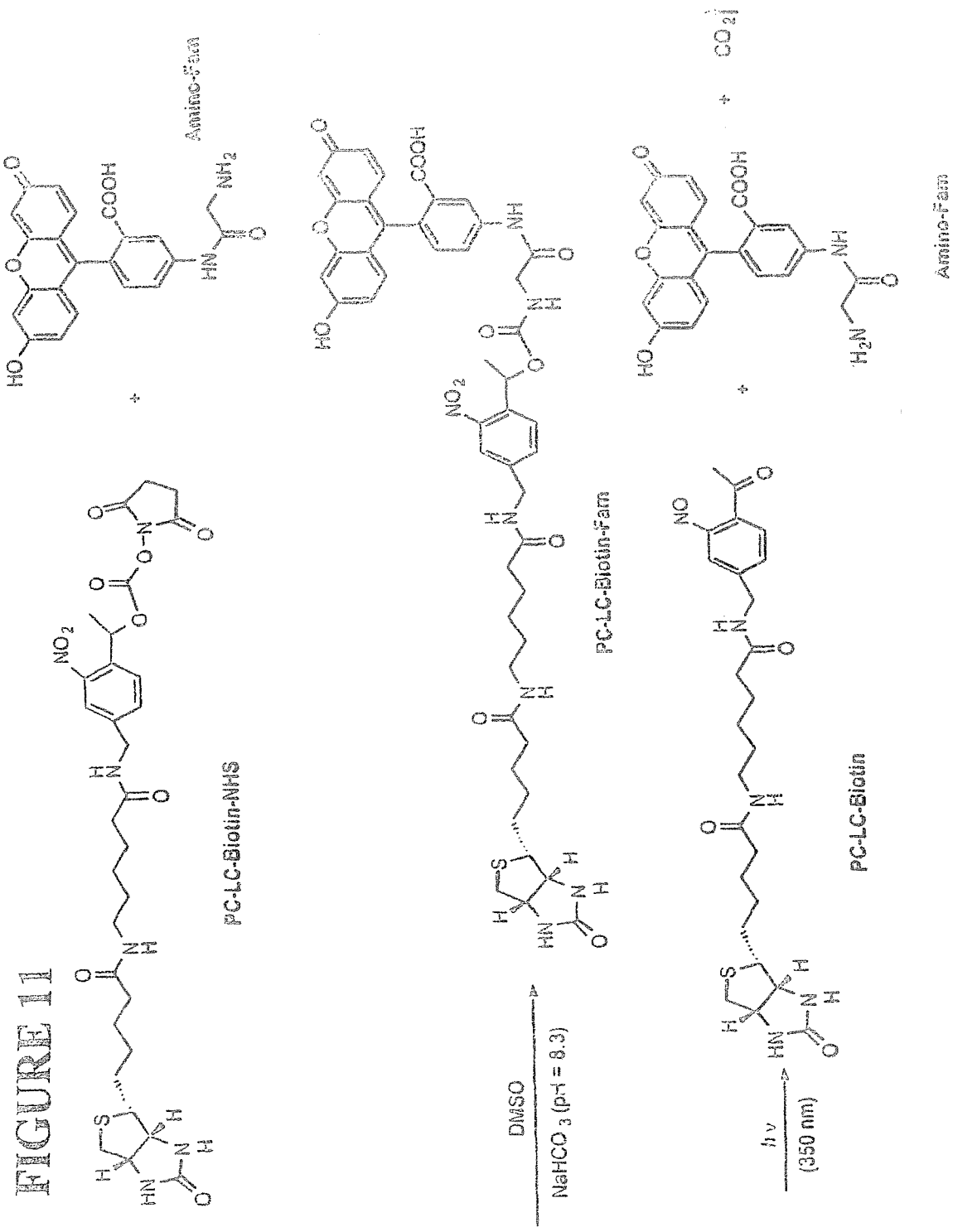
FIG. 11: Synthesis of PC-LC-Biotin-FAM to evaluate the photolysis efficiency of the fluorophore coupled with the photocleavable linker 2-nitrobenzyl group.
Figure 12:
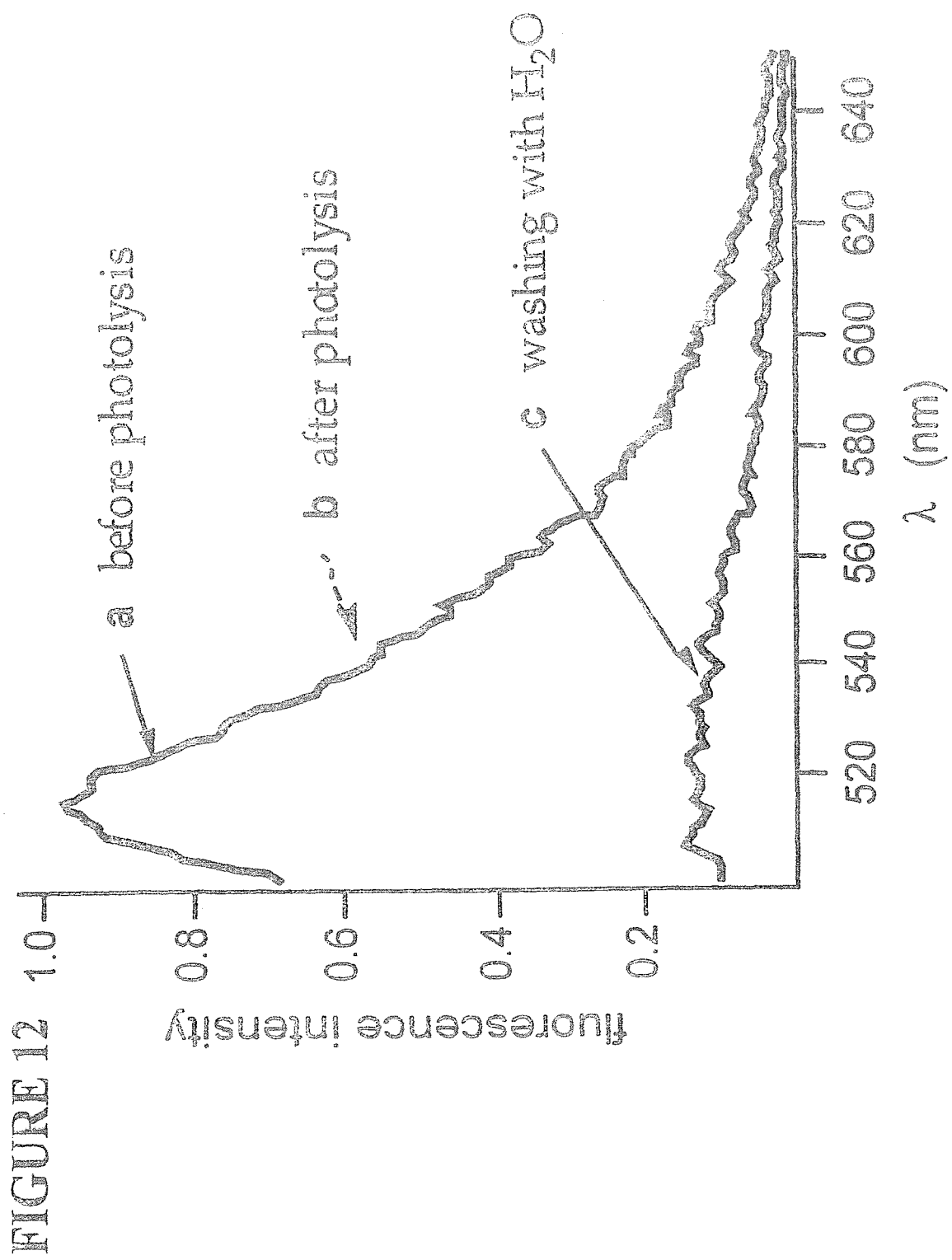
FIG. 12: Fluorescence spectra ($\lambda_{ex}$=480 nm) of PC-LC-Biotin-FAM immobilized on a microscope glass slide coated with streptavidin (a); after 10 min photolysis ($\lambda_{irr}$=350 nm; ~0.5 mW/cm$^2$) (b); and after washing with water to remove the photocleaved dye (c).

Photocleavage results have been obtained using a model system as shewn in FIG. 11. Coupling of PC-LC-Biotin-NHS ester (Pierce, Rockford Ill.) with 5-(aminoacetamido)-fluorescein (5-aminoFAM) (Molecular Probes, Eugene Oreg.) in dimethylsulfonyl oxide (DMSO)/NaHCO$_3$ (pH=8.2) overnight at room temperature produces PC-LC-Biotin-FAM which is composed of a biotin at one end, a photocleavable 2-nitrobenzyl group in the middle, and a dye tag (FAM) at the other end. This photocleavable moiety closely mimics the designed photocleavable nucleotide analogues shown in FIG. 10. Thus the successful photolysis of the PC-LC-Biotin-FAM moiety provides proof of the principle of high efficiency photolysis as used in the DNA sequencing system. For photolysis study, PC-LC-Biotin-FAM is first immobilized on a microscope glass slide coated with streptavidin (XENOPORE, Hawthorne N.J.). After washing off the non-immobilized PC-LC-Biotin-FAM, the fluorescence emission spectrum of the immobilized PC-LC-Biotin-FAM was taken as shown in FIG. 12 (Spectrum a). The strong fluorescence emission indicates that PC-LC-Biotin-FAM is successfully immobilized to the streptavidin coated slide surface. The photocleavability of the 2-nitrobenzyl linker by irradiation at 350 nm was then tested. After 10 minutes of photolysis ($\lambda_{irr}$=350 nm; ~0.5 mW/cm$^2$) and before any washing, the fluorescence emission spectrum of the same spot on the slide was taken that showed no decrease in intensity (FIG. 12, Spectrum b), indicating that the dye (FAM) was not bleached during the photolysis process at 350 nm. After washing the glass slide with HPLC water following photolysis, the fluorescence emission spectrum of the same spot on the slide showed significant intensity decrease (FIG. 12, Spectrum c) which indicates that most of the fluorescence dye (FAM) was cleaved from the immobilized biotin moiety and was removed by the washing procedure. This experiment shows that high efficiency cleavage of the fluorescent dye can be obtained using the 2-nitrobenzyl photocleavable linker.

Figure 13A:
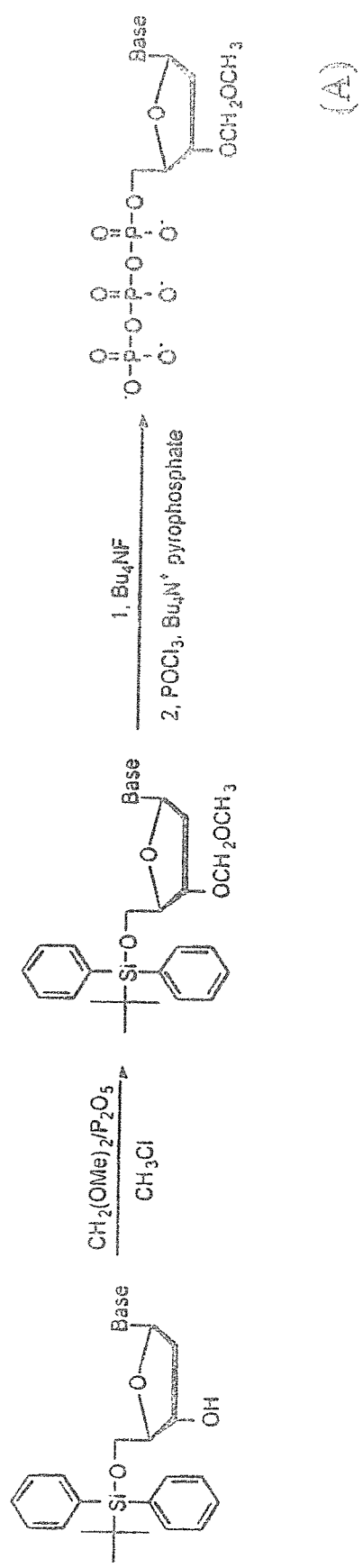
FIG. 13A-13B: Synthetic scheme for capping the 3'-OH of nucleotide.
Figure 13B:
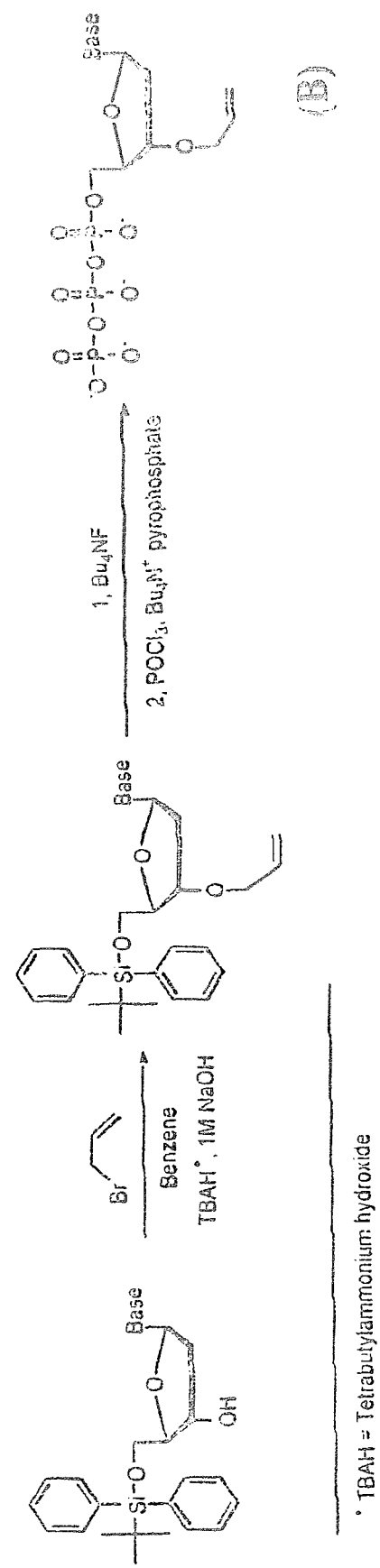
Figure 14:
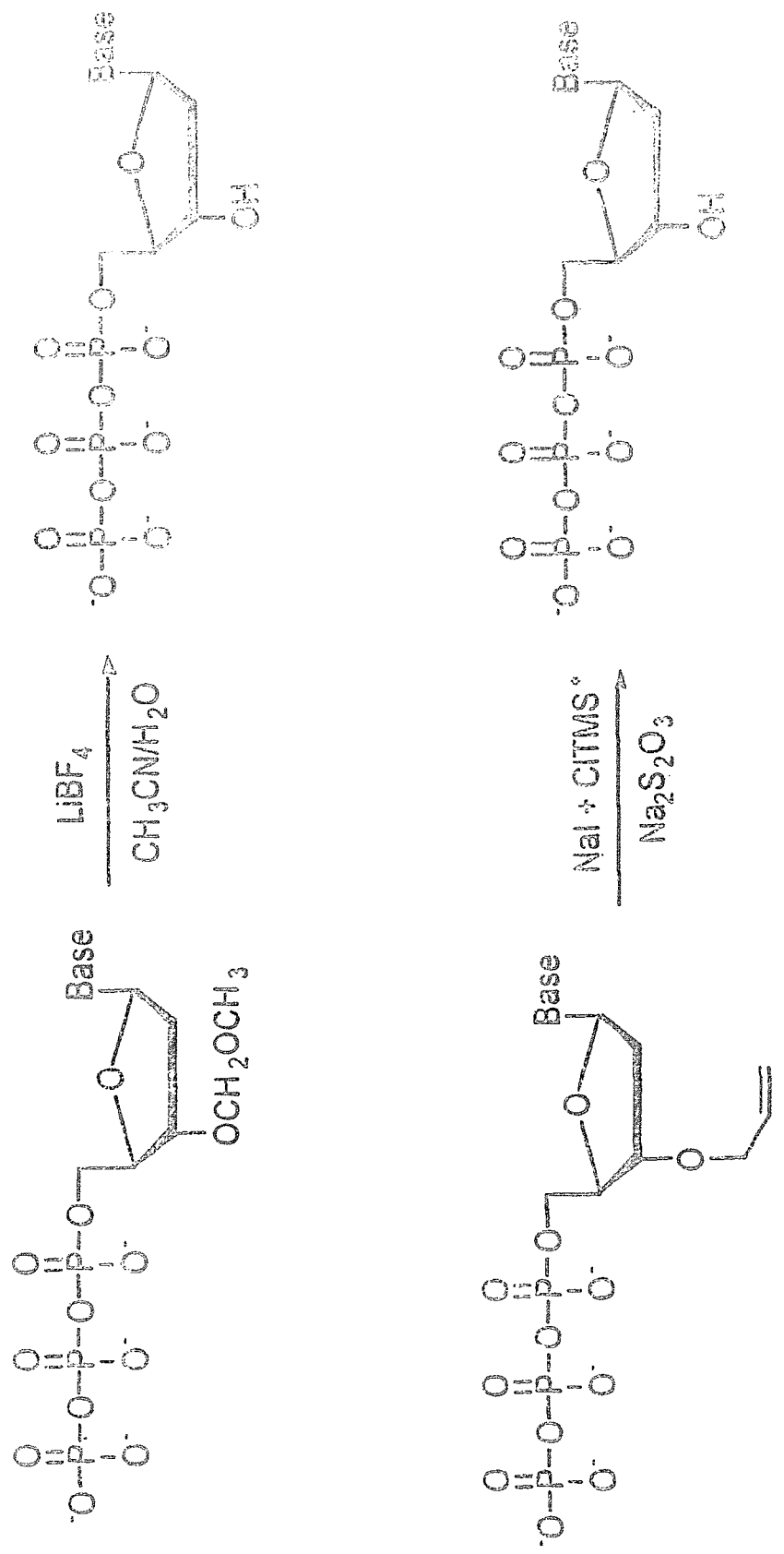
FIG. 14: Chemical cleavage of the MOM group (top row) and the allyl group (bottom row) to free the 3'-OH in the nucleotide. CITMS=chlorotrimethylsilane.

4. Sequencing by Synthesis Evaluation Using Nucleotide Analogues $_{3'-RO}$-A-$_{Dye1}$, $_{3'-RO}$—C—$_{Dye2}$, $_{3'-RO}$-G-$_{Dye3}$, $_{3'-RO}$-T-$_{Dye4}$ Once the steps and conditions in Section 3 are optimized, the synthesis of nucleotide analogues $_{3'-RO}$-A-$_{Dye1}$, $_{3'-RO}$—C—$_{Dye2}$, $_{3'-RO}$-G-$_{Dye3}$, $_{3'-RO}$-T-$_{Dye4}$ can be pursued for further study of the system. Here the 3'-OH is capped in all four nucleotide analogues, which then can be mixed together with DNA polymerase and used to evaluate the sequencing system using the scheme in FIG. 9. The MOM (—CH$_2$OCH$_3$) or allyl (—CH$_2$CH=CH$_2$) group is used to cap the 3'-OH group using well-established synthetic procedures (FIG. 13) (Fuji et al. 1975, Metzker et al. 1994). These groups can be removed chemically with high yield as shown in FIG. 14 (Ireland, et al. 1986; Kamal et al. 1999). The chemical cleavage of the MOM and allyl groups is fairly mild and specific, so as not to degrade the DNA template moiety. For example, the cleavage of the allyl group takes 3 minutes with more than 93% yield (Kamal et al. 1999), while the MOM group is reported to be cleaved with close to 100% yield (Ireland, et al. 1986).

Figure 15A:
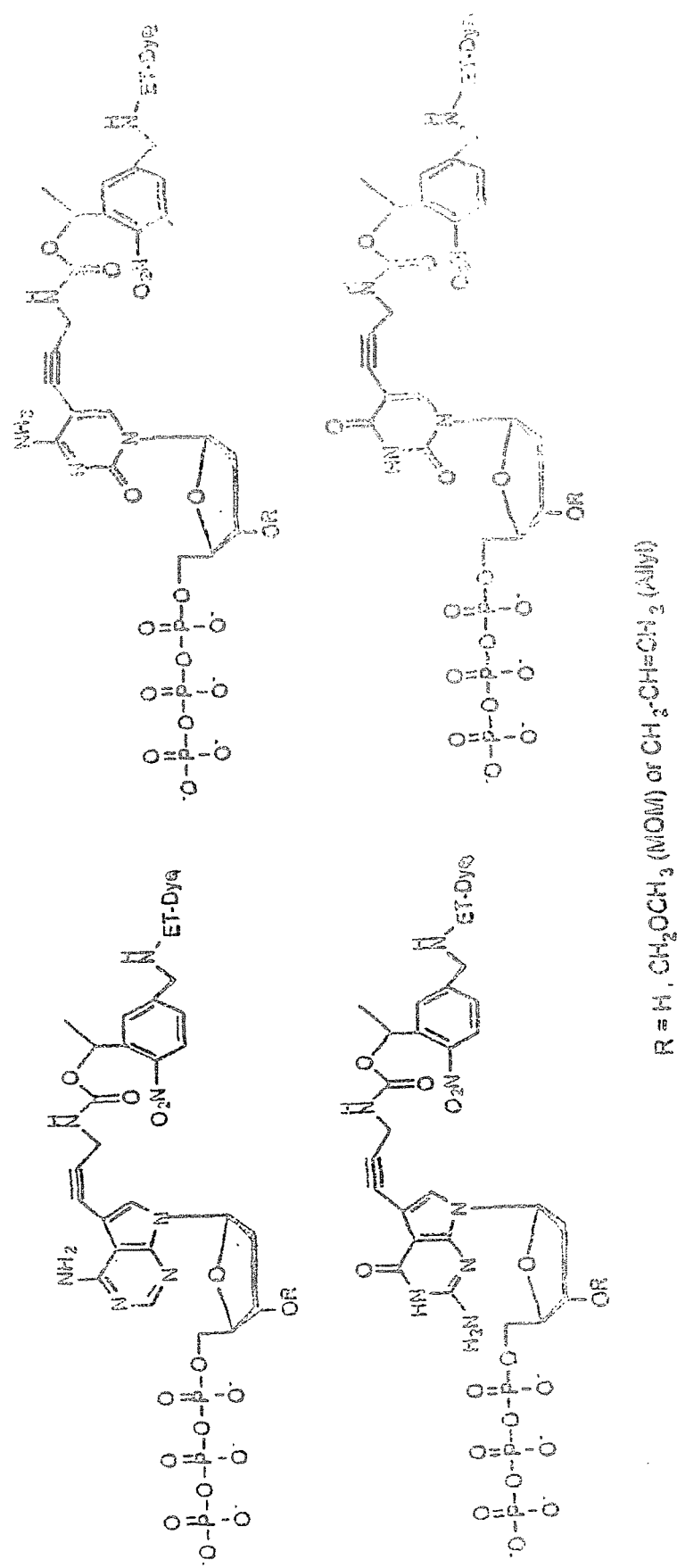
FIG. 15A-15B: Examples of energy transfer coupled dye systems, where Fam or Cy2 is employed as a light absorber (energy transfer donor) and $Cl_2$Fam, $Cl_2$R6G, $Cl_2$Tam, or $Cl_2$Rox as an energy transfer acceptor. Cy2, cyanine; FAM, 5-carboxyfluorescein; R6G, 6-carboxyrhodamine-6G; TAM, N,N,N',N'-tetramethyl-6-carboxyrhodamine; ROX, 6-carboxy-X-rhodamine.
Figure 15B:
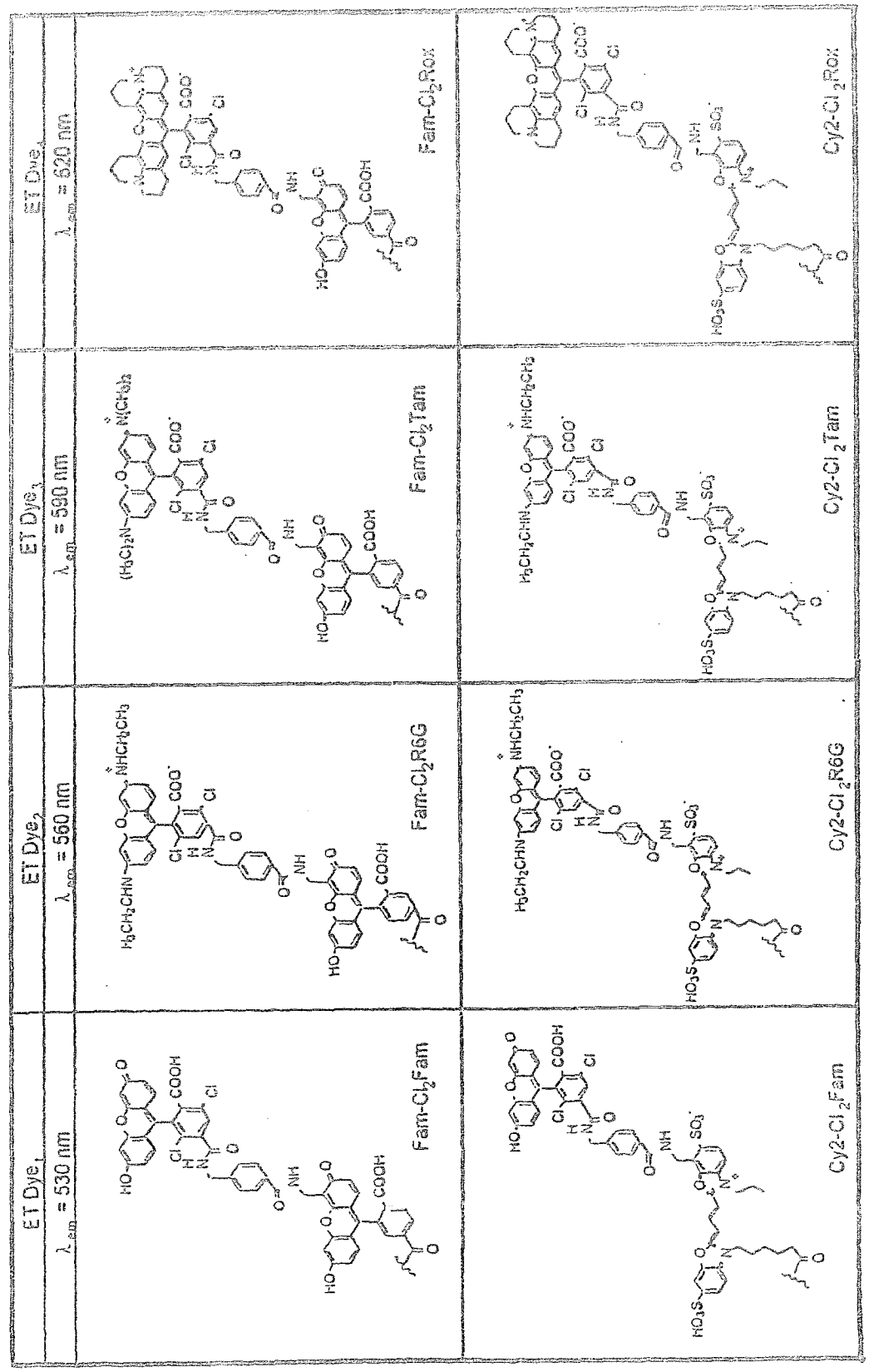
Figure 16:
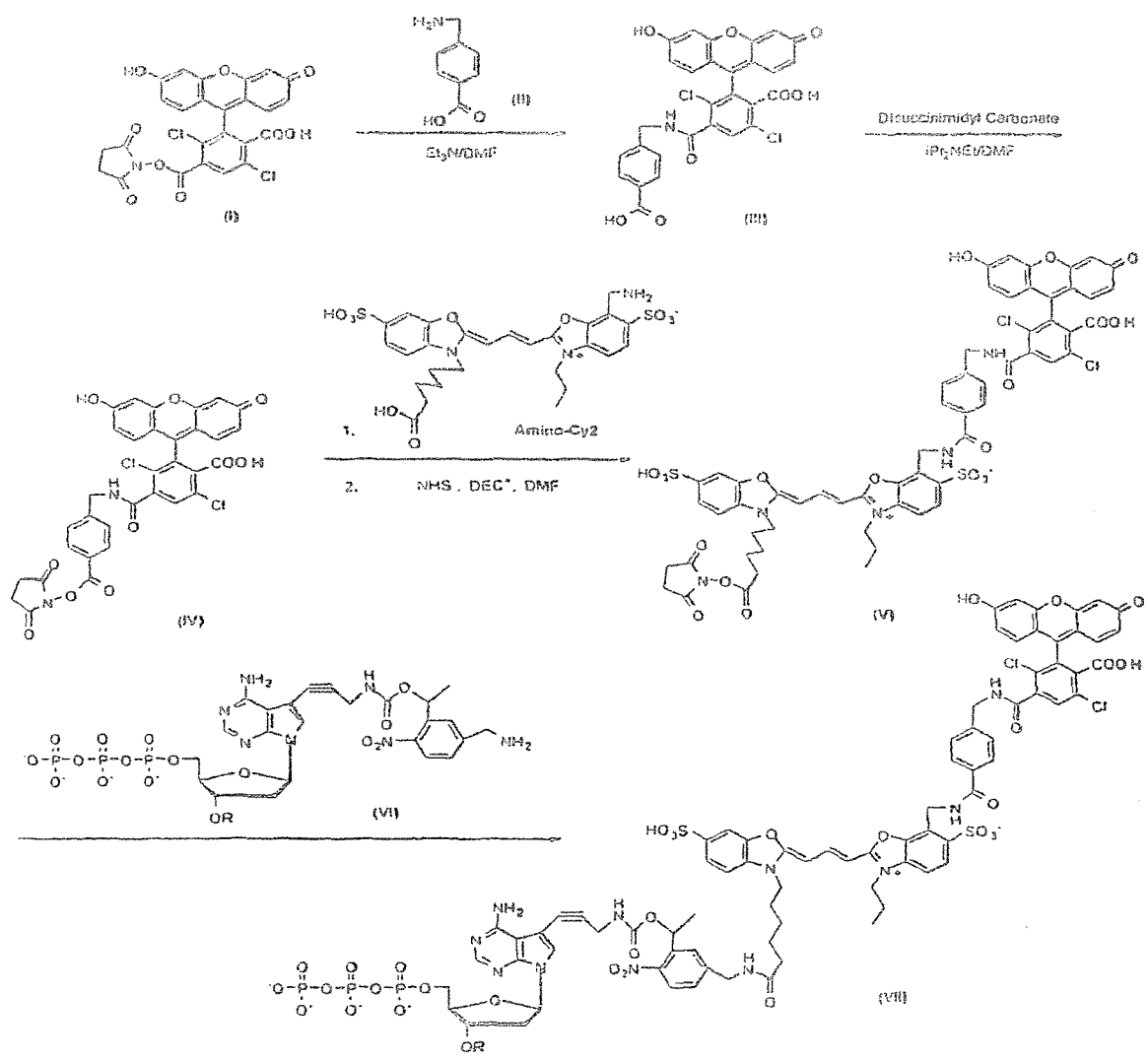
FIG. 16: The synthesis of a photocleavable energy transfer dye-labeled nucleotide. DMF, dimethylformide. DEC=1-(3-dimethylaminopropyl)-3-ethylcarbodimide hydrochloride. R=H, $CH_2OCH_3$ (MOM) or $CH_2CH=CH_2$ (Allyl).
Figure 18:
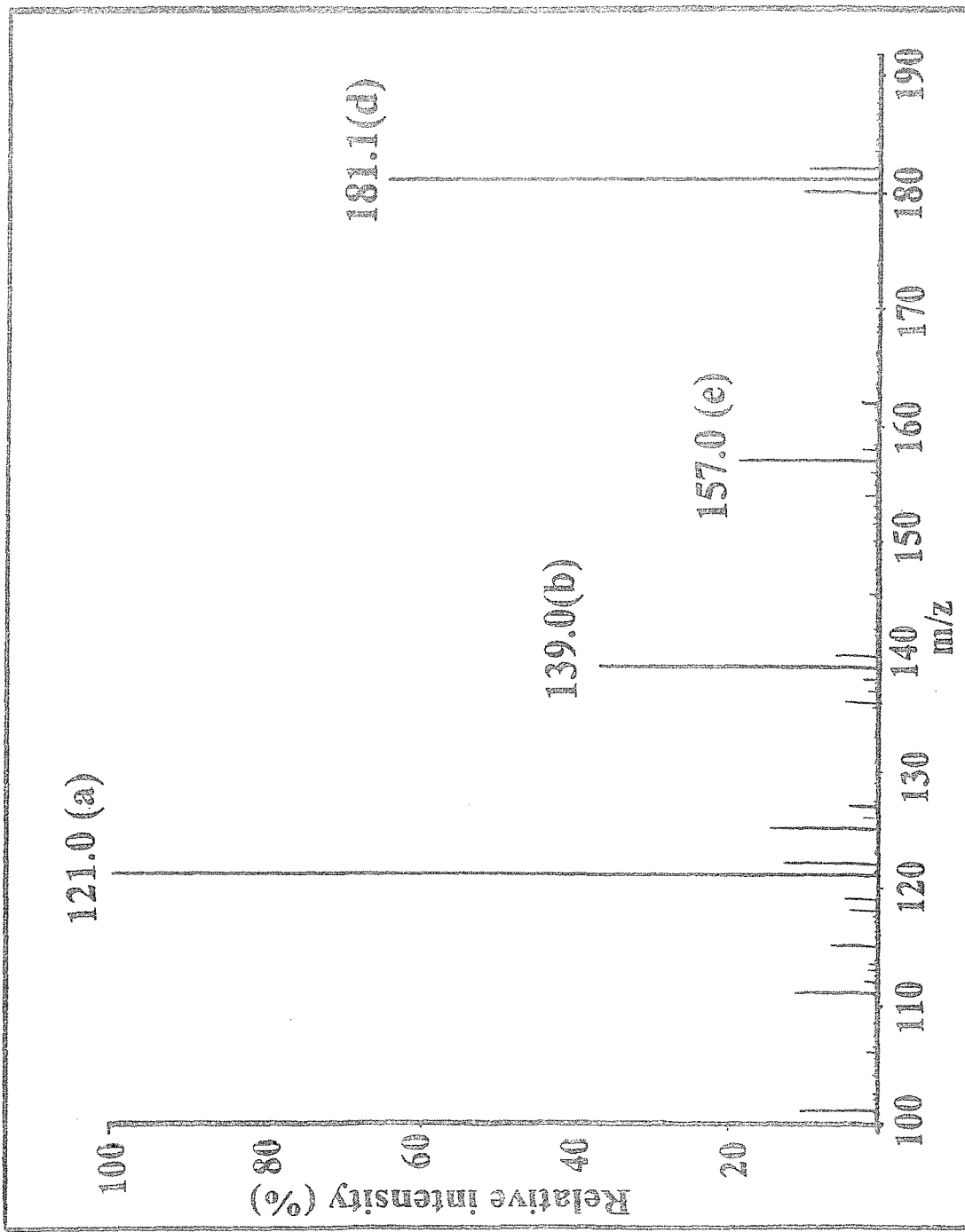
FIG. 18: Atmospheric. Pressure Chemical Ionization (APCI) mass spectrum of mass tag precursors shown in FIG. 17.

5. Using Energy Transfer Coupled Dyes To Optimize The Sequencing By Synthesis System The spectral property of the fluorescent tags can be optimized by using energy transfer (ET) coupled dyes. The ET primer and ET dideoxynucleotides have been shown to be a superior set of reagents for 4-color DNA sequencing that allows the use of one laser to excite multiple sets of fluorescent tags (Ju et al. 1995). It has been shown that DNA polymerase (Thermo Sequenase and Taq FS) can efficiently incorporate the ET dye labeled dideoxynucleotides (Rosenblum et al. 1997). These ET dye-labeled sequencing reagents are now widely used in large scale DNA sequencing projects, such as the human genome project. A library of ET dye labeled nucleotide analogues can be synthesized as shown in FIG. 15 for optimization of the DNA sequencing system. The ET dye set (FAM-Cl$_2$FAM, FAM-Cl$_2$R6G, FAM-Cl$_2$TAM, FAM-Cl$_2$ROX) using FAM as a donor and dichloro (FAM, R6G, TAM, ROX) as acceptors has been reported in the literature (Lee et al. 1997) and constitutes a set of commercially available DNA sequencing reagents. These ET dye sets have been proven to produce enhanced fluorescence intensity, and the nucleotides labeled with these ET dyes at the 5-position of T and C and the 7-position of G and A are excellent substrates of DNA polymerase. Alternatively, an ET dye set can be constructed using cyanine (Cy2) as a donor and Cl$_2$ FAM, Cl$_2$R6G, Cl$_2$TAM, or Cl$_2$ROX as energy acceptors. Since Cy2 possesses higher molar absorbance compared with the rhodamine and fluorescein derivatives, an ET system using Cy2 as a donor produces much stronger fluorescence signals than the system using FAM as a donor (Hung et al. 1996). FIG. 18 shows a synthetic scheme for an ET dye labeled nucleotide analogue with Cy2 as a donor and Cl$_2$FAM as an acceptor using similar coupling chemistry as for the synthesis of an energy transfer system using FAM as a donor (Lee et al. 1997). Coupling of Cl$_2$FAM (I) with spacer 4-aminomethylbenzoic acid (II) produces III, which is then converted to NHS ester IV. Coupling of IV with amino-Cy2, and then converting the resulting compound to a NHS ester produces V, which subsequently couples with amino-photolinker nucleotide VI yields the ET dye labeled nucleotide VII.

Figure 17:
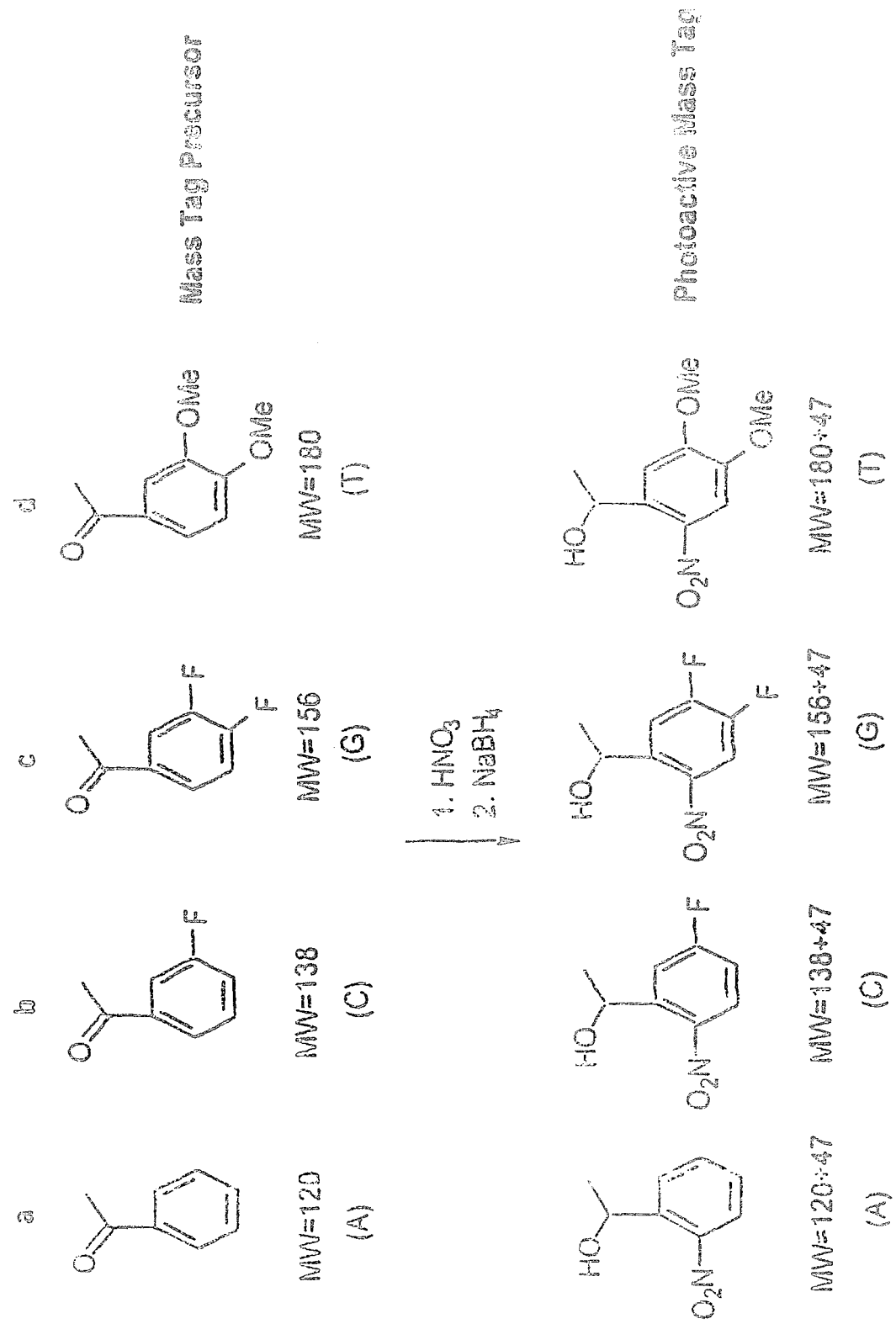
FIG. 17: Structures of four mass tag precursors and four photoactive mass tags. Precursors: a) acetophenone; b) 3-fluoroacetophenone; c) 3,4-difluoroacetophenone; and d) 3,4-dimethoxyacetophenone. Four photoactive mass tags are used to code for the identity of each of the four nucleotides (A, C, G, T).

6. Sequencing by Synthesis Evaluation Using Nucleotide Analogues $_{3'-HO}$-A-$_{Tag1}$, $_{3'-HO}$—C—$_{Tag2}$, $_{3'HO}$-G-$_{Tag3}$, $_{3'-HO}$-T-$_{Tag4}$ The precursors of four examples of mass tags are shown in FIG. 17. The precursors are: (a) acetophenone; (b) 3-fluoroacetophenone; (c) 3,4-difluoroacetophenone; and (d) 3,4-dimethoxyacetophenone. Upon nitration and reduction, four photoactive tags are produced from the four precursors and used to code for the identity of each of the four nucleotides (A, C, G, T). Clean APCI mass spectra are obtained for the four mass tag precursors (a, b, c, d) as shown in FIG. 18. The peak with m/z of 121 is a, 139 is b, 157 is c, and 181 is d. This result shows that these four mass tags are extremely stable and produce very high resolution data in an APCI mass spectrometer with no cross talk between the mass tags. In the examples shown below, each of the unique m/z from each mass tag translates to the identity of the nucleotide [Tag-1 (m/z,150)=A; Tag-2 (m/z,168)=C; Tag-3 (m/z,186)=G; Tag-4 (m/z,210).=T].

Figure 19:
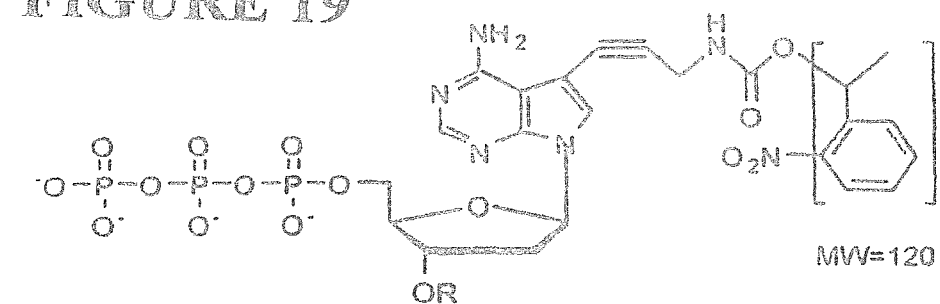
FIG. 19: Examples of structures of four nucleotide analogues for use in the sequencing by synthesis approach. Each nucleotide analogue has a unique mass tag attached to the base through a photocleavable linker, and the 3'-OH is either exposed or capped with a MOM group or an allyl group. The square brackets indicated that the mass tag is cleavable. R=H, $CH_2OCH_3$ (MOM) or $CH_2CH=CH_2$ (Allyl).
Figure 19:
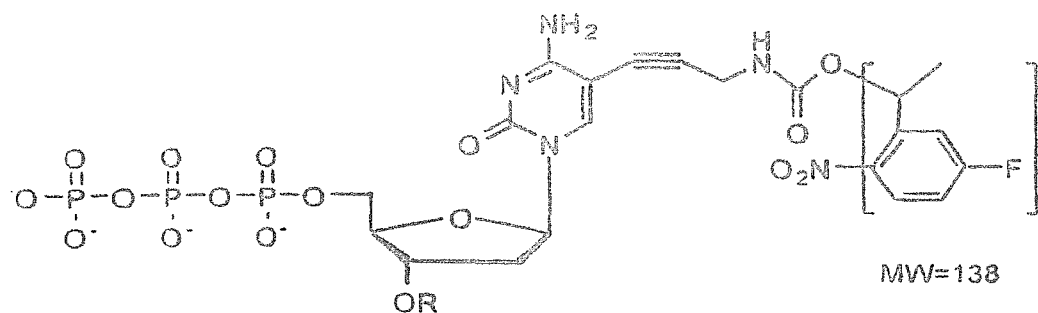
Figure 19:
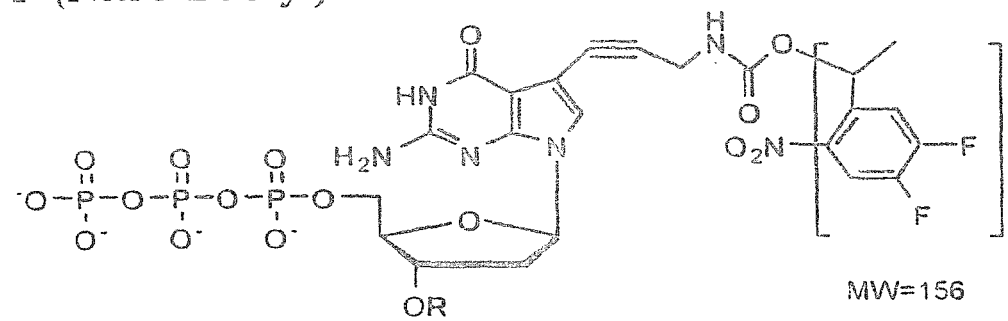
Figure 19:
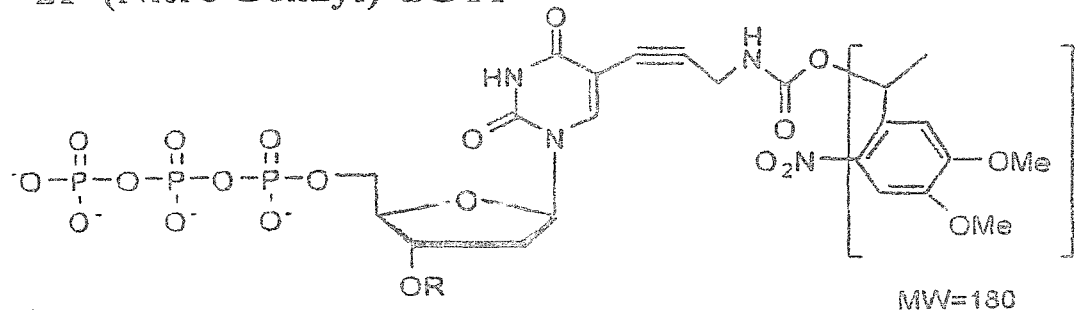

Different combinations of mass tags and nucleotides can be used, as indicated by the general scheme: $_{3'-HO}$-A-$_{Tag1}$, $_{3'-HO}$—C—$_{Tag2}$, $_{3'HO}$-G-$_{Tag3}$, $_{3'-HO}$-T-$_{Tag4}$ where Tag1, Tag2, Tag3, and Tag4 are four different unique cleavable mass tags. Four specific examples of nucleotide analogues are shown in FIG. 19. In FIG. 19, "R" is H when the 3'-OH group is not capped. As discussed above, the photo cleavable 2-nitro benzyl moiety has been used to link biotin to DNA and protein for efficient removal by UV light (~350 nm) irradiation (Olejnik et al. 1995, 1999). Four different 2-nitro benzyl groups with different molecular weights as mass tags are used to form the mass tag labeled nucleotides as shewn in FIG. 19: 2-nitro-α-methyl-benzyl (Tag-1) codes for A; 2-nitro-α-methyl-3-fluorobenzyl (Tag-2) codes for C; 2-nitro-α-methyl-3,4-difluorobenzyl (Tag-3) codes for G; 2-nitro-α-methyl-3,4 -dimethoxybenzyl (Tag-4 ) codes for T.

Figure 20:
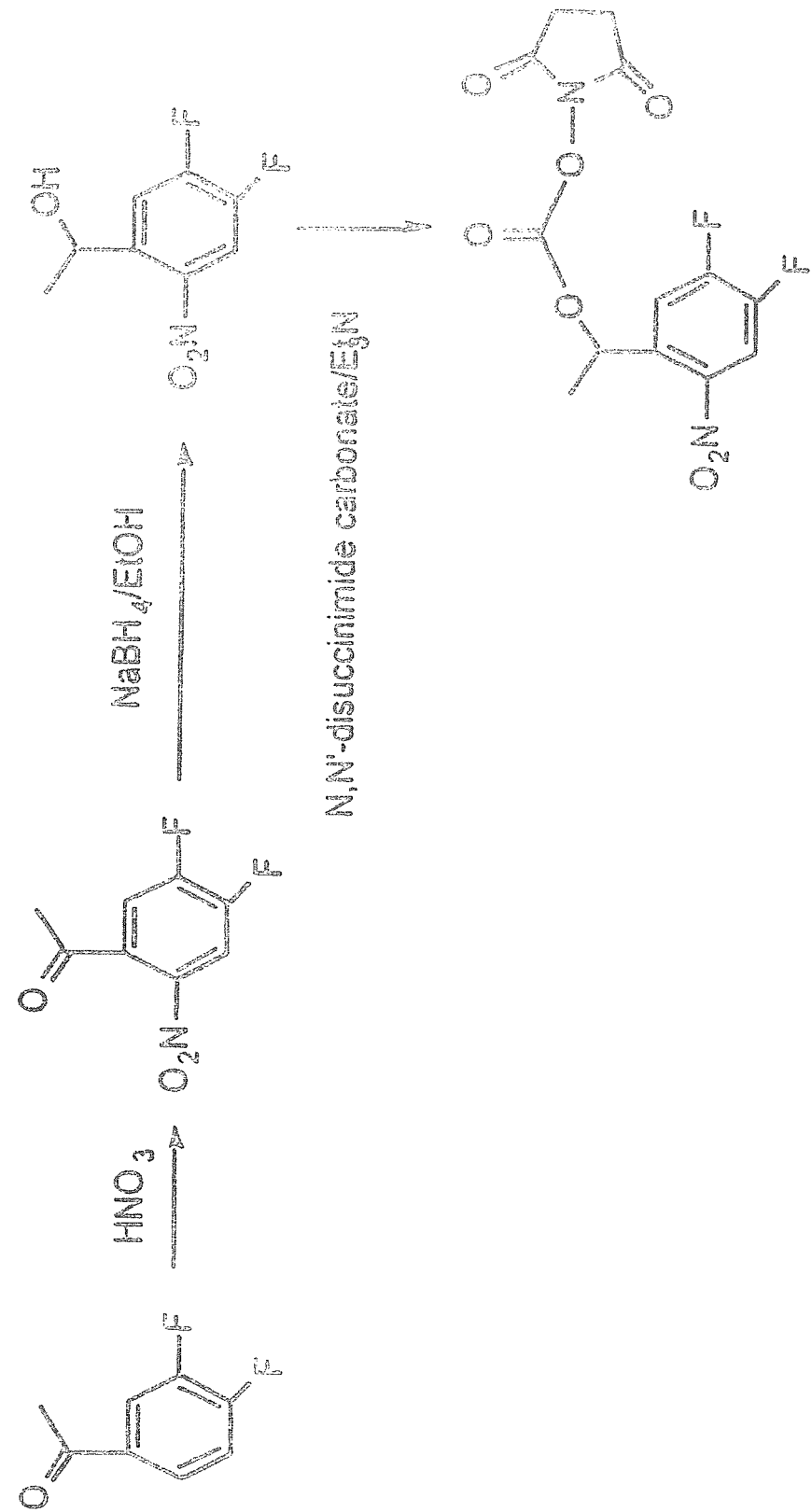
FIG. 20: Example of synthesis of NHS ester of one mass tag (Tag-3). A similar scheme is used to create other mass tags.
Figure 21:
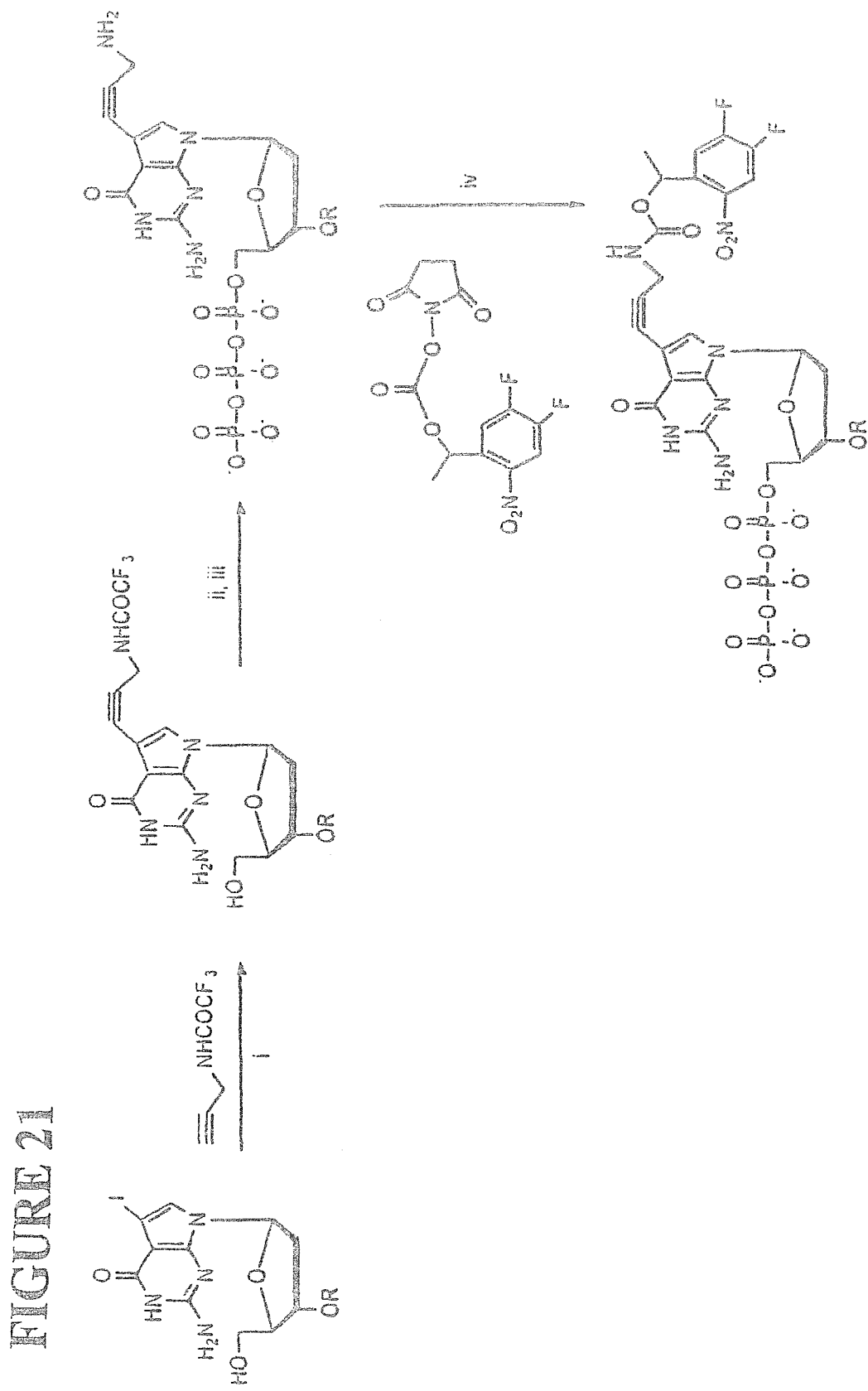
FIG. 21: A representative scheme for the synthesis of the nucleotide analogue $_{3'-RO}$-G-$_{Tag3}$. A similar scheme is used to create the other three modified bases $_{3'-RO}$-A-$_{Tag1}$, $_{3'-RO}$-C-$_{Tag2}$, $_{3'-RO}$-T-$_{Tag4}$. (i) tetrakis(triphenylphosphine)palladium(0); (ii) $POCl_3$, $Bn_4N^+$pyrophosphate; (iii) $NH_4OH$; (iv) $Na_2CO_3/NaHCO_3$ (pH=9.0)/DMSO.

As a representative example, the synthesis of the NHS ester of one mass tag (Tag-3) is shown in FIG. 20. A similar scheme is used to create the other mass tags. The synthesis of $_{3'-HO}$-G-$_{Tag3}$ is shown in FIG. 21 using well-established procedures (Prober et al. 1987; Lee et al 1992 and Hobbs et al. 1991). 7-propargylamino-dGTP is first prepared by reacting 7-I-dGTP with N-trifluoroacetylpropargyl amine, which is then coupled with the NHS-Tag-3 to produce $_{3'-HO}$-G-$_{TAG3}$. The nucleotide analogues with a free 3'-OH are good substrates for the polymerase.

Figure 9:
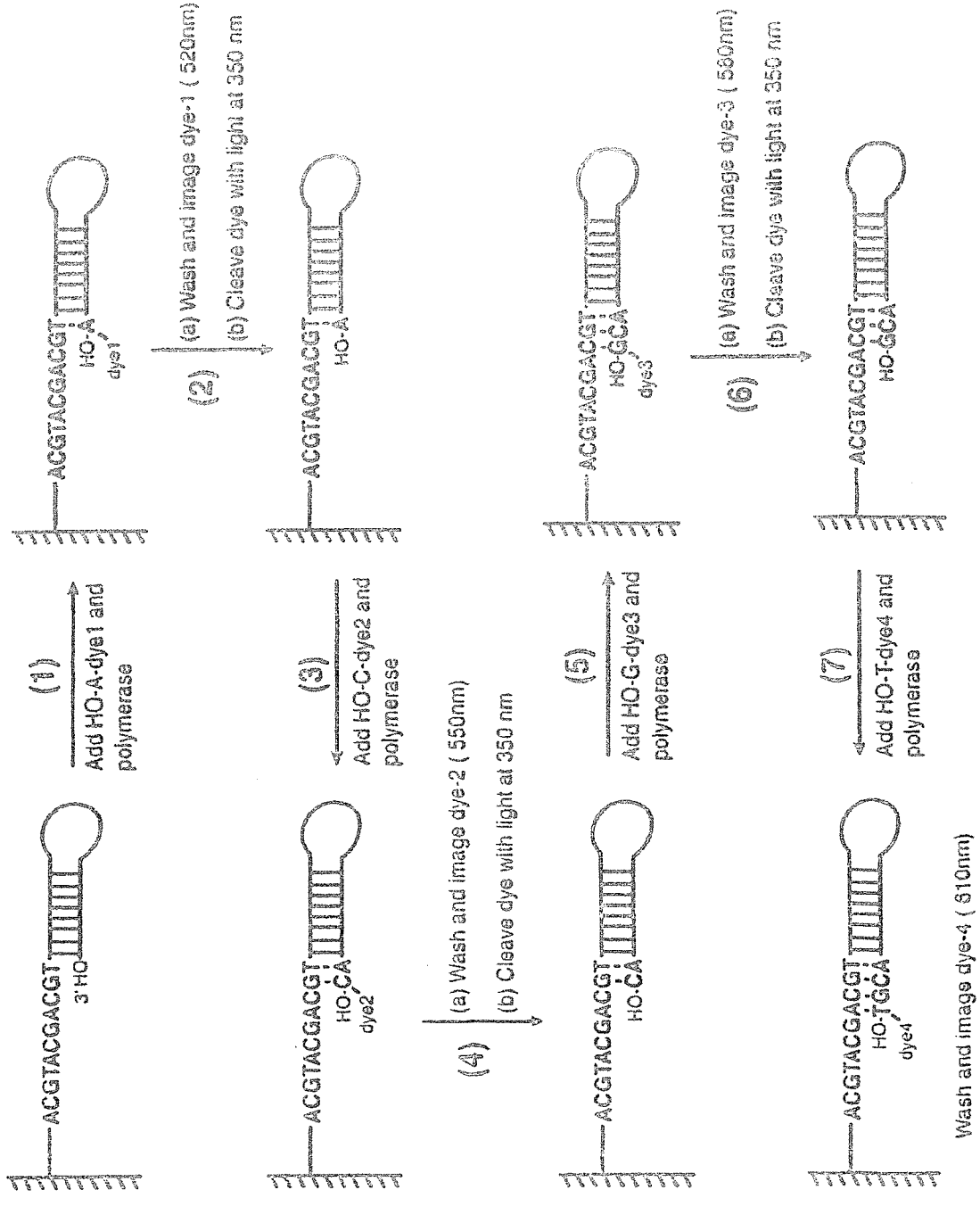
FIG. 9: A scheme for testing the sequencing by synthesis approach. Each nucleotide, modified by the attachment of a unique fluorescent dye, is added one by one, based on the complimentary template. The dye is detected and cleaved to test the approach. Dye1=Fam; Dye2=R6G; Dye3=Tam; Dye4=Rox.
Figure 22:
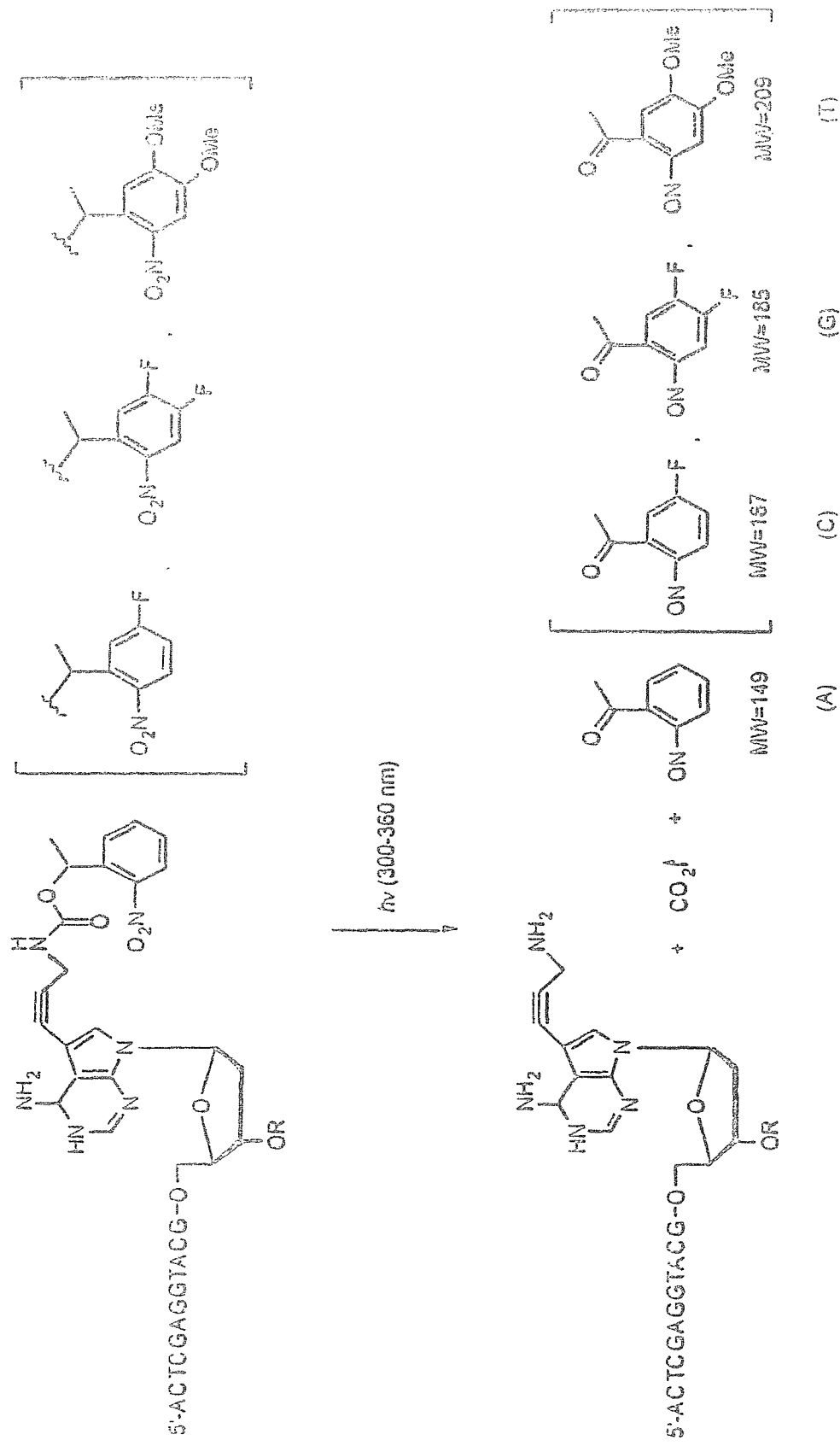
FIG. 22: Examples of expected photocleavage products of DNA containing a photocleavable mass tag.

The sequencing by synthesis approach can be tested using mass tags using a scheme similar to that show for dyes in FIG. 9. A DNA template containing a portion of nucleotide sequence that has no repeated sequences after the priming site, is synthesized and immobilized to a glass channel. $_{3'\text{-}HO}$-A-$_{Tag1}$ and DNA polymerase are added to the self-primed DNA moiety to allow the incorporation of the nucleotide into the 3' site of the DNA. Then the steps in FIG. 2B are followed (the chemical cleavage is not required here because the 3'-OH is free) to detect the mass tag from Tag-1 (m/z=150). Next, $_{3'\text{-}HO}$—C—$_{Tag2}$ is added and the resulting mass spectra is measured after cleaving Tag-2 (m/z=168). Next, $_{3'\text{-}HO}$-G-$_{Tag3}$ and $_{3'\text{-}HO}$-T-$_{Tag4}$ are added in turn and the mass spectra of the cleavage products Tag-3 (m/z=186) and Tag-4 (m/z=210) are measured. Examples of expected photocleavage products are shown in FIG. 22. The photocleavage mechanism is as described above for the case where the unique labels are dyes. Light absorption (300-360 nm) by the aromatic 2-nitro benzyl moiety causes reduction of the 2-nitro group to a nitroso group and an oxygen insertion into the carbon-hydrogen bond located in the 2-position followed by cleavage and decarboxylation (Pillai 1980).

The synthesis of nucleotide analogues $_{3'\text{-}RO}$-A-$_{Tag1}$, $_{3'\text{-}RO}$—C—$_{Tag2}$, $_{3'\text{-}RO}$-G-$_{Tag3}$, $_{3'\text{-}RO}$-T-$_{Tag4}$ can be pursued for further study of the system a discussed above for the case where the unique labels are dyes. Here the 3'-OH is capped in all four nucleotide analogues, which then can be mixed together with DNA polymerase and used to evaluate the sequencing system using a scheme similar to that in FIG. 9. The MOM (—$CH_2OCH_3$) or allyl (—$CH_2CH=CH_2$) group is used to cap the 3'-OH group using well-established synthetic procedures (FIG. 13) (Fuji et al. 1975, Metzker et al. 1994). These groups can be removed chemically with high yield as shown in FIG. 14 (Ireland, et al. 1986; Kamal et al, 1999). The chemical cleavage of the MOM and allyl groups is fairly mild and specific, so as not to degrade the DNA template moiety.

7. Parallel Channel System for Sequencing by Synthesis

Figure 23:
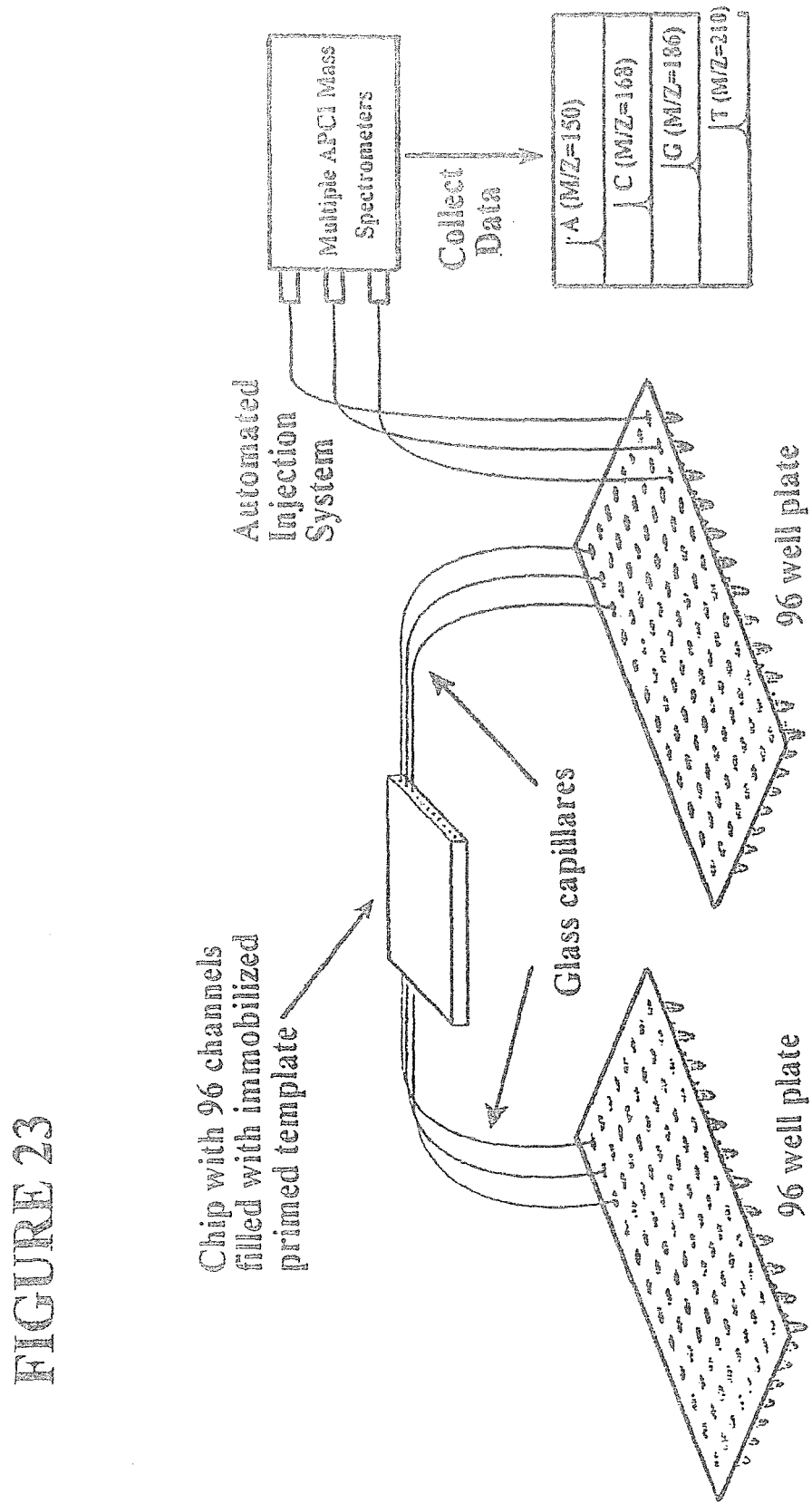
FIG. 23: System for DNA sequencing comprising multiple channels in parallel and multiple mass spectrometers in parallel. The example shows 96 channels in a silica glass chip.

FIG. 23 illustrates an example of a parallel channel system. The system can be used with mass tag labels as shown and also with dye labels. A plurality of channels in a silica glass chip are connected on each end of the channel to a well in a well plate. In the example shown there are 96 channels each connected to its own wells. The sequencing system also permits a number of channels other than 96 to be used. 96 channel devices for separating DNA sequencing and sizing fragments have been reported (Woolley and Mathies 1994, Woolley et al. 1997, Simpson et al. 1998). The chip is made by photolithographic masking and chemical etching techniques. The photolithographically defined channel patterns are etched in a silica glass substrate, and then capillary channels (id ~100 μm) are formed by thermally bonding the etched substrate to a second silica glass slide. Channels are porous to increase surface area. The immobilized single stranded DNA template chip is prepared according to the scheme shown in FIG. 3. Each channel is first treated with 0.5 M NaOH, washed with water, and is then coated with high density 3-aminopropyltrimethoxysilane in aqueous ethanol (Woolley et al. 1994) forming a primary amine surface. Succinimidyl (NHS) ester of triarylphosphine (1) is covalently coupled with the primary amine group converting the amine surface to a novel triarylphosphine surface, which specifically reacts with DNA containing an azido group (2) forming a chip with immobilized DNA. Since the azido group is only located at the 5' end of the DNA and the coupling reaction is through the unique reaction of triarylphosphine moiety with azido group in aqueous solution (Saxon and Bertozzi 2000), such a DNA surface provides an optimized condition for hybridization. Fluids, such as sequencing reagents and washing solutions, can be easily pressure driven between the two 96 well plates to wash and add reagents to each channel in the chip for carrying out the polymerase reaction as well as collecting the photocleaved labels. The silica chip is transparent to ultraviolet light (λ~350 nm). In the Figure, photocleaved mass tags are detected by an APCI mass spectrometer upon irradiation with a UV light source.

8. Parallel Mass Tag Sequencing by Synthesis System

The approach disclosed herein comprises detecting four unique photoreleased mass tags, which can have molecular weights from 150 to 250 daltons, to decode the DNA sequence, thereby obviating the issue of detecting large DNA fragments using a mass spectrometer as well as the stringent sample requirement for using mass spectrometry to directly detect long DNA fragments. It takes 10 seconds or less to analyze each mass tag using the APCI mass spectrometer. With 8 miniaturized APCI mass spectrometers in a system, close to 100,000 bp of high quality digital DNA sequencing data could be generated each day by each instrument using this approach. Since there is no separation and purification requirements using this approach, such a system is cost effective.

To make mass spectrometry competitive with a 96 capillary array method for analyzing DNA, a parallel mass spectrometer approach is needed. Such a complete system has not been reported mainly due to the fact that most of the mass spectrometers are designed to achieve adequate resolution for large biomolecules. The system disclosed herein requires the detection of four mass tags, with molecular weight range between 150 and 250 daltons, coding for the identity of the four nucleotides (A, C, G, T). Since a mass spectrometer dedicated to detection of these mass tags only requires high resolution for the mass range of 150 to 250 daltons instead of covering a wide mass range, the mass spectrometer can be miniaturized and have a simple design. Either quadrupole (including ion trap detector) or time-of-flight mass spectrometers can be selected for the ion optics. While modern mass spectrometer technology has made it possible to produce miniaturized mass spectrometers, most current research has focused on the design of a single stand-alone miniaturized mass spectrometer. Individual components of the mass spectrometer has been miniaturized for enhancing the mass spectrometer analysis capability (Liu et al. 2000, Zhang et al. 1999). A miniaturized mass spectrometry system using multiple analyzers (up to 10) in parallel has been reported (Badman and Cooks 2000). However, the mass spectrometer of Badman and Cook was designed to measure only single samples rather than multiple samples in parallel. They also noted that the miniaturization of the ion trap limited the capability of the mass spectrometer to scan wide mass ranges. Since the approach disclosed herein focuses on detecting four small stable mass tags (the mass range is less than 300 daltons), multiple miniaturized APCI mass spectrometers are easily constructed and assembled into a single unit for parallel analysis of the mass tags for DNA sequencing analysis.

Figure 24:
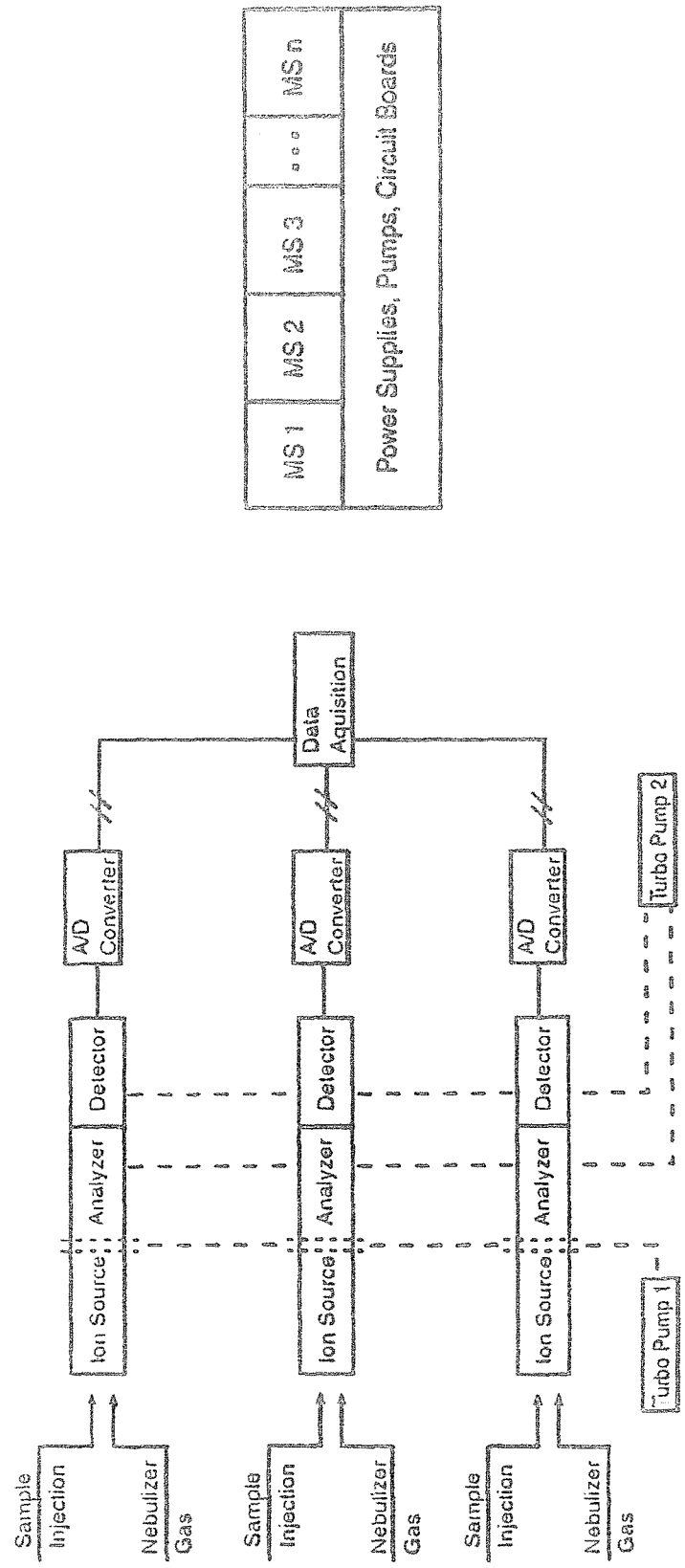
FIG. 24: Parallel mass spectrometry system for DNA sequencing. Example shows three mass spectrometers in parallel. Samples are injected into the ion source where they are mixed with a nebulizer gas and ionized. A turbo pump is used to continuously sweep away free radicals, neutral compounds and other undesirable elements coming from the ion source. A second turbo pump is used to generate a continuous vacuum in all three analyzers and detectors simultaneously. The acquired signal is then converted to a digital signal by the A/D converter. All three signals are then sent to the data acquisition processor to convert the signal to identify the mass tag in the injected sample and thus identify the nucleotide sequence.

A complete parallel mass spectrometry system includes multiple APCI sources interfaced with multiple analyzers, coupled with appropriate electronics and power supply configuration. A mass spectrometry system with parallel detection capability will overcome the throughput bottleneck issue for application in DNA analysis. A parallel system containing multiple mass spectrometers in a single device is illustrated in FIGS. 23 and 24. The examples in the figures show a system with three mass spectrometers in parallel. Higher throughput is obtained using a greater number of in parallel mass spectrometers.

As illustrated in FIG. 24, the three miniature mass spectrometers are contained in one device with two turbo-pumps. Samples are injected into the ion source where they are mixed with a nebulizer gas and ionized. One turbo pump is used as a differential pumping system to continuously sweep away free radicals, neutral compounds and other undesirable elements coming from the ion source at the orifice between the ion source and the analyzer. The second turbo pump is used to generate a continuous vacuum in all three analyzers and detectors simultaneously. Since the corona discharge mode and scanning mode of mass spectrometers are the same for each miniaturized mass spectrometer, one power supply for each analyzer and the ionization source can provide the necessary power for all three instruments. One power supply for each of the three independent detectors is used for spectrum collection. The data obtained are transferred to three independent A/D converters and processed by the data system simultaneously to identify the mass tag in the injected sample and thus identify the nucleotide. Despite containing three mass spectrometers, the entire device is able to fit on a laboratory bench top.

9. Validate the Complete Sequencing by Synthesis System By Sequencing P53 Genes

The tumor suppressor gene p53 can be used as a model system to validate the DNA sequencing system. The p53 gene is one of the most frequently mutated genes in human cancer (O'Connor et al, 1997). First, a base pair DNA template (shown below) is synthesized containing an azido group at the 5' end and a portion of the sequences from exon 7 and exon 8 of the p53 gene:

(SEQ ID NO: 2)
5'-N$_3$-TTCCTGCATGGGCGGCATGAACCCGAGGCCCATCCTCACCATCAT
CACACTGGAAGACTCCAGTGGTAATCTACTGGGACGGAACAGCTTTGAGG
TGCATT-3'.

This template is chosen to explore the use of the sequencing system for the detection of clustered hot spot single base mutations. The potentially mutated bases are underlined (A, G, C and T) in the synthetic template. The synthetic template is immobilized on a sequencing chip or glass channels, then the loop primer is ligated to the immobilized template as described in FIG. 6, and then the steps in FIG. 2 are followed for sequencing evaluation. DNA templates generated by PGR can be used to further validate the DNA sequencing system. The sequencing templates can be generated by PCR using flanking primers (one of the pair is labeled with an azido group at the 5' end) in the intron region located at each p53 axon boundary from a pool of genomic DNA (Boehringer, Indianapolis, Ind.) as described by Fu et al. (1998) and then immobilized on the DNA chip for sequencing evaluation.

REFERENCES

Antao V P, Lai S Y, Tinoco I Jr. (1991) A thermodynamic study of unusually stable RNA and DNA hairpins. *Nucleic Acids Res.* 19: 5901-5905.

Axelrod V D, Vartikyan R M, Aivazashvili V A, Beabealashvili R S. (1978) Specific termination of RNA polymerase synthesis as a method of RNA and DNA sequencing. *Nucleic Acids Res.* 5(10): 3549-3563.

Badman E R and Cooks R G. (2000) Cylindrical Ion Trap Array with Mass Selection by Variation in Trap Dimensions *Anal. Chem.* 72(20):5079-5086.

Badman E R and Cooks R G. (2000) A Parallel Miniature Cylindrical Ion Trap Array. *Anal. Chem.* 72(14):3291-3297.

Bowling J M, Bruner K L, Cmarik J L, Tibbetts C. (1991) Neighboring nucleotide interactions during DNA sequencing gel electrophoresis. *Nucleic Acids Res.* 19: 3089-3097.

Burgess K, Jacutin S E, Lim D, Shitangkoon A. (1997) An approach to photolabile, fluorescent protecting groups. *J. Org. Chem.* 62(15): 5165-5168.

Canard B, Cardona B, Sarfati R S. (1995) Catalytic editing properties of DNA polymerases. *Proc. Natl. Acad. Sci. USA* 92: 10859-10863.

Caruthers M H. (1985) Gene synthesis machines: DNA chemistry and its uses. *Science* 230: 281-285.

Chee M, Yang R, Hubbell E, Berno, A, Huang, X C., Stern D, Winkler, J, Lockhart D J, Morris M S, Fodor, S P. (1996) Accessing genetic information with high-density DNA arrays. *Science,* 274: 610-614.

Cheeseman P C. Method For Sequencing Polynucleotides, U.S. Pat. No. 5,302,509, issued Apr. 12, 1994.

Dizidic I, Carrol, D I, Stillwell, R N, and Horning, M G. (1975) Atmospheric pressure ionization (API) mass spectrometry: formation of phenoxide ions from chlorinated aromatic compounds *Anal. Chem.,* 47: 1308-1312.

Fu D J, Tang K, Braun A, Reuter D, Darnhofer-Demar B, Little D P, O'Donnell M J, Cantor C R, Koster H. (1998) Sequencing exons 5 to 8 of the p53 gene by MALDI-TOF mass spectrometry. *Nat Biotechnol.* 16: 381-384.

Fuji K, Nakano S, Fujita E. (1975) An improved method for methoxymethylation of alcohols under mild acidic conditions. *Synthesis* 276-277.

Hobbs F W Jr, Cocuzza A J. Alkynylamino-Nucleotides. U.S. Pat. No. 5,047,519, issued Sep. 10, 1991.

Hung S C; Ju J; Mathies R A; Glazer A N. (1996) Cyanine dyes with high absorption cross section as donor chromophores in energy transfer primers. *Anal Biochem.* 243(1): 15-27.

Hyman E D, (1988) A new method of sequencing DNA. *Analytical Biochemistry* 174: 423-436.

Ireland R E, Varney M D (1986) Approach to the total synthesis of chlorothricolide-synthesis of (+/−)-19.20-dihydro-24-O-methylchlorothricolide, methyl-ester, ethyl carbonate. *J. Org. Chem.* 51: 635-648.

Ju J, Glazer A N, Mathies R A. (1996) Cassette labeling for facile construction of energy transfer fluorescent primers. *Nucleic Acids Res.* 24: 1144-1148.

Ju J, Ruan C, Fuller C W, Glazer A N Mathies R A. (1995) Energy transfer fluorescent dye-labeled primers for DNA sequencing and analysis. *Proc. Natl. Acad. Sci. USA* 92: 4347-4351.

Kamal A, Laxman E, Rao N V. (1999) A mild and rapid regeneration of alcohols from their allylic ethers by chlorotrimethylsilane/sodium iodide. *Tetrahedron letters* 40: 371-372.

Kheterpal I, Scherer J, Clark S M, Radhakrishnan A, Ju J, Ginther C L, Sensabaugh G F, Mathies R A. (1996) DNA Sequencing Using a Four-Color Confocal Fluorescence Capillary Array Scanner. *Electrophoresis.* 17: 1852-1859.

Khoukhi N, Vaultier M, Carrie R. (1987) Synthesis and reactivity of methyl-azido butyrates and ethyl-azido valerates and of the corresponding acid chlorides as useful reagents for the aminoalkylation. *Tetrahedron* 43: 1811-1822.

Lee L G, Connell C R, Woo S L, Cheng R D, Mcardle B F, Fuller C W, Halloran N D, Wilson R K. (1992) DNA sequencing with dye-labeled terminators and T7 DNA-polymerase-effect of dyes and dNTPs on incorporation of dye-terminators and probability analysis of termination fragments. *Nucleic Acids Res.* 20: 2471-2483.

Lee L G, Spurgeon S L, Heiner C R, Benson S C, Rosenblum B B, Menchen S M, Graham R J, Constantinescu A, upadhya K G, Cassel J M, (1997) New energy transfer dyes for DNA sequencing. *Nucleic Acids Res.* 25: 2816-2822.

Liu H. H., Felton C., Xue Q. F., Zhang B., Jedrzejewski P., Karger B. L. and Foret F. (2000) Development of multichannel Devices with an Array of Electrospray tips for high-throughput mass spectrometry. *Anal. Chem.* 72: 3303-3310.

Metzker M L, Raghavachari R, Richards S, Jacutin S E, Civitello A, Burgess K, Gibbs R A. (1994) Termination of DNA synthesis by novel 3'-modified-deoxyribonucleoside 5'-triphosphates. *Nucleic Acids Res.* 22: 4259-4267.

O'Connor P M, Jackman J, Bae I, Myers T G, Fan S, Mutoh M, Scudiero D A, Monks A, Sausville E A, Weinstein J N, Friend S, Fornace A J Jr, Kohn K W. (1997) Characterization of the p53 tumor suppressor pathway in cell lines of the National Cancer Institute anticancer drug screen and correlations with the growth-inhibitory potency of 123 anticancer agents. *Cancer Res.* 57: 4285-4300.

Olejnik J, Ludemann H C, Krzymanska-Olejnik E, Berkenkamp S, Hillenkamp F, Rothschild K J. (1999) Photocleavable peptide-DNA conjugates: synthesis and applications to DNA analysis using MALDI-MS. *Nucleic Acids Res.* 27: 4626-4631.

Olejnik J, Sonar S, Krzymanska-Olejnik E, Rothschild K J. (1995) Photocleavable biotin derivatives: a versatile approach for the isolation of biomolecules. *Proc. Natl. Acad. Sci. USA,* 92: 7590-7594.

Pelletier H. Sawaya M R, Kumar A, Wilson S H, Kraut J. (1994) Structures of ternary complexes of rat DNA polymerase β, a DNA template-primer, and ddCTP. *Science* 264: 1891-1903.

Pennisi E. (2000) DOE Team Sequences Three Chromosomes. *Science* 288: 417-419.

Pillai V N R. (1980) Photoremovable Protecting Groups in Organic Synthesis. *Synthesis* 1-62.

Prober J M, Trainor G L, Dam R J, Hobbs F W, Robertson C W, Zagursky R J, Cocuzza A J, Jensen M A, Baumeister K. (1987) A system for rapid DNA sequencing with fluorescent chain-terminating dideoxynucleotides. *Science* 238: 336-341.

Rollaf F. (1982) Sodium-borohydride reactions under phase-transfer conditions—reduction of azides to amines. *J. Org. Chem.* 47: 4327-4329.

Ronaghi M, Uhlen M, Nyren P. (1998) A sequencing Method based on real-time pyrophosphate. *Science* 281: 364-365.

Rosenblum B B, Lee L G, Spurgeon S L, Khan S H, Menchen S M, Heiner C R, Chen S M. (1997) New dye-labeled terminators for improved DNA sequencing patterns. *Nucleic Acids Res.* 25: 4500-4504.

Roses A. (2000) Pharmacogenetics and the practice of medicie. *Nature.* 405: 857-865.

Salas-Solano O, Carrilho E, Kotler L, Miller A W, Goetzinger W, Sosic Z, Karger B L, (1998) Routine DNA sequencing of 1000 bases in less than one hour by capillary electrophoresis with replaceable linear polyacrylamide solutions. *Anal. Chem.* 70: 3996-4003.

Saxon E and Bertozzi C R (2000) Cell surface engineering by a modified Staudinger reaction. *Science* 287: 2007-2010.

Schena M, Shalon D, Davis, R. Brown P. O. (1995) Quantitative monitoring of gene expression patterns with a cDNA microarray. *Science* 270: 467-470.

Simpson P C, Adam D R, Woolley T, Thorsen T, Johnston R, Sensabaugh G F, and Mathies R A. (1998) High-throughput genetic analysis using microfabricated 96-sample capillary array electrophoresis microplates. *Proc. Natl. Acad. Sci. U. S. A.* 95: 2256-2261.

Smith L M, Sanders J Z, Kaiser R J, Hughes P, Dodd C, Connell C R, Heinar C, Kent S B H, Hood L E. (1986) Fluorescence detection in automated DNA sequencing analysis. *Nature* 321: 674-679.

Tabor S, Richardson C. C. (1987) DNA sequence analysis with a modified bacteriophage T7 DNA polymerase. *Proc. Natl. Acad. Sci. U.S.A.* 84: 4767-4771.

Tabor S. & Richardson, C C. (1995) A single residue in DNA polymerases of the *Escherichia coli* DNA polymerase I family is critical for distinguishing between deoxy- and dideoxyribonucleotides. *Proc. Natl. Acad. Sci. U.S.A.* 92: 6339-6343.

Turro N J. (1991) Modern Molecular Photochemistry; University Science Books, Mill Valley, Calif.

Velculescu V E, Zhang, I, Vogelstein, B. and Kinzler K W (1995) Serial Analysis of Gene Expression. *Science* 270: 484-487.

Welch M B, Burgess K, (1999) Synthesis of fluorescent, photolabile 3'-O-protected nucleoside triphosphates for the base addition sequencing scheme. *Nucleosides and Nucleotides* 18: 197-201.

Woolley A T, Mathies R A. (1994) Ultra-high-speed DNA fragment separations using microfabricatad capillary array electrophoresis chips. *Proc. Natl. Acad. Sci. USA.* 91: 11348-11352.

Woolley A T, Sensabaugh G F and Mathies R A. (1997) High-Speed DNA Genotyping Using Microfabricated Capillary Array Electrophoresis Chips, *Anal. Chem.* 69(11); 2181-2186.

Yamakawa H, Ohara O. (1997) A DNA cycle sequencing reaction that minimizes compressions on automated fluorescent sequencers. *Nucleic. Acids. Res.* 25: 1311-1312.

Zhang X H, Chiang V L, (1996) Single-stranded DNA ligation by T4 RNA ligase for PCR cloning of 5'-noncoding fragments and coding sequence of a specific gene. *Nucleic Acids Res.* 24: 990-991.

Zhang B., Liu H. Karger B L. Foret F. (1999) Microfabricated devices for capillary electrophoresis-electrospray mass spectrometry. *Anal. Chem.* 71: 3258-3264.

Zhu Z, Chao J, Yu H, Waggoner A S. (1994) Directly labeled DNA probes using fluorescent nucleotides with different length linkers. *Nucleic Acids Res.* 22: 3418-3422

What is claimed is:

1. A thymine deoxyribonucleotide analogue having the structure:

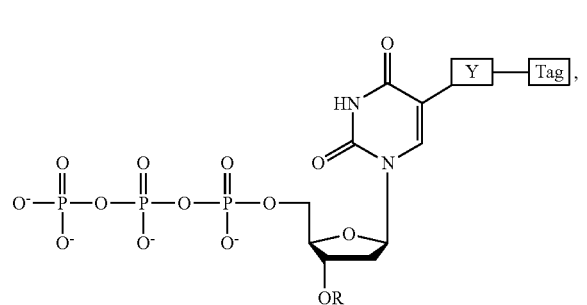

wherein R (a) represents a small, chemically cleavable, chemical group capping the oxygen at the 3' position of the deoxyribose of the deoxyribonucleotide analogue, (b) does not interfere with recognition of the analogue as a substrate by a DNA polymerase, (c) is stable during a DNA polymerase reaction, (d) does not contain a ketone group, and (e) is not a —CH$_2$CH=CH$_2$ group;
wherein OR is not a methoxy group or an ester group;
wherein the covalent bond between the 3'-oxygen and R is stable during a DNA polymerase reaction;
wherein tag represents a detectable fluorescent moiety;
wherein Y represents a chemically cleavable, chemical linker which (a) does not interfere with recognition of the analogue as a substrate by a DNA polymerase and (b) is stable during a DNA polymerase reaction; and
wherein the thymine deoxyribonucleotide analogue:
  i) is recognized as a substrate by a DNA polymerase,
  ii) is incorporated at the end of a growing strand of DNA during a DNA polymerase reaction,
  iii) produces a 3'-OH group on the deoxyribose upon cleavage of R,
  iv) no longer includes a tag on the base upon cleavage of Y, and
  v) is capable of forming hydrogen bonds with adenine or an adenine nucleotide analogue.

2. A thymine deoxyribonucleotide analogue having the structure:

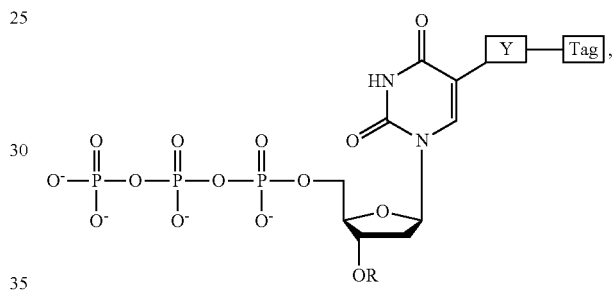

wherein R (a) represents a small, chemically cleavable, chemical group capping the oxygen at the 3' position of the deoxyribose of the deoxyribonucleotide analogue, (b) does not interfere with recognition of the analogue as a substrate by a DNA polymerase, (c) is stable during a DNA polymerase reaction, and (d) does not contain a ketone group;
wherein OR is not a methoxy group, an ester group, or an allyl ether group;
wherein the covalent bond between the 3'-oxygen and R is stable during a DNA polymerase reaction;
wherein tag represents a detectable fluorescent moiety;
wherein Y represents a chemically cleavable, chemical linker which (a) does not interfere with recognition of the analogue as a substrate by a DNA polymerase and (b) is stable during a DNA polymerase reaction; and
wherein the thymine deoxyribonucleotide analogue:
  i) is recognized as a substrate by a DNA polymerase,
  ii) is incorporated at the end of a growing strand of DNA during a DNA polymerase reaction,
  iii) produces a 3'-OH group on the deoxyribose upon cleavage of R,
  iv) no longer includes a tag on the base upon cleavage of Y, and
  v) is capable of forming hydrogen bonds with adenine or an adenine nucleotide analogue.

* * * * *